United States Patent [19]
Buchsbaum et al.

[11] Patent Number: 5,902,583
[45] Date of Patent: May 11, 1999

[54] GENETIC INDUCTION OF RECEPTORS FOR TARGETED RADIOTHERAPY

[75] Inventors: Donald J. Buchsbaum; David T. Curiel; Mohammad B. Khazaeli, all of Birmingham; David Raben, Homewood; Murray Stackhouse, Helena, all of Ala.

[73] Assignee: UAB Research Foundation, Birmingham, Ala.

[21] Appl. No.: 08/739,826

[22] Filed: Feb. 11, 1997

Related U.S. Application Data

[60] Provisional application No. 60/008,147, Oct. 31, 1995.
[51] Int. Cl.$^6$ .................. A61K 39/395; A61K 51/00; A01N 43/04
[52] U.S. Cl. .................. 424/130.1; 424/1.41; 424/1.49; 424/1.65; 424/1.17; 514/44
[58] Field of Search .................. 435/7, 7.2, 7.23; 424/85.1, 130.1, 1.41, 1.49, 1.65, 1.17; 514/44

[56] References Cited

U.S. PATENT DOCUMENTS 5,662,896  9/1997  Barber et al. .

OTHER PUBLICATIONS

Hartmann et al. Cancer Research, 54, 4362–4370, Aug. 15, 1994.

*Primary Examiner*—Lila Feisee
*Assistant Examiner*—Lin Sun-Hoffman
*Attorney, Agent, or Firm*—Benjamin Aaron Adler

[57] ABSTRACT

The present invention provides a method to achieve radio-isotopic localization at tumor sites, i.e., a method of enhancing radiolabeled ligand localization to a tumor in an individual in need of such treatment, comprising the steps of: transducing the tumor with a gene encoding a membrane expressed protein unique to the tumor; and administering to said individual a radiolabeled ligand which specifically binds to the protein. The use of gene therapy technology to induce expression of high affinity membrane molecules/receptors can enhance the specificity of radioisotope localization while the use of radioactive isotopes with the ability to deliver radiation damage across several cell diameters will compensate for less than perfect transduction efficiency.

22 Claims, 31 Drawing Sheets

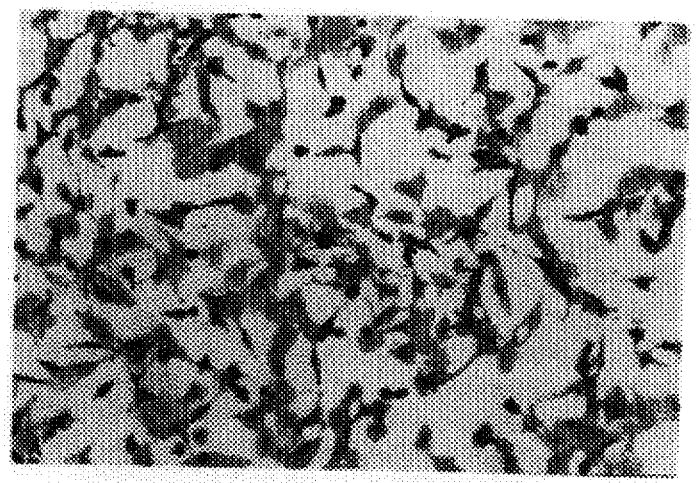
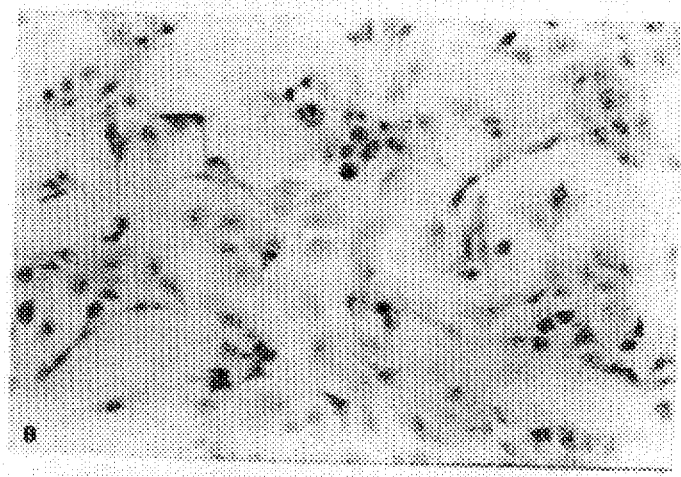
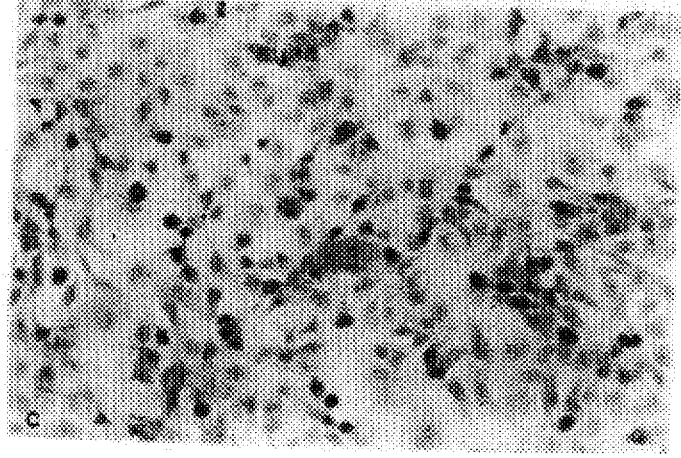
FIGURE 3

GENETIC INDUCTION OF RECEPTORS FOR TARGETED RADIOTHERAPY

CROSS REFERENCE TO RELATED APPLICATION

This application is a continuing application of provisional application U.S. Ser. No. 60/008,147, filed Oct. 31, 1995, now abandoned.

BACKGROUND OF THE INVENTION

1. Field of the Invention

The present invention relates generally to the fields of radioimmunobiology and gene therapy. More specifically, the present invention relates to a novel technique of genetic induction of receptors for targeted radiotherapy.

2. Description of the Related Art

The paradigm of radioimmunotherapy (RAIT) has been based upon the premise that a targeting molecule (e.g. an antibody) carrying a radionuclide has the potential of selectively delivering radiation to tumor sites. Considerable clinical experience with this strategy has been accomplished over the past decade, with success limited primarily to malignant lymphomas (1,2). This limited efficacy reflects fundamental problems in achieving adequate tumor localization of radiolabeled antibodies, which may be due either to inadequate intratumoral expression of the target antigen or to biodistribution problems associated with the use of intact antibody as the targeting moiety (3–6). A variety of strategies have thus been developed as alternatives to radiolabeled intact mouse monoclonal antibodies (MAbs) to enhance tumor localization of an injected radiolabeled ligand, including the employment of second generation high affinity antibodies, humanized antibodies, genetically engineered antibody fragments, peptides, and pretargeting of unlabeled antibody followed by radiolabeled haptens.

"Targeted" radiation therapy is an important cancer research strategy. The use of external beam radiation therapy has produced curative treatment programs for several tumor types. However, this technique has practical limitations in regards to limited field of therapy, normal tissue toxicity, and radioresistance mechanisms. Considerable research efforts have been directed at ways to "target" radioactive isotopes to sites of malignant disease. Currently, the use of monoclonal antibodies directed to "tumor-associated" antigens on cancer cells represents one approach to this problem which has had success in various animal model systems (5–9) and is the subject of considerable current phase I and II trials in man (10–14). Such a strategy provides the ability to localize radioactive isotopes to multiple sites of disease with hopefully adequate amounts of radiation to produce an antitumor effect and/or radioimmune imaging for diagnostic purposes. A second emerging strategy is to use radioactively labeled peptides able to bind to receptor positive tumor cells (e.g. octreotide to somatostatin receptors in malignant carcinoid) (15,16). Research efforts which provide better radioactive isotope delivery systems and/or targeting strategies will enhance the ability to apply targeted radiation therapy.

Radiolabeled monoclonal antibodies (single-step radioimmunotherapy) have serious limitations in treating human cancer. Successful application of radiolabeled monoclonal antibodies in a single-step protocol for radioimmunodetection and radioimmunotherapy of tumors has been hindered in man by problems related to the low percentage uptake of injected radioactivity in tumors (0.001 to 0.1% ID/g), the slow penetration of relatively large (160 kD) intact antibodies into tumors and heterogeneous distribution, their long persistence times in normal tissues leading to high background radioactivity and bone marrow suppression, and the development of human anti-mouse antibody (HAMA) responses. To overcome these problems, several groups have considered the use of antibody fragments and single chain antibodies (17–22), regional administration (23–25), the use of various radionuclides (5), the use of more stable (26) or enzymatically cleavable chelating agents (27), the use of cytokines to upregulate tumor-associated antigen expression (28, 29), irradiation of the tumor to increase vascular permeability (14, 30–32), the use of cytokines to protect against bone marrow suppression (33, 34), and the use of autologous bone marrow transplantation (2, 35). Despite these efforts, the results of clinical radioimmunotherapy of solid tumors have been disappointing. In spite of these shortcomings, antitumor efficacy has been demonstrated in clinical trials for therapy of the radiosensitive lymphoma types of tumors.

The prior art is deficient in the lack of effective means of enhancing the therapeutic effects of immuno-directed radiation therapy. The present invention fulfills this longstanding need and desire in the art.

SUMMARY OF THE INVENTION

The present invention addresses the problem of poor intratumoral antigen expression to augment localization of tumor targeted radiolabeled ligands. This strategy has focused on gene transfer methods to achieve increased levels of tumor cell expression of the targeted antigen. For example, human glioma cells that do not express carcinoembryonic antigen (CEA) can be transduced in vitro with a recombinant replication-defective adenovirus encoding human CEA, which renders them susceptible to binding by radiolabeled anti-CEA antibodies. In this schema, enhanced in vivo radiolabeled antibody localization could also be achieved following in situ tumor transduction with the same vector. This method thus represents a new paradigm by which augmented therapeutic efficacy can be achieved through enhanced radiolabeled ligand localization to tumors expressing unique and novel antigens/receptors.

This strategy might also successfully be employed in the context of utilizing radiolabeled peptides targeted towards high affinity receptors expressed by transduced tumor cells. Transduction of tumor cells with adenovirus-polylysine-DNA conjugates containing the genes for IL-4 receptor and gastrin releasing peptide receptor (GRPr) resulted in the specific binding of $^{125}$I-labeled IL-4 and $^{125}$I-labeled bombesin, respectively. The present invention indicates that adenovirus-mediated gene transfer can induce radioligand binding to tumor-associated receptors in vitro and in vivo. These studies establish the rationale to translate this approach into the use of receptors and radiolabeled peptides and for the translation into clinical trials in the context of local/regional tumor targets.

Thus, in one embodiment of the methods of the present invention, there is provided a method of enhancing radiolabeled ligand localization to a tumor in an individual in need of such treatment, comprising the steps of: transducing said tumor with a gene encoding a membrane expressed protein unique to said tumor; and administering to said individual a radiolabeled ligand which specifically binds to said protein.

In another embodiment of the present invention, there is provided a method of treating a tumor cell in an individual in need of said treatment, comprising the steps of administering to said patient a transduced gene encoding a membrane expressed protein unique to said tumor; and treating said individual with a therapeutically effective dose of a radiolabeled ligand which specifically binds to said protein.

In yet another embodiment of the present invention, there is provided a method of increasing the amount of radiation received by a cell, comprising the steps of delivering to said cell a transduced gene encoding a membrane expressed protein unique to said cell; and contacting said cell with a pharmacologically effective dose of a radiolabeled ligand which specifically binds to said protein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows the immunostaining for CEA antigen expression in D54 MG human glioma cells transfected in vitro with AdCMVCEA or AdCMVLacZ at 1 PFU/cell or mock-infected. Cells were assayed 48 hours post-transfection. The photographs shown depict: (FIG. 3A) D54 MG cells/AdCMVCEA, (FIG. 3B) D54 MG cells/AdCMVLacZ, (FIG. 3C) D54 MG cells/mock infected. Pictures shown are of a representative field. 100× magnification.

FIG. 7A. (Magnification×100.) D54 MG tumor was transfected in vivo with 1 intratumoral injection of 1×10$^7$ PFU AdCMV-CEA and sectioned 2 days later. Strongest CEA staining is in a focal area of the tumor demarcated by long black arrows. FIG. 7B. (Magnification×200.) Staining of D54 MG tumor 13 days after transfection in vitro with 1 PFU AdCMVCEA, demonstrates scattered cells expressing CEA. Although some cells exhibit strong expression (long arrow) and other exhibit weak expression (short arrow), most cells do not exhibit expression of CEA. FIG. 7C. (Magnification× 200.) Focal staining of a D54 MG tumor trnasfected in vivo with 2 daily intratumoral injections of 1×10$^7$ PFU AdCM-VCEA and sectioned 2 days later. FIG. 7D. (Magnification× 100.) D54 MG tumor transduced with 3 daily intratumoral injections of 1×10$^7$ PFU AdCMVCEA and sectioned 2 days later stains weakly to moderately (short arrow) adjecent to dermal area with no staining (SA=skin appendage). FIG. 7E. (Magnification×200.) Additional focal staining was observed in another region of the same D54 MG tumor (represented by FIG. 7C) transfected in vivo with 2 daily intratumoral injections of 1×10$^7$ PFU AdCMVCEA and sectioned 2 days later. Short arrow indicates weak staining.

FIG. 21 shows the in vitro infection of human carcinoma cell lines with AdCMVGRPr. Binding results are shown in FIG. 21A for the human non-small cell lung carcinoma cell line A427, two human glioma cell lines D54MG and U251MG, and two human colon carcinoma cell lines LS174T and WiDr. Binding results are shown in FIG. 21B for the human ovarian carcinoma cell lines OVCAR-3, OV-4 and SKOV3.ip1. In FIGS. 21A and B, (⊟) represents uninfected cells and (□) represents BNR-11 cells incubated with [125I]-Tyr4-bombesin in the presence of excess unlabeled bombesin peptide. The bars are the mean percent added radioactivity bound± S.E.M. (n=2) from a representative experiment.

DETAILED DESCRIPTION OF THE INVENTION

Figure 1:
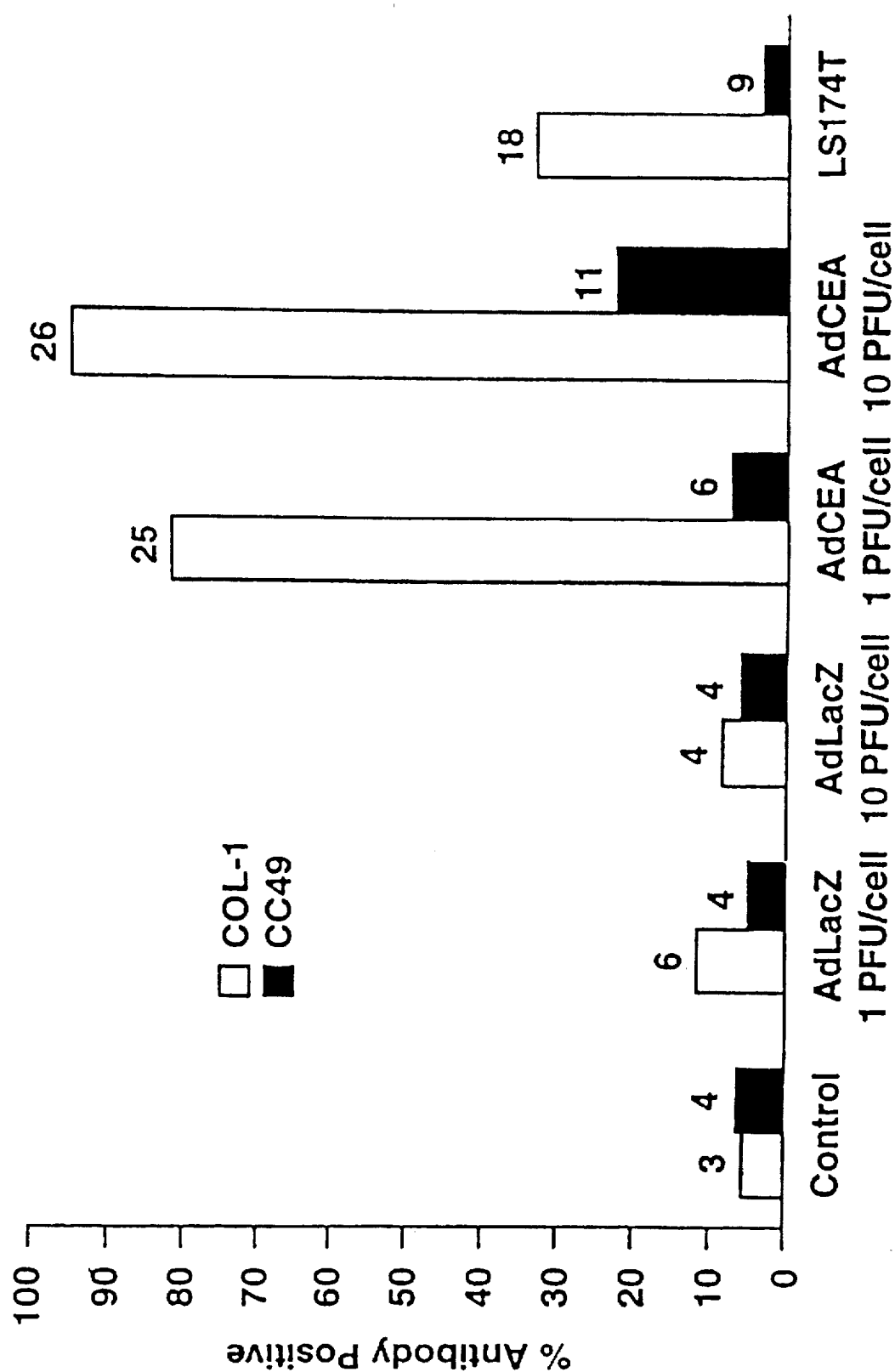
FIG. 1 shows the reactivity of MAbs COL-1 (reactive with CEA) or (CC49 reactive with the TAG-72 antigen) with D54 MG cells transduced with 1 or 10 PFU/cell of AdCMVCEA or AdCMVLacZ as determined by flow cytometry using fluorescein-conjugated goat anti-mouse IgG antibody. The mean percentage positive cells is depicted by the bars and the mean fluorescence for the populations is given above the bars. For comparison, CEA-expressing LS174T colon carcinoma cells were similarly immunostained and analyzed.
Figure 2A:
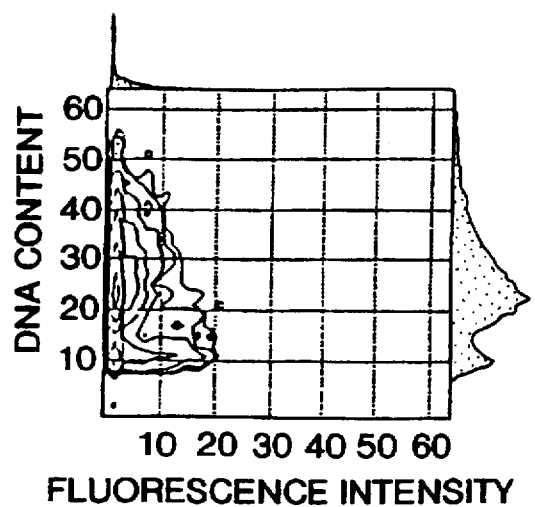
(FIG. 2A) uninfected D54 MG.
Figure 2B:
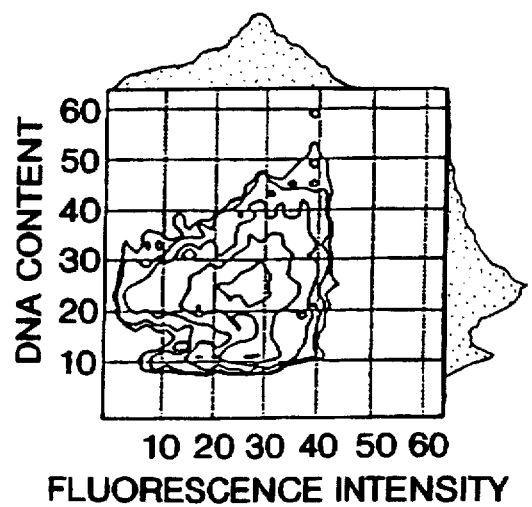
(FIG. 2B) AdCEA (1 PFU/cell) D54 MG.
Figure 2C:
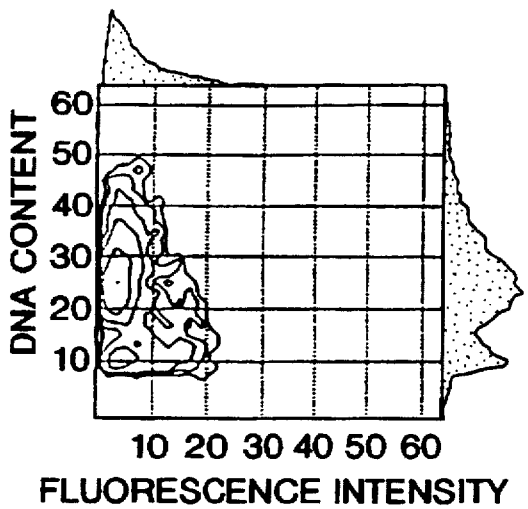
(FIG. 2C) AdLacZ (1 PFU/cell) D54 MG.
Figure 2D:
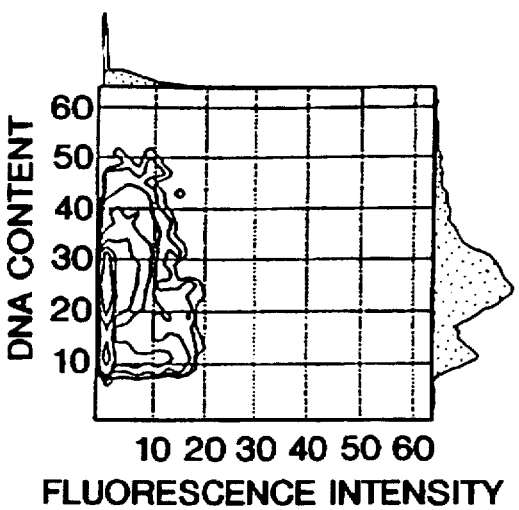
(FIG. 2D) AdCEA (1 PFU/cell D54 MG.
Figure 2E:
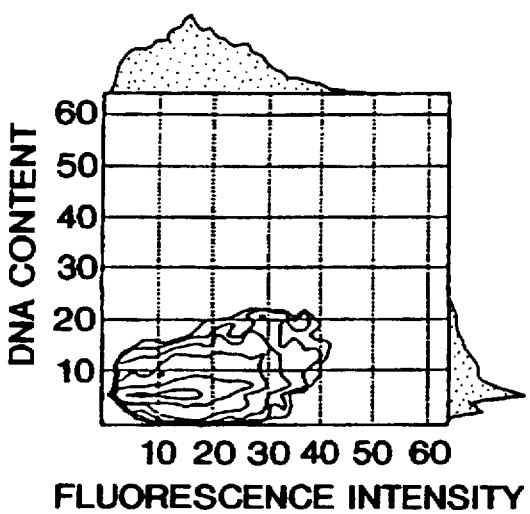
(FIGS. 2E and F) uninfected LS174T. MAb COL-1 was used in FIGS. 2A, 2B, 2C and 2E; MAb CC49 was used in FIGS. 2D and 2F.
Figure 2F:
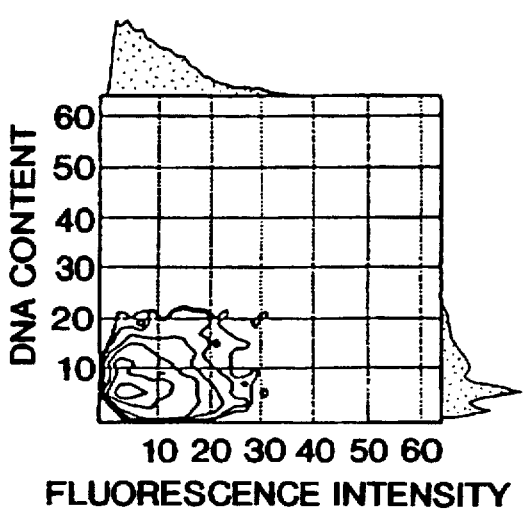
FIG. 2 shows the contour plots of DNA content (y-axis) and cell surface antigen expression (x-axis) in AdCMVCEA transduced D54 MG cells utilizing the anti-CEA COL-1 MAb or the TAG-72 CC49 MAb (negative control). D54 MG cells transfected with AdCMVLacZ were also analyzed as negative controls, and LS174T cells (constitutively express CEA and TAG-72) were positive controls. Cells which were analyzed were.

The present invention is directed to a method of enhancing radiolabeled ligand localization to a tumor in an individual in need of such treatment, comprising the steps of: transducing said tumor with a gene encoding a membrane expressed protein unique to said tumor; and administering to said individual a radiolabeled ligand which specifically binds to said protein.

In one embodiment of the present invention, the tumor is transduced by direct intratumor gene transfer in vivo. Representative examples of tumors which can usefully be transduced by this method of the present invention include colon tumors, lung tumors and glioma tumors.

In another embodiment of the present invention, the tumor is transduced by intraperitoneal gene transfer in vivo Representative examples of tumors which can usefully be transduced by this method of the present invention include intraperitoneal ovarian tumors and colon tumors.

In another embodiment of the present invention, the tumor is transduced by stereotactic direct gene transfer. Representative examples of tumors which can usefully be transduced by this method of the present invention include intracerebral gliomas.

In another embodiment of the present invention, the tumor is transduced by systemic gene transfer. Representative examples of tumors which can usefully be transduced by this method of the present invention include systemic colon tumors or lung tumors.

In the various embodiments taught by the present invention, the membrane expressed protein encoded by the transduced gene may generally be either an antigen or a receptor. Similarly, in the various embodiments taught by the present invention, the radiolabeled ligand which specifically binds to the protein may generally be monoclonal antibody or simply a peptide with sufficient specificity to the membrane expressed protein. Representative examples of useful antigens and the respective monoclonal antibody which binds to each antigen is detailed in Table V. Preferably, (1) the antigen is carcinoembryonic antigen and the radiolabeled ligand which specifically binds to this antigen is selected from the group consisting of MAb 25, MAb 35, BW494//32T84.66, MN-14 and NP-4; (2) the antigen is epidermal growth factor receptor and the radiolabeled ligand which specifically binds to this antigen is selected from the group consisting of monoclonal antibodies 225, 425, 528, L8A4, RG83852 and EGFR1; (3) the antigen is the estrogen receptor and the radiolabeled ligand which specifically binds to this antigen is anti-estriol-3-sulfate; (4) the antigen is TAG-72 and the radiolabeled ligand which specifically binds to this antigen is selected from the group consisting of monoclonal antibody CC49, monoclonal antibody B72.3 and monoclonal antibody CYT-103.

Representative examples of useful receptors and the respective radiolabeled ligand which binds to each receptor is detailed in Table VI. Using the techniques described herein, tumors may be transduced with naturally occuring receptors, i.e., receptors which naturally occur in that specific tumor or tumor may be transduced with heterologous receptors, i.e., receptors that don't normally exist in that particular tumor. Preferably, (1) the receptor is the epidermal growth factor receptor and said radiolabeled ligand is epidermal growth factor or transforming growth factor-alpha; (2) the receptor is the estrogen receptor and the radiolabeled ligand which specifically binds to this receptor is selected from the group consisting of tamoxifen, estradiol, estradiol derivatives, estrogen and fluoroalanine; (3) the receptor is the gastrin releasing peptide receptor and the radiolabeled ligand which specifically binds to said receptor is selected from the group consisting of bombesin, bombesin analogues and gastrin releasing peptide; (4) the receptor is the interleukin-4 receptor and the radiolabeled ligand which specifically binds to this receptor is interleukin-4; (5) the receptor is the somatostatin receptor and the radiolabeled ligand which specifically binds to this receptor is octreotide or other somatostatin analogues; and (6) the receptor is the vasoactive intestinal peptide receptor and the radiolabeled ligand which specifically binds to this receptor is vasoactive intestinal peptide. In one embodiment, the transducion is by adenoviral mediated gene transfer. Preferably, the radiolabel used in the methods of the present invention is selected from the group consisting of $^{123}$I, $^{125}$I, $^{131}$I, $^{32}$P, $^{64}$Cu, $^{67}$Cu, $^{211}$At, $^{177}$Lu, $^{90}$Y, $^{186}$Re, $^{212}$Pb and $^{212}$Bi, $^{47}$Sc, $^{105}$Rh, $^{109}$Pd, $^{153}$Sm, $^{188}$Re, $^{199}$Au, $^{211}$At, $^{213}$Bi.

In another embodiment of the present invention, a person having ordinary skill in this art is taught a method of treating a tumor cell in an individual in need of said treatment, comprising the steps of: administering to said patient a transduced gene encoding a membrane expressed protein unique to said tumor; and treating said individual with a therapeutically effective dose of a radiolabeled ligand which specifically binds to said protein so that radiation from said radiolabeled ligand is delivered to said tumor.

In another embodiment of the present invention, a person having ordinary skill in this art is taught a method of increasing the amount of radiation received by a cell, comprising the steps of: delivering to said cell a transduced gene encoding a membrane expressed protein unique to said cell; and contacting said cell with a pharmacologically effective dose of a radiolabeled ligand which specifically binds to said protein.

The physical and chemical properties of a radionuclide are important in its selection for radiotherapy. The type of particulate emission must be considered (36). The potent lethality of Auger and low-energy conversion electrons has been demonstrated (37–40). This effect can best be realized with intranuclear localization of the radionuclide, which does not generally occur with radiolabeled MoAbs, but may occur with certain membrane receptor-radioligand interactions. Of course, alpha particles have a high linear energy transfer (LET) effective in cell killing and a range of several cell diameters, 40–80 μm. The short ranges will accentuate inhomogeneous absorbed dose particularly when the radioligand deposition is inhomogeneous. They may have a role for therapy of micrometastases, leukemia, and intracavitary administration (193). Beta particles are less densely ionizing and have a range longer than alpha particle emitters so that the tumor distribution requirements are less restrictive. On the other hand, for micro-metastases, the absorbed fraction for higher energy beta particles (range>tumor size) is decreased, leading to a less favorable tumor absorbed dose. The gamma-ray energies and abundances are also important physical properties, because the presence of gamma rays offers the possibility of external imaging but also adds to the whole-body radiation dose.

These physical and chemical factors must then be viewed in light of available biological information (36,41). There is substantial variation in radioligand uptake, macro- and micro-distribution, kinetics and metabolism/catabolism depending on the particular radioligand, radioligand dose, the variability of antigen/receptor expression in the tumor, its size and stage, etc. (42–54). This may be due to cell type heterogeneity, heterogeneity of antigen/receptor expression, heterogenous vascularity and capillary permeability, elevated interstitial pressure, the binding site barrier, and spatial inaccessibility (14,36,42–55). The expected nonuniform distribution of radioligand discussed above reduces the attractiveness of short-ranged alpha-emitting radionuclides for solid tumor radiotherapy. A role for alpha emitters may be feasible in specific cases such as for micrometastases or intracavitary administration for some types of cancers, such as peritoneal injection for colorectal or ovarian carcinoma (36,56,57). The longer range of beta particles can still permit uniform tumor irradiation despite a marked heterogeneity of distribution of radioactivity within the tumor. It appears desirable to deliver ionizing radiation with a range of one to several millimeters in solid tumors, as from intermediate to high-energy beta particles.

Beta emitters offer a wide choice of candidates with a selection of particle ranges and chemical properties (36). The use of radionuclides with some gamma emission would allow diagnostic low-dose experiments to determine biodistribution prior to administering a therapeutic dose of the exact same preparation. Most therapeutic trials to date using radioimmunotherapy have utilized $^{131}$I, largely due to its ready availability at moderate cost, the ease of radioiodination techniques for proteins, and its long history of use in treating thyroid malignancy, rather than any careful analysis of its suitability for radioimmunotherapy. $^{131}$I has a physical half-life of 8.04 days, maximum beta energy of 0.8 MeV, average beta energy of 0.2 MeV, and is considered a medium-range beta emitter (mean range between 200 μm to 1 mm) with a maximum range of 1.5 mm in soft tissue. However, the yield of penetrating gamma radiation with $^{131}$I (average energy of 0.36 MeV) constitutes two-thirds of the total absorbed dose equivalent of this source in humans, resulting in higher total body doses away from the tumor volume thereby contributing to bone marrow toxicity. There is also a problem with dehalogenation producing a further loss in specific targeting, retention in tumor, and an increase in toxicity.

⁹⁰Yttrium is being studied as a radioimmunotherapy isotope (5,14,55,58–65) because of its favorable characteristics which include a 64 h half-life and an intermediate beta energy (2.3 MeV maximum). Since $^{90}$Y is unsuitable for quantitative imaging, many groups are utilizing $^{111}$In biodistribution data to predict dose for $^{90}$Y administrations (58,59). However, even though there are similarities in tumor uptake, blood clearance and normal tissue uptake, there may be substantial differences in retention and clearance from kidney, bone, and the reticuloendothelial system.

$^{186}$Rhenium has some attractive features for radioimmunotherapy. The energy contribution from gamma rays of $^{186}$Re is 137 keV with only 8.65% abundance, which should result in a lower dose to the whole-body than with $^{131}$I. The gamma radiation from $^{186}$Re is high enough to be efficiently used for external imaging. Finally, the x-rays from $^{186}$Re are low energy radiations (59–73 keV, 9.2% abundance) and there is only a small contribution from this source to the whole body dose. Even though imaging photons in $^{186}$Re can be used particularly at therapeutic dose levels (66,67) the "matched pair" approach using $^{99m}$Tc and $^{186}$Re (the former for imaging and the latter for therapy) is a very attractive option (36,67). These can both be attached to antibodies via similar chemistry (36,68) and generally produce similar biodistributions. Rhenium-186 requires a high flux reactor to achieve adequate specific activity.

Alpha particles and other heavy particles interact with matter producing dense trails of ionization. This effect, known in biology as high linear energy transfer (LET), produces a greater relative biological effectiveness (RBE) than low LET radiation, principally photons and electrons. The likelihood of an alpha particle passing through a cell and not damaging a critical structure is roughly 4 to 10 times lower than for low LET radiation (69,70). This is a zero order effect and means that the same level of tumor ablation can be achieved with lower radiation doses. This is important when considering the limited number of receptor sites in a tumor and other biologic factors that limit the dose that can be delivered via radiotherapy.

There are two additional important advantages of high LET radiation that are important for their use in radiotherapy. The first is the independence of cytotoxicity from the rate at which dose is delivered. The second advantage of high LET emitters is their ability to create ionization in the absence of oxygen (73). This is an important advantage of high LET radiation in treatment of tumors that have areas of hypoxia. The ability to kill cells in these regions with the same dose of radiation is an important advantage in therapy.

One of the disadvantages of high LET emitters for radiotherapy has been the limited selection of appropriate radionuclides. Given constraints on the half-life, photon emission and stability of daughter products, there are few candidate radionuclides for therapy. One of the most promising, Astatine-211, has the disadvantage of requiring a cyclotron that can accelerate He-4 ions in order to produce it. This, coupled with its 7.2 hour half-life, creates some serious problems in supply.

A generator system is available and capable of producing Lead-212 (76). Lead-212 has a 10.6 hour half-life and decays by beta emission to $^{212}$Bi. Bismuth-212 has a 1 hour half-life and decays by beta and alpha emission to stable $^{208}$Pb. This system combines some of the most attractive aspects of radionuclides for therapy. Lead-212 is produced from Radium-224 which has a 3.6 day half-life, on the order of Molybdenum-99. It can be shipped conveniently without experiencing serious decay losses. The $^{212}$Pb can be generated on site in a no-carrier-added form ideal for conjugating to small amounts of reagent, thus insuring high specific activity. The half-life is ideal for therapy, long enough to insure that localization can occur, but short enough to not present serious problems in redistribution in vivo. The availability of large quantities of the grandparent, Thorium-228, insures that several clinical sites could be supplied with material for Phase I and Phase II studies. In the event that commercial application appears promising, $^{228}$Th could be produced by a number of routes in adequate quantities.

The advantages of high LET radiation have been exploited by several groups who are investigating using alpha-emitting radionuclides for therapy (77–82). The short range of the alpha particle in vivo necessitates keeping the emission near the cell surface or inside the cell (83). Subsequently, studies by Zalutsky and co-workers have shown that an $^{211}$At-labeled antibody can be used to treat a meningioma successfully (79). While the $^{211}$At has been shown to successfully treat a solid tumor, the limited availability still poses a problem for clinical use. Gansow and co-workers have experimented extensively with chelate systems that could be used to radiolabel antibodies with $^{212}$Bi and its parent, $^{212}$Pb (84–87).

All of the following radionuclides may be used in the present invention, including $^{123}$I, $^{125}$I, $^{131}$I, $^{32}$P, $^{64}$Cu, $^{67}$Cu, $^{211}$At, $^{177}$Lu, $^{90}$Y, $^{186}$Re, $^{212}$Pb, and $^{212}$Bi.

Xenogeneic radiolabeled ligand peptides/high affinity membrane receptor systems is a novel genetic radio-isotope targeting strategy. Several receptor-ligand pairs have useful characteristics for incorporation into this novel therapeutic strategy, such as the murine gastrin-releasing peptide receptor (mGRP-R)-Bombesin/GRP. Useful characteristics of receptors of this class for the present application would be that they can be expressed at ectopic sites by gene transduction methods and that they exhibit high affinity binding with their ligand. In addition, it would be desirable if endogenous expression of the ligand occurred in a temporal or spatial pattern to minimize ectopic, non-tumor localization of the radioligand. One of the human counterparts of the amphibian bombesin peptides is the gastrin-releasing peptide (GRP). Battey et al. (91–93) reported the isolation and characterization of cDNA clones encoding the bombesin/GRP receptor. If expressed in heterologous cells, this receptor can confer high affinity binding of bombesin/GRP peptides.

The somatostatin receptor (SSTR)-Octreotide may also be used in the methods of the present invention. An advantage of using the somatostatin receptor (SSTR) as the target is that the somatostatin analogue octreotide is being used for radioimaging and radiotherapy (94–97). Somatostatin (SST) is a cyclic peptide consisting of 14 amino acids (98,99). The practical application of native SST as a radiopharmaceutical is limited by its short plasma half-life (minutes). Octapeptide SST analogues that have longer serum half-lives than SST have been described (100–102). The most characterized SST analogue, octreotide, can be labeled with several radionuclides including those that have been used in conventional RAIT such as $^{131}$I, $^{90}$Y and $^{186}$Re. At least four different subtypes of SSTR have been identified in human tissue and have been cloned (103–105). Octreotide binds with high affinity to the SSTR2. The SSTR2/octreotide system for the genetic induction of receptors has the potential to overcome the limitations of standard RAIT.

The murine IL-4 receptor may also be used in the methods of the present invention. The choice of a xenogeneic receptor useful for this strategy would be such that the induced receptor possessed high affinity binding for its ligand, possessed the capacity to be expressed at high levels in heterologous cells and exhibited no cross-reactivity with endogenous ligand. One compound which achieves these criteria is the murine IL-4 receptor. Park et al. have cloned this receptor cDNA and expressed it in heterologous COS-7 cells (106). Expression of the IL-4r clone in COS-7 cells resulted in an IL-4 binding protein indistinguishable from the natural receptor at its normal levels. The binding of $^{125}$I-IL-4 to these transduced cells exhibited a $K_a$ of $10^9$–$10^{10}$ $M^{-1}$. Importantly, the murine ligand does not exhibit binding to the human receptor while the human IL-4 does not exhibit binding to the murine receptor. Thus, the murine IL-4 receptor meets the above criteria for a useful xenogeneic receptor. Murine IL-4 is a glycoprotein with an approximate molecular weight of 19 kD (107).

There are animal models available for evaluation of targeted radiotherapy. A large range of human tumor xenograft systems have been used to analyze radioligand localization and therapy in pre-clinical animal models (reviewed in 5, 7–9). Human colorectal, leukemia, lymphoma, ovarian, hepatoma, breast, lung, bladder, kidney, neuroblastoma, cervical, melanoma, and brain tumor cell lines implanted subcutaneously in nude mice for such studies (5, 14, 55, 58, 108–135) have been used extensively. Since a major effect of the present invention relates to direct intra-tumor injection of genetic constructs to induce tumor cell membrane receptor expression, the clinical translation would require a tumor type which rarely metastasizes but kills due to progressive local tumor growth. Human glioblastomas fit this criteria and are the subject of a variety of gene therapy approaches dependent on local direct gene transfer techniques (136–138).

Thus, in one embodiment, a method of the present invention to carry out the radioligand localization and therapy studies can be performed in four different contexts: (1) colon, lung, head and neck, hepatic, mesothelioma, and glioma tumors that will undergo direct intratumor gene transfer in vivo followed by radioligand therapy; (2) intraperitoneal ovarian and colon tumors that will undergo intraperitoneal gene transfer in vivo followed by radioligand therapy; (3) intracerebral glioma tumors which will undergo stereotactic direct gene transfer followed by radioligand therapy. Further, a person having ordinary skill in this art would be able to utilize the methods of the present invention in the context of targeting vector expressing receptor cDNA; and (4) systemic colon, breast, brain, ovarian, bladder, pancreas, melanoma, gastric, leukemia, lymphoma and lung tumors that will undergo systemic gene transfer followed by radioligand therapy. This strategy will allow the developmental efforts of radioligand design and analysis to take place in a relatively simple in vivo system with progression to more complex models which better reflect the reality of human cancer.

The following examples are given for the purpose of illustrating various embodiments of the invention and are not meant to limit the present invention in any fashion.

EXAMPLE 1

Recombinant Adenoviruses Encoding Reporter Genes

Recombinant adenoviral vectors encoding reporter genes were used to evaluate gene transfer efficiency in HeLa and D54 MG cells. AdCMVLuc and AdCMVLacZ are E1A/B deleted, replication-incompetent adenoviral vectors previously described (139). AdCMVLuc encodes the firefly luciferase reporter gene under the control of the human cytomegalovirus (CMV) promoter/enhancer (provided by R. Gerard, University of Texas-Southwestern Medical Center, Dallas, Tex.). AdCMVLacZ encodes the reporter gene E. coli β-galactosidase (LacZ) under the control of the CMV promoter/enhancer (provided by R. Gerard).

EXAMPLE 2

Analysis of Reporter Gene Expression

Following adenoviral vector transduction, cells were analyzed for expression of the encoded reporter genes to assess the relative efficiency of gene transfer. For studies of relative levels of transducibility, cells were harvested 48 hours post-transduction, lysed, and analyzed for luciferase expression as described by the manufacturer (Promega Luciferase Assay System, Madison, Wis.). Briefly, lysates from transfected cells were obtained after removal of the tissue culture media and adding 150 μl of 1X cell culture lysis reagent to each well of cells. Cells were lysed at room temperature for 10–15 minutes, and cellular debris removed by centrifugation at 13,000×g for 3 minutes. The cell extract (20 μl) was then added to 100 μl of luciferase assay reagent and analyzed for emitted light in a Lumat LB9501 luminometer (Berthold Systems Inc., Aliquipa, Pa.).

LacZ reporter gene expression was also utilized to examine transduction frequency. For this analysis, cells infected with adenovirus encolding the LacZ reporter gene were harvested 48 hours post-transduction and analyzed by FACS (FACSort, Becton-Dickinson, Mountain View, Calif.). For FACS analysis $1\times10^7$ cells were trypsinized and resuspended in 1 ml of staining media (PBS containing 10 mM HEPES and 4% FBS). Aliquots containing $10^6$ cells were placed into a 6 ml FACS tube (Falcon, Franklin Lakes, N.J.) and warmed at 37° C. for 10 min. Prewarmed 2 mM fluorescein-di-galactosidase (100 μl) was added and the cells incubated at 37° C. for one min followed by the addition of 1 ml of cold staining media. Cells were kept on ice and in the dark until FACS was completed.

EXAMPLE 3

Construction of a Recombinant Adenoviral Vector Encoding the Human Carcinoembryonic Antigen cDNA An adenovirus expressing the human CEA cDNA was prepared employing standard techniques of in vivo homologous recombination (140). First, the human CEA cDNA (provided by J. Schlom, National Cancer Institute, Bethesda, Md.) was cloned into a corresponding site within the polylinker of the adenoviral shuttle vector pACCMVpLpARS(+) (provided by R. Gerard). This plasmid contains the human CMV early promoter/enhancer and SV40 polyadenylation signals controlling expression of the encoded cDNA. The resulting recombinant adenovirus shuttle plasmid, pACCEA, was employed to derive an E1A-deleted, replication defective recombinant adenovirus. Briefly, the shuttle plasmid plus the adenoviral packaging plasmid pJM17 (provided by F. Graham) were co-transfected into the E1A transcomplementing cell line 293 using the commercial cationic liposome vector DOTAP (Boehringer-Mannheim, Mannheim, Germany). Transfected cells were maintained until the onset of cellular cytopathic effects. The newly generated recombinant adenovirus was then plaque purified by a standard method (140). Confirmation of recombinant adenoviral identity was achieved by polymerase chain reaction utilizing primers specific for the CMV promoter and the CEA cDNA construct (141). Large scale preparation of the CEA encoding virus, AdCMVCEA, was accomplished and purified virus titered by plaque assay techniques for direct determination of viral PFU employing 293 cells as the target.

EXAMPLE 4

In Vitro Transduction Employing the CEA- Encoding Recombinant Adenovirus AdCMVCEA The D54 MG human glioma cells were initially seeded at $2.5 \times 10^6$ cells per T75 flask. When cells reached approximately 80% confluency, they were infected with either the AdCMVCEA adenoviral vector at varying particle numbers ranging from 1–1,000 PFU/cell or, as a control, AdCMV-LacZ vector at either 1 or 10 PFU/cell. Two-days post-injection, cells were analyzed for CEA expression via an indirect immunofluorescence assay, a radiolabeled binding assay, and by immunohistochemistry, as described below. As a positive control, the LS174T human adenocarcinoma, known to constituitively express CEA, was employed.

EXAMPLE 5

Monoclonal Antibodies

Intact mouse MAb COL-1, of the IGg2a subclass, reactive with CEA expressed on human adenocarcinomas (142) and intact mouse MAb CC49 (IgG1) reactive with TAG-72 antigen expressed on selected human adenocarcinomas (143) were generously provided by J. Schlom (National Cancer Institute, Bethesda, Md.).

EXAMPLE 6

Flow Cytometry Analysis

Flow cytometric analyses were carried out 48 hours after genetic transduction of D54 MG cells with AdCMVCEA or AdCMVLacZ using unlabeled anti-CEA MAb COL-1 or MAb CC49 (negative control). Briefly, cells growing in monolayer culture were detached with 4 mM EDTA, 0.05% KCl in PBS (pH 7.2), washed in cold 0.1% BSA/PBS by centrifugation (300×g, 5 min), resuspended in PBS and counted using a hemacytometer. Cells were aliquoted ($4 \times 10^6$/tube), washed once with cold PBS/EDTA/0.1% sodium azide, and 50 µl of COL-1 or CC49 (25 µg/ml in PBS+2% FBS), were added to appropriate tubes, and incubated (4° C., 2 hours) with agitation every 30 minutes. The cells were then washed with PBS/EDTA/sodium azide and 50 µl of fluorescein-labeled goat anti-mouse IgG (Southern Biotechnology Associates, Inc., Birmingham, Ala.) was added to each tube. After incubation (1 h, 4° C., in the dark), cells were washed with PBS/EDTA/sodium azide and resuspended in 1 ml of the same. One ml of cold 70% EtOH was added to each tube with gentle mixing and cells were fixed (overnight, 4° C., in the dark). EtOH/PBS was decanted following centrifugation and 250 µl of 50 µg/ml propidium iodide (Boehringer Mannheim Corp., Indianapolis, Ind.) was added to each tube and incubated (1 hour, 4° C.) with agitation at 30 minutes. Cells were then washed, postfixed in 1 ml of 2% fresh paraformaldehyde and analyzed using a FACScan (Becton-Dickinson, Mountain View, Calif.) set up for 2-color analysis (UAB Flow Cytometry Core) after excitation at 488 nm. Under these conditions, green fluorescence (530 µm±21 nm) indicates membrane-associated CEA expression and red fluorescence (560 nm) is due to intercalation of propidium iodide into cellular DNA. Contour plots were generated for $10^4$ events representing appropriate-sized single cells selected from forward angle and side scatter dot plots. Using negative control antibody (CC49) samples, a gate was established on the horizontal axis that included 95% of events designated as negative for green immunofluorescence. By definition, cells with green fluorescence intensity greater than the gate set-point (to right of gate) were designated as positive. Gate set-point for propidium iodide (red) fluorescence on the vertical axis was arbitrarily set for the same (negative control) population at the midpoint of the nadir between the lower ($G_0/G_1$) and higher ($S/G_2/M$) peaks of red fluorescence intensity. These gate settings were used to analyze all populations of cells stained from the same experiment. Results are expressed as mean percentage of positive staining cells and mean linear fluorescence.

EXAMPLE 7

Radiolabeling and Characterization of Labeled Antibodies

Purified COL-1 and CC49 antibody preparations were labeled with $^{125}I$ or $^{131}I$ (New England Nuclear, N. Billerica, Mass.) using the Iodo-Gen method (144) as described previously (145). Free radioiodine was removed by passage of the labeled preparations over a Sephadex G25 column (PD-10, Pharmacia, Piscataway, N.J.). Specific activities of radiolabeled preparations were determined. Immunoreactivity of radiolabeled antibody preparations was measured using a live cell-binding assay with LS174T cells for COL-1 and SW1116 cells prepared from tumor xenografts for CC49 using the Lindmo method as described elsewhere (146,147).

EXAMPLE 8

Binding Activity of Radiolabeled Antibodies

A radiolabeled antibody binding assay was performed to analyze CEA cell surface expression. Binding activity of $^{125}I$-labeled COL-1 or CC49 antibody preparations were measured using an in vitro live cell-binding assay. AdCMVCEA or AdCMVLacZ transfected D54 MG human glioma cells were harvested using 4 mM EDTA, 0.05% KCl in PBS, pH 7.2 and resuspended in cold PBS, pH 7.2, at $1 \times 10^7$ cells/ml. Cells were aliquoted in duplicate or quadruplicate ($1 \times 10^6$ cells/tube). Radiolabeled antibodies (200 ng, $2 \times 10^5$ cpm) were added and incubated (room temp, 1 hour) with shaking. Cells were washed with 4 ml of PBS and cell-associated radioactivity was determined in a well-type gamma counter (Micromedic 4/200 Plus, ICN, Huntsville, Ala.). Cell-associated radioactivity was calculated as molecules of COL-1 or CC49 bound on the basis of Avogadro's number and the $^{125}I$-labeled COL-1 or CC49 specific activity and molecular weight. Nonspecific binding of radiolabeled antibodies was measured in the presence of 10 µg of unlabeled antibodies. Binding to non-transduced D54 MG cells as a control was also measured.

EXAMPLE 9

Immunohistochemistry Analysis of CEA Expression

To characterize CEA expression further, AdCMVCEA transduced D54 MG cells (1 PFU/cell) maintained in culture were immunostained with the anti-CEA COL-1 MAb using a streptavidin-peroxidase method as previously described (148–150) except that the secondary detection system was obtained from Biogenex (San Ramon, Calif.). Bound antibody was detected with a biotinylated anti-mouse IgG secondary antibody and streptavidin-peroxidase complex using diaminobenzidine tetrahydrochloride as the substrate to yield a brown, insoluble precipitate. Counterstaining was performed with Mayer's aqueous hematoxylin. For comparison, D54 MG cells either transduced with AdCMVLacZ or mock infected were immunostained as negative controls.

Following removal, the tumors were bisected and half of the tumor was fixed in neutral buffered formalin for 24 hours. After fixation the tissue was processed to paraffin blocks in a Shandon Citadel 2000 Tissue Processor using a standard protocol for rodent tissues and the tissues were embedded in paraffin blocks. Four micron paraffin sections were cut and heat attached to Superfrost Plus treated microscope slides (Fisher Scientific, Norcross, Ga.) at 58° C. for 1 hour. The slides were deparaffinized in xylene and rehydrated through graded ethanols to tris buffer (50 mM Tris, 140 mM NaCl, 0.01% Triton X100, pH 7.6).

An area around the tissue section was demarcated with a PAP pen and the slides were placed on an Optimax Automated Cell Stainer (Biogenex, San Ramon, Calif.). The slides were incubated at room temperature sequentially, with 3% aqueous $H_2O_2$ for 3 minutes to quench endogenous peroxidase activity, 10% casein for 10 minutes to block non-specific activity, antibody or serum delete for 1 hour, biotinylated anti-mouse antibody for 20 minutes, and streptavidin peroxidase for 20 minutes. DAB (3,3' diaminobenzidine) was applied for 7 minutes and was precipitated as a brown insoluble complex by the peroxidase. The slides were washed with Tris buffer between each step. The casein (HK085-4K), StrAviGen super sensitive mouse HRP kit (ZP000-UM) and the DAB (HK153-5K) were obtained from Biogenex. The slides were removed from the Optimax stainer and lightly counterstained with hematoxylin for 1 minute. They were then dehydrated through alcohols to xylene and coverslipped with permount.

EXAMPLE 10

Mice

Athymic nude female nu/nu with a BALB/c background, 4–5 weeks old, were obtained from the National Cancer Institute Frederick Research Laboratory (Frederick, Md.). Mice were kept under sterile conditions in a laminar flow room in cages with filter bonnets and were fed sterilized mouse diet and sterilized tap water. The procedures used minimized discomfort, distress, and pain to the animals.

EXAMPLE 11

In Situ Tumor Transduction Employing the CEA-Encoding Recombinant Adenovirus AdCMVCEA In situ experiments were designed to evaluate transduction efficiency of D54 MG xenografts to express detectable levels of CEA. Initial experiments involved immunostaining transduced xenografts to assess unlabeled COL-1 binding. Briefly, D54 MG cells were transfected in vitro with either AdCMVCEA or AdCMVLacZ at 1 PFU/cell. After 2 days in culture, these cells were subcutaneously injected into the flanks of groups of athymic nude mice at $2 \times 10^7$ live cells per animal. Immunohistochemical analysis of this group of tumors was performed 13 days after tumor cell injection.

CEA expression was next evaluated in D54 MG cells transduced in situ by direct intratumoral injection (over 1–3 consecutive days) with AdCMVCEA and analyzed immunohistochemically. D54 MG xenografts were established in athymic nude mice at $2 \times 10^7$ live cells per animal. After tumors had reached diameters of approximately 5–10 mm, transduction in situ was performed by injecting either AdCMVCEA or AdCMVLacZ directly into the tumor masses (28G needle, 50 ml/tumor) at $1 \times 10^7$ PFU. Immunohistochemical analysis of this group of tumors was performed 2 days after the last intratumoral injection.

To demonstrate that one could augment radiolabeled antibody targeting in vivo, D54 MG cells were initially transduced in vitro with AdCMVCEA or AdCMVLacZ at 1 PFU/cell. After 2 days in culture, transfected D54 MG cells were established as xenografts in athymic nude mice as previously described. After 11–15 days, when xenografts were 5–10 mm in diameter, additional AdCMVCEA ($1 \times 10^9$ PFU) or AdCMVLacZ ($1 \times 10^9$ PFU) were injected intratumorally (28G needle, 50 ml/tumor) on 1 or 2 consecutive days. One day after the last in situ administration of AdCMVCEA or AdCMVLacZ, animals were injected intraperitoneally with $^{131}$I-labeled COL-1 antibody and biodistribution determined as described below. In one experiment, non-transfected D54 MG cells were injected subcutaneously into nude mice and the xenografts received a single in situ injection of $2 \times 10^7$ PFU of either AdCMVCEA or AdCMVLacZ 2 days before the injection of $^{131}$I-labeled COL-1. Control studies were performed with LS174T xenografts that endogenously express CEA (4,151,152). Non-transduced LS174T cells ($1$–$1.5 \times 10^7$) were injected subcutaneously into the flank of nude mice. When these tumors were approximately 5–10 mm in diameter (8–9 days post-induction), animals received an intraperitoneal injection of $^{131}$I-labeled COL-1 as described below. In another experiment, non-transfected D54MG cells were injected subcutaneously into nude mice and xenografts received two in situ injections of $1 \times 10^9$ PFU of AdCMVCEA 1 and 2 days before the injection of $^{131}$I-labeled COL-1.

EXAMPLE 12

Biodistribution of $^{131}$I-labeled COL-1 Antibody

In vivo imaging of $^{131}$I-labeled COL-1 antibody was used to estimate the efficacy of radiolabeled antibody targeting to tumor accomplished via genetic transduction of CEA cell surface expression. In vivo tissue distribution of $^{131}$I-labeled COL-1 antibody in athymic nude mice bearing subcutaneous D54 MG-AdCMVCEA transduced tumors was undertaken to assess the extent of tumor and normal tissue localization. As a specificity control, athymic nude mice bearing AdCMVLacZ transduced D54 MG tumors were used. Athymic nude mice bearing xenografts of the LS174T human colon cancer cell line served as a positive control. Radiolabeled anti-CEA antibodies have been previously shown to localize in LS174T tumor xenografts (4,151,153). For this analysis, 100 or 300 μCi of $^{131}$I-labeled COL-1 antibody were injected intraperitoneally into groups of mice bearing established tumors of 5–10 mm in diameter. Thyroid uptake was blocked by adding a saturated solution of potassium iodide to their drinking water. Whole body scans of anesthetized (100 mg/kg sodium pentobarbital) mice were obtained 5 days after radiolabeled antibody injection using a large field-of-view Sopha DSX camera (Sopha Medical, Columbia, Md.) fitted with a 4 mm pinhole collimator interfaced to a microcomputer. Immediately after imaging, mice were exsanguinated, killed and necropsied. Samples of liver, kidney, spleen, lung, small intestine, femur, skin, muscle, tumor, and blood were blotted dry, weighed, and the radioactivity assayed in a well-type gamma counter (Minaxi-gamma 5000 series, Packard, Chicago, Ill.) to determine the tissue distribution of $^{131}$I-labeled COL-1. Results of radiolabeled antibody biodistribution are expressed as mean±SD % ID/g of tissue and tumor/normal tissue (T/NT) uptake ratios.

EXAMPLE 13

Statistical Analyses

The difference in the number of molecules of $^{125}$I-labeled COL-1 bound to AdCMVCEA transduced D54 MG cells and LS174T cells in vitro was analyzed using a t-test. Biodistribution data of % ID/g of tissue and T/NT uptake ratios were analyzed through two-way analysis of variance (154). Differences among experiments and among tissues were tested together with the interaction effects. Differences of % ID/g of tissue among the seven experiments were also tested separately through one-way analysis of variance for blood and tumor. For the T/NT uptake ratio data, tests were performed to compare differences among three experimental groups for each of the nine tissues and to compare the differences among the nine tissues for each of three experimental groups.

EXAMPLE 14

Adenoviral-Mediated Transduction of Human Glioma Cells

As an initial screen for vector efficacy, target cells infected with the firefly luciferase encoding adenovirus (AdCMVLuc) were evaluated for gene expression 48 hour post-transduction. D54 MG human glioma cells were found to be highly transducible, expressing high levels of luciferase when compared to uninfected control cells. Of note, the levels of expression were comparable to those observed with transduction of HeLa, a cervical carcinoma cell line known to be highly transducible by recombinant adenoviral vectors (data not shown).

To further validate the transducibility of D54 MG cells, an adenoviral vector encoding the β-galactosidase reporter gene was utilized to quantitate transduction frequency. Following transduction with the LacZ encoding adenoviral vector AdCMVLacZ, cells were harvested at 48 hour and examined for *E. coli* β-galactosidase expression by FACS analysis. These studies confirmed high efficiency transduction in D54 MG cells, with a transduction frequency of 100% observed. HeLa cells were used as a positive control cell line as they have previously demonstrated a transduction frequency of greater than 90% when employing adenoviral vectors. Thus, D54 MG human glioma cells were successfully transduced at a high efficiency with recombinant adenoviral vectors.

EXAMPLE 15

In Vitro Transduction Employing the CEA-Encoding Recombinant Adenovirus AdCMVCEA The extent to which D54 MG cells could be induced by adenoviral mediated gene transfer to express cell surface CEA was determined by flow cytometry. D54 MG cells were transfected with 1, 10, 100, or 1,000 PFU/cell of AdCMV-CEA. D54 MG cells transfected with AdCMVLacZ at 1 or 10 PFU/cell served as negative controls. Two-days post-transfection cell membrane-associated CEA was assayed with anti-CEA MAb COL-1 or with CC49, a negative control antibody. The LS174T human adenocarcinoma cells, known to constitutively express CEA, were utilized as a positive control cell line.

As shown in FIG. 1, there was a considerable increase in CEA positive D54 MG cells following AdCMVCEA transduction. Compared with the AdCMVLacZ transduced cells which were 5–11% positive for CEA by FACS, 82–95% of D54 MG cells infected with the AdCMVCEA construct were strongly positive even at the lowest multiplicity of infections (MOI) used (1 PFU/cell). Lower MOIs were not studied. At the lower viral particle numbers (e.g., 1 PFU/cell), cell viability remained high (>90%, data not shown) but as the MOI was increased to 10 PFU/cell, cell viabilities began to fall (<90%). Loss of cell viability perturbed the capacity to perceive any cell cycle shifts, since the dead cells appeared to have a lower DNA content and masked the $G_0/G_1$ population. However, in comparison to untransfected cells, there was not a significant shift in the $G_0/G_1$ and $S/G_2/M$ populations of cells transfected at the lower viral particle numbers. This nonspecific toxicity was also responsible for a small increase in CC49 positive cells. In comparison with the native expression of CEA on the human colon carcinoma cell line LS174T, AdCMVCEA transduced glioma cells expressed a higher level of CEA (mean fluorescence intensity=24.9 vs. 17.6 for LS174T, FIG. 2) and a greater proportion of the glioma cell population (81.8%) was judged positive compared with the LS174T cells (32.8%).

Carcinoembryonic antigen expression was further demonstrated by immunohistochemistry of AdCMVCEA transduced D54 MG cells (1 PFU/cell) maintained in culture which showed a strong specific reaction for the MAb COL-1 (FIG. 3). By comparison, D54 MG cells transduced with AdCMVLacZ (1 PFU/cell) or mock infected showed no specific reaction with COL-1 MAb. Thus, considerable levels of CEA expression may be induced on the cell surface of D54 MG cells through adenoviral mediated gene transfer.

EXAMPLE 16

Radiolabeling and Characterization of Labeled Antibodies

Radiolabeled anti-CEA antibodies that could be used to define intratumoral localization in a glioma model system were generated in vitro. Aliquots (500 µg) of purified COL-1 and CC49 antibodies were labeled with 1 mCi $^{125}$I with an average labeling efficiency of 70% and an average specific activity of 1 mCi/mg. The COL-1 antibody (1 mg) was also labeled with 10 mCi $^{131}$I with a labeling efficiency >90% and a specific activity of 6.6 mCi/mg. Free $^{125}$I or $^{131}$I was removed by passage of the labeled preparations over a Sephadex G-25 column. High pressure liquid chromatography showed <1% free $^{125}$I or $^{131}$I in the purified preparations. Immunoreactivity of the radiolabeled antibody preparations was greater than 90%.

EXAMPLE 17

Binding Activity of Radiolabeled Antibodies

Figure 4:
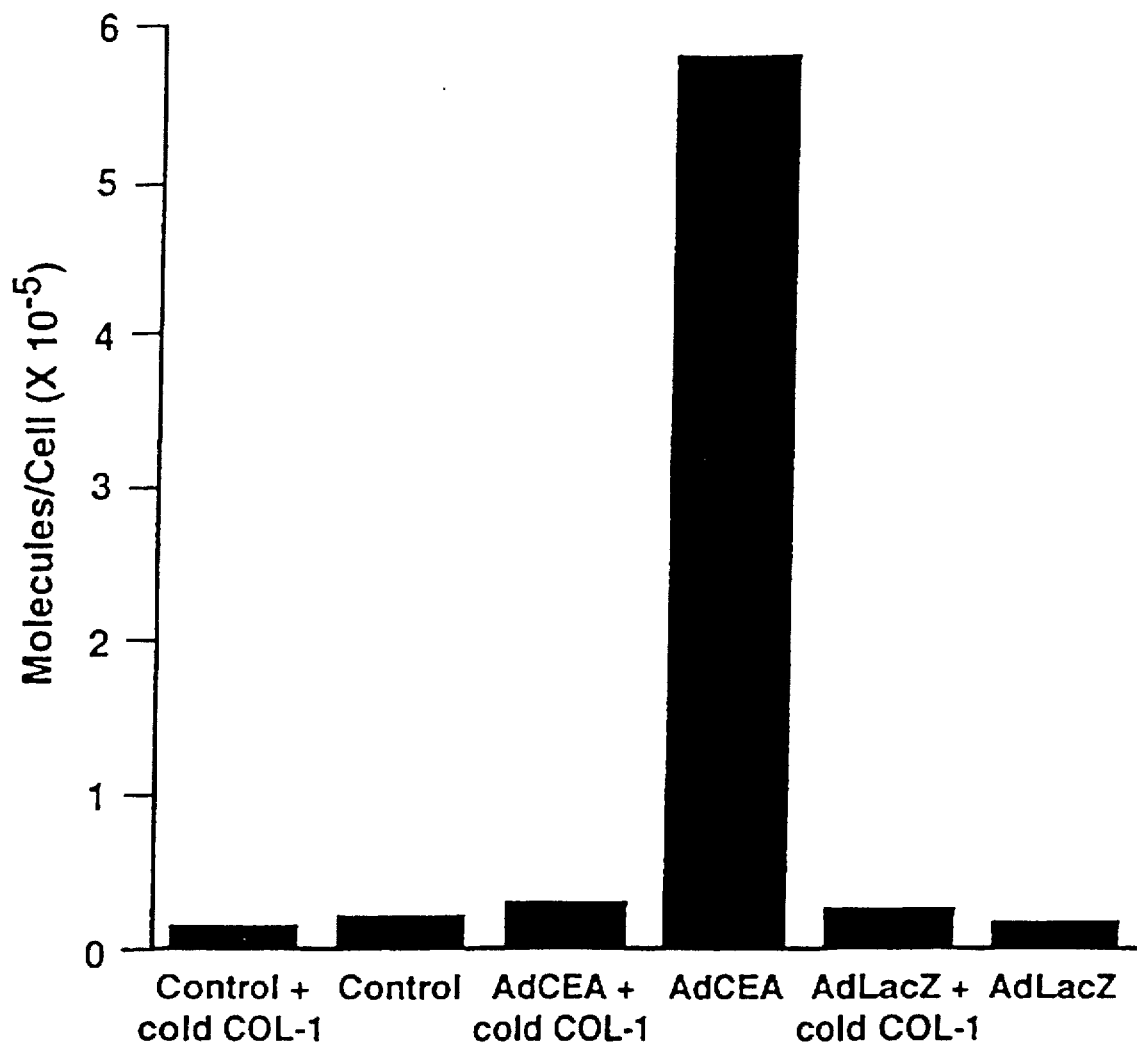
FIG. 4 shows the analysis of binding activity of $^{125}$I-labeled COL-1 MAb to AdCMVCEA transduced D54 MG cells. D54 MG cells were transfected with 1 PFU-cell and assayed 48 hours post-transfection. Both control virus (AdCMVLacZ) and control antibody (CC49) as well as non-transduced D54 MG cells were analyzed in comparison. The histograms depict the molecules of COL-1 bound/cell for a representative experiment run in duplicate. Nonspecific binding of $^{125}$I-labeled COL-1 antibody was measured in the presence of excess unlabeled COL-1 antibody.
Figure 5:
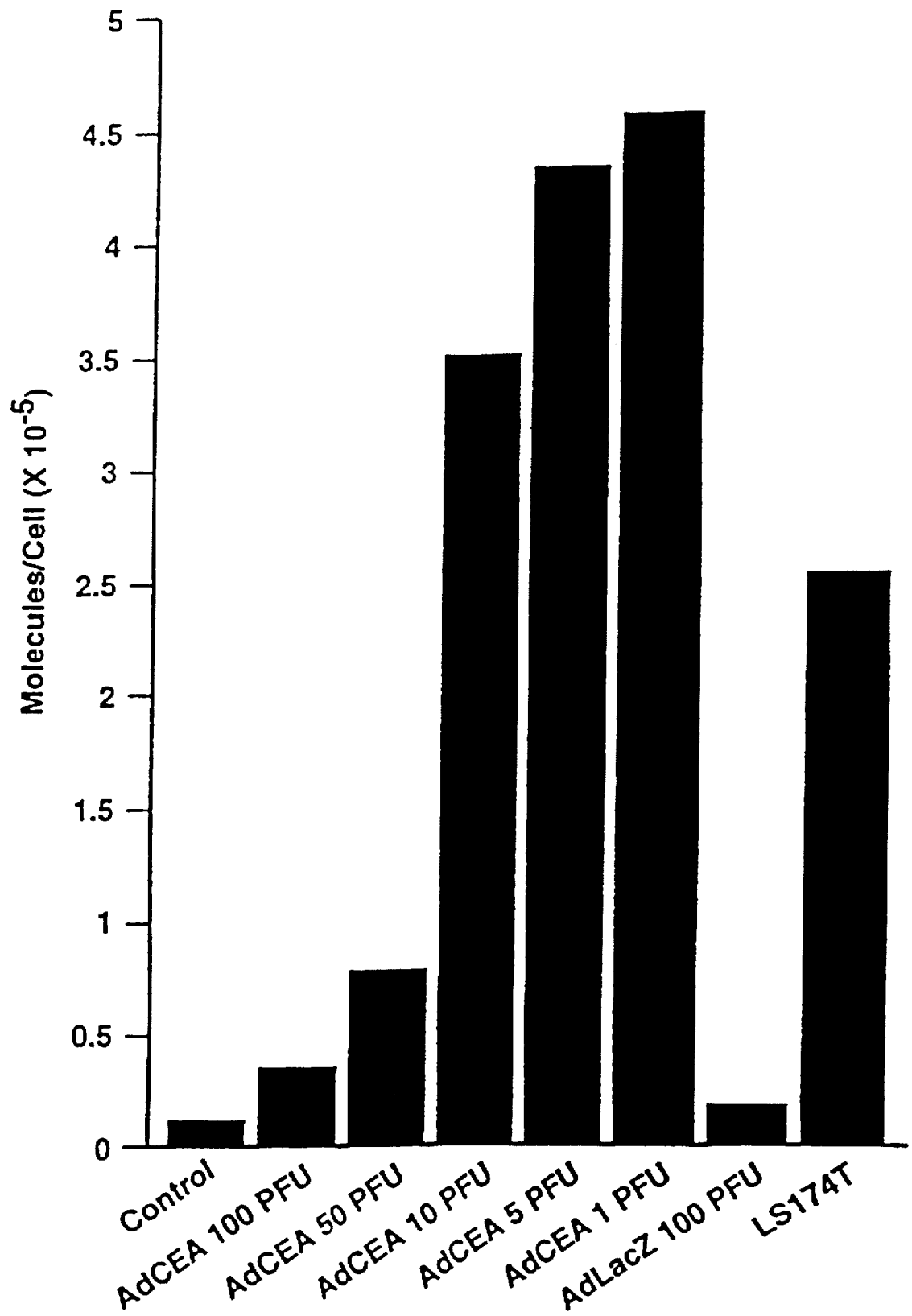
FIG. 5 shows the analysis of binding activity of $^{125}$I-labeled COL-1 MAb to D54 MG cells transfected with different particle numbers ranging from 1 to 100 PFU/cell. Non-transduced D54 MG cells as well as LS174T cells constitutively expressing CEA were analyzed in comparison. The histograms depict molecules of COL-1 bound/cell in duplicate samples. Nonspecific binding of $^{125}$I-labeled COL-1 antibody was measured in the presence of excess unlabeled COL-1 antibody.

Experiments were then conducted using an in vitro live cell radiolabeled antibody binding assay to quantify the level of CEA expression in AdCMVCEA transduced D54 MG cells. These results indicated high binding efficiency of $^{125}$I-labeled COL-1 to D54 MG cells that had been transduced to express CEA (FIG. 4). The number of molecules of CEA expressed on the cell surface membrane was calculated to be $5.8 \times 10^5$ molecules/cell. Unlabeled COL-1 antibody inhibited $^{125}$I-labeled COL-1 antibody binding to D54 MG cells transfected with AdCMVCEA to the level of nonspecific background binding (FIG. 4). Low background binding was seen with $^{125}$I-labeled CC49 and in the non-transfected D54 MG and AdCMVLacZ transfected D54 MG controls. In addition, the efficiency of radiolabeled COL-1 binding to AdCMVCEA transduced D54 MG cells was evaluated at 1, 5, 10, 50, and 100 PFU/cell. D54 MG cells transduced with AdCMVLacZ were used as negative controls and these samples were compared to LS174T human colon adenocarcinoma cells known to constitutively express CEA. Optimal expression of CEA, as measured by radiolabeled binding, was seen in D54 MG cells transfected with either 1 or 5 PFU/cell (FIG. 5). Furthermore, the number of molecules of CEA expressed on the cell surface of transfected D54 MG cells from six experiments with 1 PFU/cell at 48 hours post-transfection ($4.7\pm0.5\times10^5$, n=20) was considerably higher than in the CEA positive LS174T cells ($2.7\pm0.5\times10^5$, n=10) (P<0.01), confirming the earlier FACS results.

Figure 6:
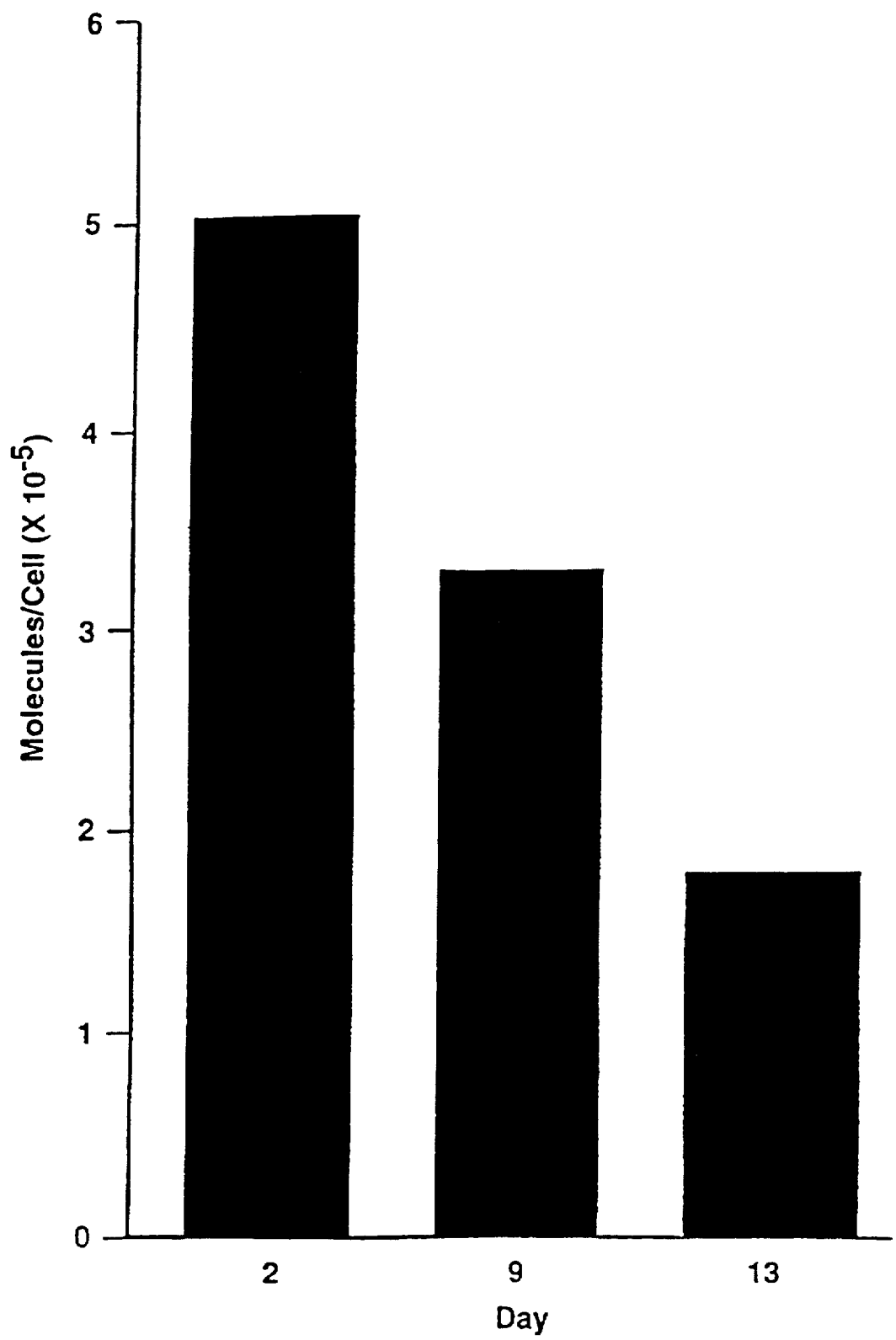
FIG. 6 shows the analysis of binding activity of $^{125}$I-labeled COL-1 MAb to AdCMVCEA transduced D54 MG cells assayed at varying days post-transfection. The histogram depicts the molecules of COL-1 bound/cell at 2, 9, and 13 days post-transfection in duplicate samples.

Since recombinant adenoviral infection is known to allow for only transient levels of heterologous gene expression (4), the persistence of cell surface CEA expression in AdCMV-CEA transduced D54 MG cells was determined. Radiolabeled binding assays were performed at 2, 9, and 13 days post-transfection with AdCMVCEA at 1 PFU/cell. $^{131}$I-labeled COL-1 binding to CEA transduced cells was found to be $5.1\times10^5$ molecules/cell 2 days post-transfection decreasing 3-fold to $1.8\times10^5$ molecules/cell 13 days post-transfection (FIG. 6). These results demonstrated that even at 2 weeks post-transfection substantial levels of CEA expression could be detected.

EXAMPLE 18

In Vivo Transduction Employing CEA-Encoding Recombinant Adenovirus

Figure 7:
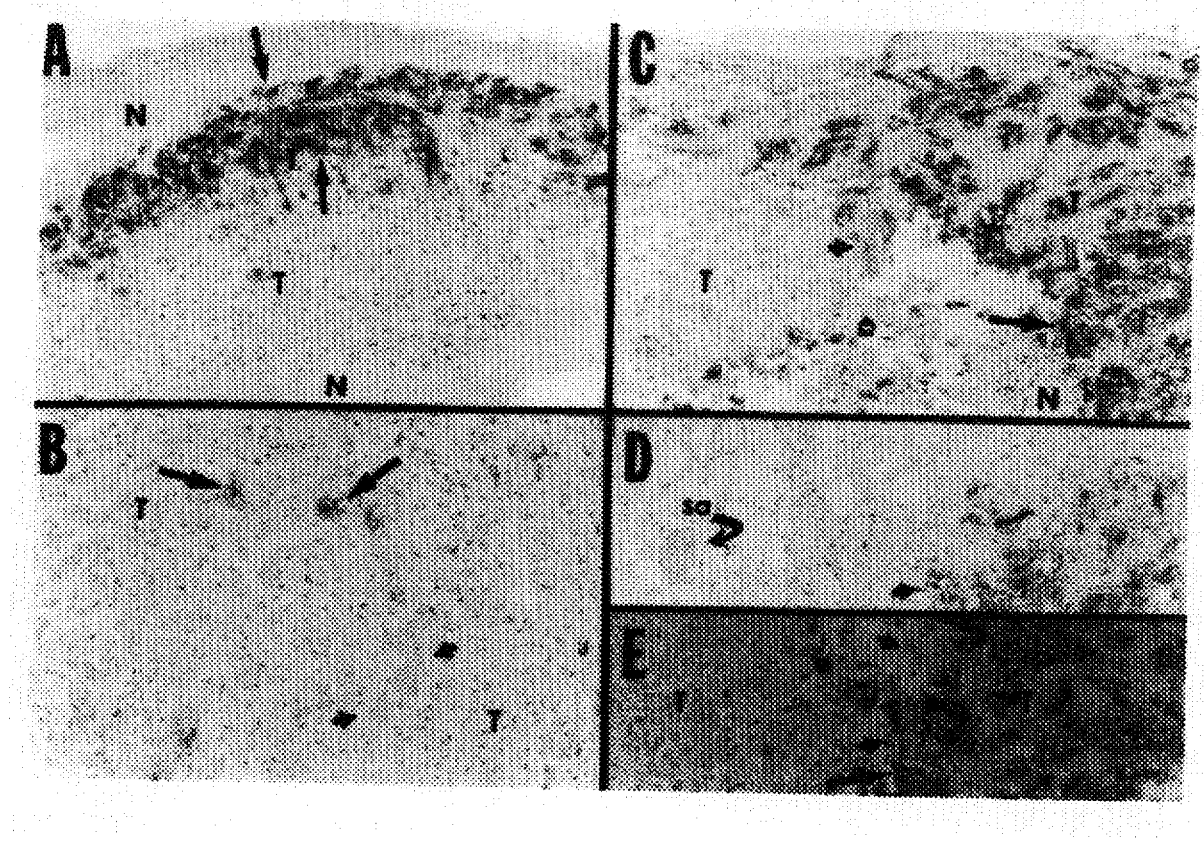
FIG. 7 shows examples of xenograft tumors (T) with focal areas of necrosis (N) shown (FIG. 7A–7E). Skin appendage (SA), hair follicle, is denoted by curved arrow.

These studies were designed to evaluate the efficiency of AdCMVCEA transduction of D54 MG xenografts via intratumoral injections and immunohistochemical analysis of CEA expression. Paraffin fixed sections of AdCMVCEA transduced tumors were stained with the anti-CEA MAb COL-1, and areas of positively stained cells were noted. Positively stained tumor cells varied between each group of mice and among individual tumors within each group (FIG. 7). D54 MG tumors that were transduced with 1–3 intratumoral injections of $1\times10^7$ PFU AdCMVCEA expressed high numbers of CEA positive tumor cells but there were large areas of the tumors that were not CEA positive (FIGS. 7A and C–D). In addition several areas of the same tumor specimen stained positive for CEA (FIGS. 7C and 7E). Adjoining skin and stromal tissues did not stain positive for CEA (FIG. 7D). In contrast the D54 MG tumors that were transduced with 1 PFU AdCMVCEA in vitro expressed only a few small clusters of CEA positive tumor cells (1 to 4 cells) at 13 days after transplantation (FIG. 7B). Control AdCMVLacZ transduced D54 MG tumors did not stain positive for CEA (not shown). These results are consistent with those observed above using immunofluorescence and immunohistochemistry for CEA quantification of cells transduced in vitro and maintained in culture.

Figure 8:
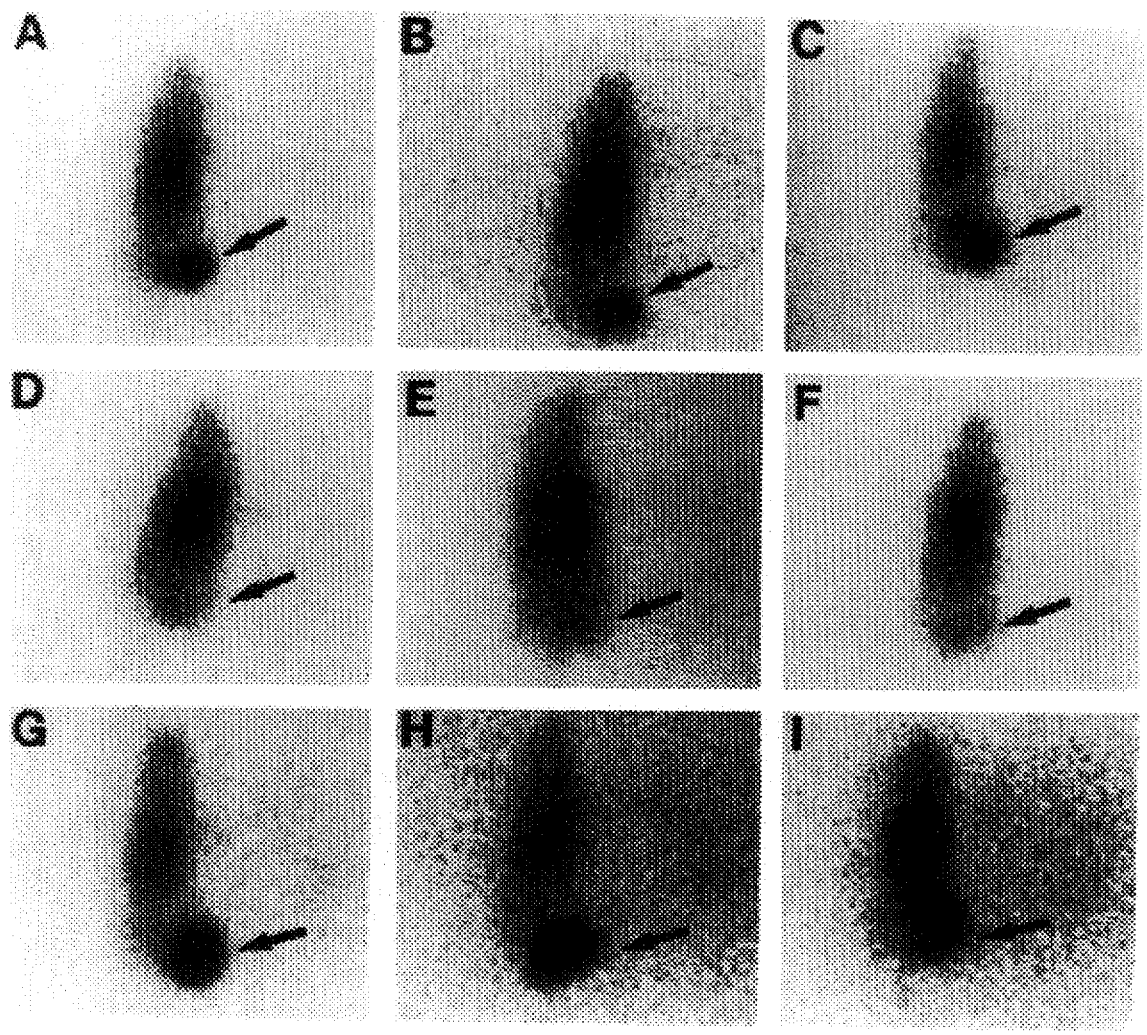
FIG. 8 shows the whole body scintigraphic images of athymic nude mice bearing (FIGS. 8A–C) AdCMVCEA transduced D54 MG subcutaneous tumors (arrows), (FIGS. 8D–F) AdCMVLacZ transduced D54 MG tumors (arrows), and (FIGS. 8G–I) LS174T tumors (arrows) given an injection of 300 μCi $^{131}$I-labeled COL-1 MAb. Dorsal images were taken at 5 days after intraperitoneal injection. Images were acquired for 50,000 cpm. The tumor weights at 5 days after injection were 0.3 to 1.1 g.

Experiments were then initiated to determine if radiolabeled anti-CEA COL-1 MAb could detect CEA on the surfaces of in vitro CEA-transduced D54 MG cells established as heterotopic subcutaneous xenografts growing on the flanks of athymic nude mice 17 days earlier. To enhance localization further, at one and two days prior to intraperitoneal injection of $^{131}$I-labeled COL-1 MAb, additional AdCMVCEA ($1\times10^9$ PFU) was injected intratumorally. The viral particle number was chosen to be 100-fold higher than for the immunohistochemistry studies described above in an effort to increase the percentage of CEA positive cells in the tumor. As a control, D54 MG cells transduced in vitro with AdCMVLacZ were similarly established as subcutaneous tumors in other mice simultaneously, and AdCMVLacZ ($1\times10^9$ PFU) was injected twice into the tumors in athymic mice as described for the D54 MG/AdCMVCEA tumors. One day later, all animals received an intraperitoneal injection of $^{131}$I-labeled COL-1 antibody (300 µCi/animal) and each mouse was imaged 5 days later. As seen in the scintigraphic images (FIG. 8), mice with xenografts containing D54 MG cells transduced with AdCMVCEA localized radiolabeled COL-1 antibody, whereas xenografts transduced with AdCMVLacZ displayed only blood pool distribution. Scintigraphic images of $^{131}$I-labeled COL-1 in animals bearing CEA-transduced tumors were similar to those obtained in LS174T tumor-bearing animals (FIG. 8). After imaging, mice were dissected and tissues were counted in a well-type gamma counter.

EXAMPLE 19

Biodistribution of $^{131}$I-Labeled COL-1 Antibody

In vivo tissue distribution of $^{131}$I-labeled COL-1 antibody in athymic nude mice bearing xenografts of D54 MG cells transduced with AdCMVCEA was undertaken to assess the extent of tumor localization. Biodistributions of 100 or 300 µCi $^{131}$I-labeled COL-1 antibody in athymic nude mice bearing AdCMVCEA transduced D54 MG cells at 4–5 days postinjection are shown in Tables I and II. As a specificity control for localization of $^{131}$I-labeled COL-1 anti-CEA antibody, athymic nude mice bearing AdCMVLacZ transduced D54 MG tumors were used. Athymic nude mice bearing xenografts of LS174T human colon cancer cells served as a positive control. Radiolabeled COL-1 tumor localization was observed in CEA-transduced D54 MG tumors that were transduced with CEA both in vitro and in situ, as well as in the positive control LS174T tumor xenografts (Table I). In contrast, no specific tumor localization was seen in the LacZ-transduced D54 MG tumors.

TABLE I

Biodistribution of $^{131}$I-labeled COL-1 MAb in tumor-bearing athymic nude mice*

| Tissue | % ID/g (mean ± SD) at 4 or 5 days postinjection |
|---|---|
| Blood | 5.4 ± 3.0 (n = 7) |
| AdCEA D54 MG | 4.8 ± 5.6 (n = 7) |
| (1 × 10⁹ PFU AdCEA/tumor) | |
| Blood | 6.3 ± 1.8 (n = 11) |
| AdLacZ D54 MG | 1.8 ± 0.7 (n = 11) |
| (1 × 10⁹ PFU LacZ/tumor) | |
| Blood | 8.4 ± 3.4 (n = 4) |
| AdCEA D54 MG | 2.5 ± 0.9 (n = 4) |
| Blood | 9.5 ± 0.6 (n = 3) |
| AdLacZ D54 MG | 2.1 ± 0.2 (n = 3) |
| Blood | 9.3 ± 4.9 (n = 5) |
| D54 MG | 1.5 ± 0.7 (n = 5) |
| (2 × 10⁷ PFU AdCEA/tumor) | |
| Blood | 9.9 ± 3.0 (n = 4) |
| D54 MG | 1.8 ± 0.9 (n = 4) |
| (2 × 10⁷ PFU AdLacZ/tumor) | |

TABLE I-continued

Biodistribution of $^{131}$I-labeled COL-1 MAb in tumor-bearing athymic nude mice[a]

| Tissue | % ID/g (mean ± SD) at 4 or 5 days postinjection |
|---|---|
| Blood | 2.2 ± 1.4 (n = 11) |
| D54 MG | 3.7 ± 1.8 (n = 11) |

[a]Athymic nude mice bearing in vitro and/or in situ transduced D54 MG tumor xenografts or LS174T colon cancer xenografts were injected intraperitoneally with 100 or 300 µCi $^{131}$I-labeled COL-1 and sacrificed 4 or 5 days after injection.
[b]Sacrificed at 4 days after intraperitoneal injection of $^{131}$I-labeled COL-1.

The concentration of COL-1 in in vitro CEA-transduced D54 MG tumors weighing 0.1–1.1 g that received 1 or 2 intratumor injections of 1×10$^9$ PFU AdCMVCEA was 4.8±5.6% ID/g which was significantly higher at 5 days after intraperitoneal injection in comparison to 1.8±0.7% ID/g with LacZ-transduced D54 MG tumors weighing 0.1–1.4 g (P=0.02). The concentration of COL-1 in LS174T human colon tumors weighing 0.5–1.5 g was 3.7±1.8% ID/g which was similar to that observed in CEA-transduced D54 MG tumors (P=0.35). Radiolabeled COL-1 concentration in blood for the three groups of animals was 5.2±3.0, 6.3±1.8, or 2.2±1.4% ID/g, respectively (Table I). Blood levels of $^{131}$I-labeled COL-1 in the CEA-transduced D54 MG tumor group were similar to the LacZ-transduced D54 MG tumor group (P=0.38), but the blood level in the CEA-transduced D54 MG group was significantly higher than the LS174T tumor group (P=0.02). This may have been a result of circulating CEA in the LS174T tumor-bearing animals (4) resulting in the formation of $^{131}$I-labeled COL-1-CEA complexes that were rapidly cleared. The concentration of COL-1 in nontransduced D54 MG tumors weighing 0.4–0.6 g that received 1 intratumor injection of 2×10$^7$ PFU AdCMVCEA 2 days before intraperitoneal injection of 100 µCi $^{131}$I-labeled COL-1 was 1.5±0.7% ID/g at 4 days after antibody injection, which was similar to that in nontransduced D54 MG tumors in the same weight range after 1 intratumor injection of 2×10$^7$ PFU AdCMVLacZ (P>0.05) (Table I). Thus, the highest uptake of COL-1 occurred in in vitro CEA-transduced D54 MG tumors following additional in situ injections of high titer AdCMVCEA.

The T/NT uptake ratios from one experiment consisting of three experimental groups are shown in Table II, and ranged from 0.9 to 8.8 in animals bearing CEA-transduced D54 MG tumors (P<0.01) to 1.9 to 11.5 in animals bearing LS174T tumors (P<0.01). Highest ratios were in muscle, bone, and small intestine. In contrast, T/NT uptake ratios in animals bearing LacZ-transduced D54 MG tumors were lower ranging from 0.3 to 2.2 although significant differences did exist among tissues (P<0.01). The differences of T/NT ratios among individual tissues also varied significantly among the three groups (Table II). To determine the overall difference of T/NT ratios, experimental group means for the nine tissues in each group were calculated and found to be 4.2, 1.4, and 5.3. Significant differences were observed among these mean adjusted T/NT ratios (P<0.05 for all). The tissue specific differences of the T/NT ratios among the three experimental groups were also compared. Except for spleen, significantly lower ratios were observed in the LacZ-transduced D54 MG tumor group compared to the CEA-transduced D54 MG tumor group or the group of animals bearing LS174T tumors. There were also lower ratios of tumor/blood, tumor/lung, and tumor/liver in the animals bearing CEA-transduced D54 MG tumors compared to the animals bearing LS174T tumors. Thus, the biodistribution of $^{131}$I-labeled COL-1 resulted in similar T/NT uptake ratios in most tissues in animals bearing CEA-transduced D54 MG tumor xenografts as in animals bearing LS174T tumors.

TABLE II

Tumor/normal tissue uptake ratios of $^{131}$I-labeled COL-1 MAb in tumor-bearing athymic nude mice[a]

| | T/NT uptake ratio (mean ± SD): 5 days postinjection | | |
|---|---|---|---|
| Tissue | AdCEA D54 MG | AdLacZ D54 MG | LS174T |
| Blood | 0.9 ± 0.6 | 0.3 ± 0.1 | 1.9 ± 0.6 |
| Lung | 1.6 ± 1.1 | 0.6 ± 0.4 | 2.8 ± 0.9 |
| Liver | 3.5 ± 2.4 | 1.3 ± 1.1 | 5.4 ± 2.2 |
| Sm. Intestine | 6.4 ± 4.5* | 1.9 ± 0.6 | 8.7 ± 3.8* |
| Spleen | 2.3 ± 1.8* | 1.5 ± 1.9* | 2.0 ± 1.4* |
| Kidney | 4.8 ± 3.7* | 1.8 ± 1.8 | 5.9 ± 2.1* |
| Skin | 3.0 ± 2.0* | 0.8 ± 0.3 | 2.9 ± 1.0* |
| Bone | 6.9 ± 5.8* | 2.0 ± 1.0 | 6.2 ± 3.4* |
| Muscle | 8.8 ± 6.2* | 2.2 ± 1.0 | 11.5 ± 9.3* |

[a]Athymic nude mice bearing in vitro and/or in situ transduced D54 MG tumor xenografts or LS174T colon cancer xenografts were injected intraperitoneally with 300 µCi $^{131}$I-labeled COL-1 and sacrificed 5 days after injection.
[b]Tumor/normal tissue uptake ratio is the % ID/g of the tumor divided by the % ID/g of the normal tissues.
[c]The T/NT ratios for each tissue were compared among the three groups of animals. They were significantly different (p <0.05) except for groups noted with an asterik.

The biodistribution of $^{131}$I-labeled COL-1 in animals bearing D54 MG xenografts that received two intratumoral injections of 1×10$^9$ PFU AdCMVCEA 1 and 2 days before COL-1 injection, and at 2 days after antibody injection are shown in Table III.

TABLE III

Biodistribution of $^{131}$I-Labeled COL-1 MAb in Tumor-Bearing Athymic Nude Mice[a]

| Tissue | % ID/g (mean ± SD) at 2 days postinjection |
|---|---|
| Blood | 6.5 ± 2.2 (n = 6) |
| AdCEA D54 MG (2 injection of 1 × 10$^9$ PFU AdCEA/tumor) | 4.4 ± 2.9 (n = 6) |

[a]Athymic nude mice bearing in situ transduced D54 MG tumor xenografts were injected intraperitoneally with 300 µCi $^{131}$I-labeled COL-1 and sacrificed at 2 days after injection.

EXAMPLE 20

Adenoviral Transduction of Non-Small Cell Lung Cancer Cells

Human lung cancer cells were transduced by an adenovirus vector. As an initial screen for vector efficacy, human non-small cell lung cancer cell lines were infected with the LacZ encoding adenoviral vector AdCMVLacZ. Following transduction, cells were harvested at 48 hours and examined for E. Coli β-galactosidase expression by fluorescence activated cell sorting (FACS). These studies confirmed high efficiency transduction of the non-small cell lung cancer cell lines tested.

EXAMPLE 21

Figure 9:
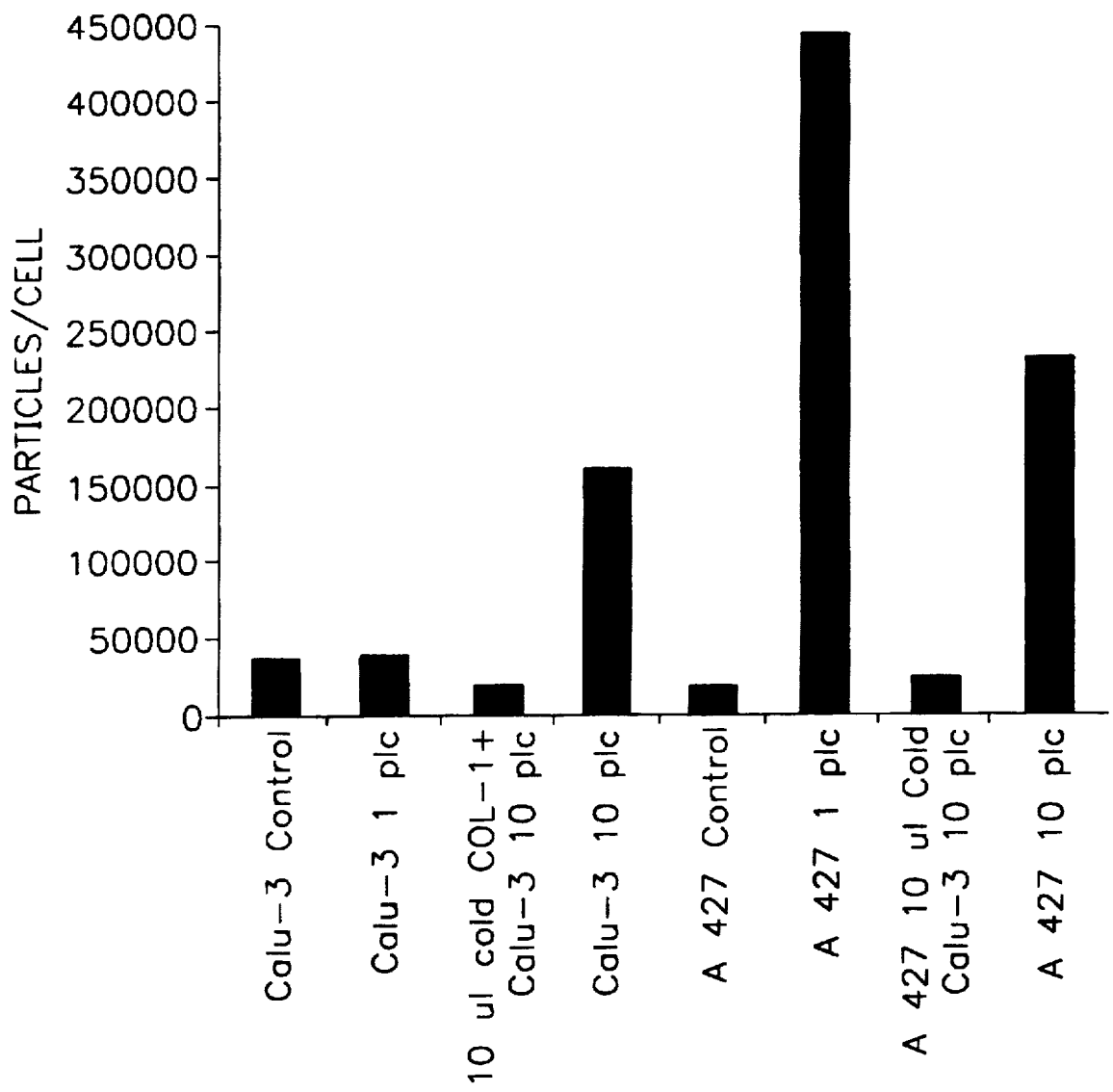
FIG. 9 shows an analysis of binding activity of $^{125}$I-labeled COL-1 Mab to AdCmVCEA transduced Calu-3 and A427 human non-small cell lung cancer cells at 1 and 10 PFU/cell. The histograms depict molecules of COL-1 bound/cell in triplicate samples. Non-transduced cells and AdCMVCEA transduced cells competitively inhibited with excess unlabeled COL-1 antibody were analyzed in comparison.

In Vitro Expression of Carcinoembryonic Antigen (CEA) in Non-Small Cell Lung Cancer Cells Transduced with Adenovirus Encoding CEA cDNA The extent to which human non-small cell lung cancer cells could be induced by adenoviral mediated gene transfer to express cell surface CEA and bind radiolabeled anti-CEA antibodies was demonstrated. CEA was used for this study because radiolabeled anti-CEA antibodies have been used extensively in experimental and clinical RAIT of various tumors and the availability of a recently produced adenoviral vector encoding the CEA cDNA facilitated rapid proof of principle. As a first step two human non-small cell lung cancer cell lines (Calu-3, A427) were transfected with 1 and 10 viral particle forming units/cell (PFU) of AdCMVCEA. These same cells transfected with AdCMVLacZ at 1 PFU/cell served as negative controls. Two days post-transfection cell membrane-associated CEA was assayed with $^{125}$I-labeled COL-1 anti-CEA MAb. The results indicated high binding efficiency of radiolabeled anti-CEA antibody to Calu-3 and A427 human lung cancer cells that had been transduced to express CEA (FIG. 9). The number of molecules of CEA expressed on the cell surface membrane was calculated to be $1.6 \times 10^5$ and $4.4 \times 10^5$ molecules bound/cell for the Calu-3 and A427 cells respectively. Thus, human non-small cell lung cancer cells were successfully transduced at high efficiency with recombinant adenoviral vectors and considerable levels of CEA expression were induced on the cell surface of the non-small cell lung cancer cell lines tested through adenoviral mediated gene transfer.

EXAMPLE 22

Genetic Induction of MurineGRP-R in Human Non-Small Cell Lung Cancer Cells

Figure 10:
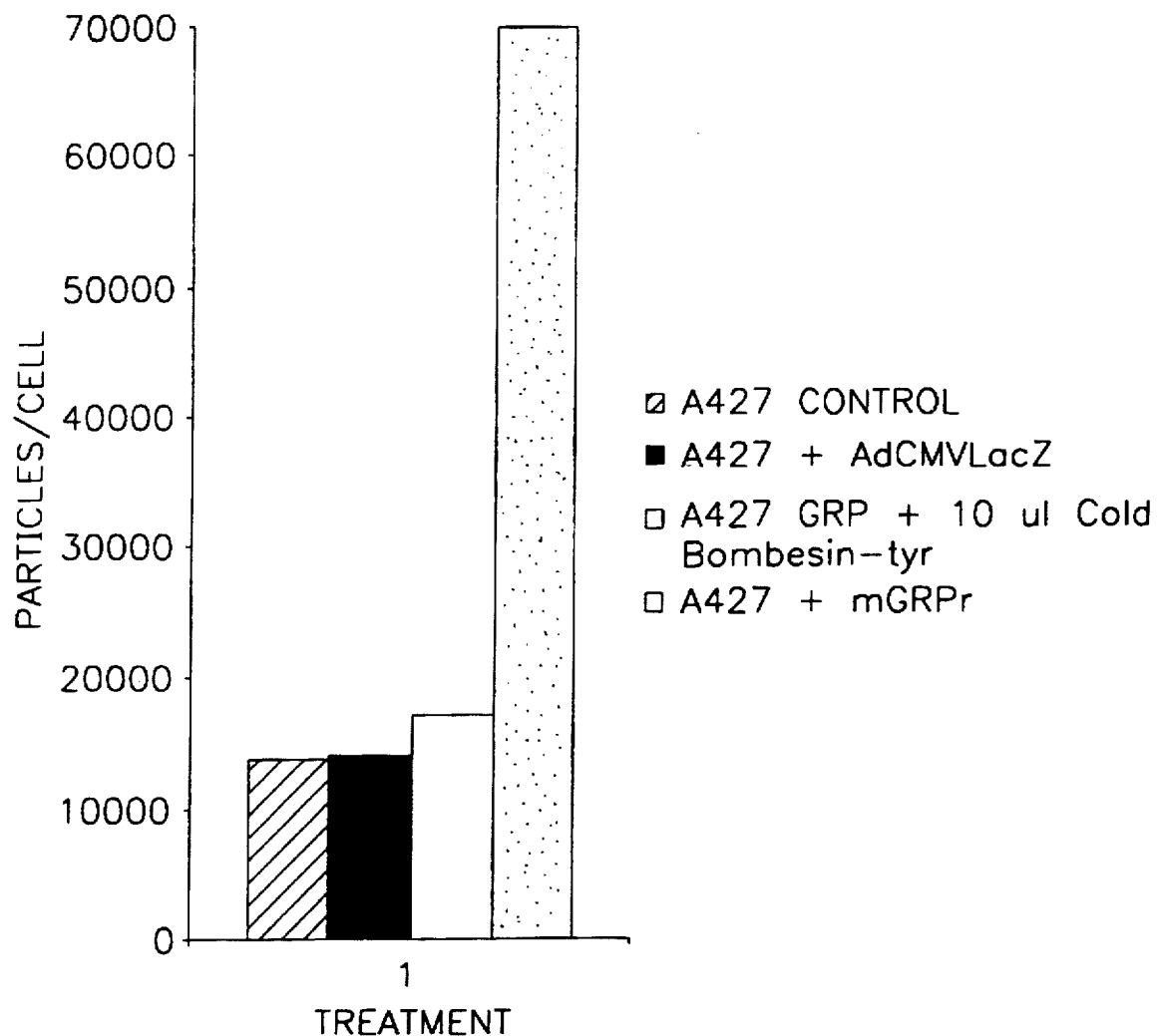
FIG. 10 shows an analysis of binding activity of $^{125}$I-labeled bombesin to A427 cells transduced to express murine GRPr using AdpL methods for gene transfer. The histograms depict molecules of bombesin bound/cell in triplicate samples. Non-transduced A427 cells, A427 cells transduced with adenovirus encoding LacZ reporter gene and transduced cells competitively inhibited with excess cold bombesin were analyzed in comparison.

Next, gene mediated expression of receptors was applied in the context of inducing expression of a receptor that could be targeted with a radiolabeled peptide and thus employed the gene encoding the murine gastrin releasing peptide receptor (mGRP-R). The first technique utilized the methodology of an adenovirus-polylysine-mediated transfection (AdpL) to accomplish transient gene expression of mGRP-R in human lung cancer cells. Expression of mGRP-R in transduced target cells in comparison to uninfected controls was successfully demonstrated as measured by $^{125}$I-labeled bombesin binding (FIG. 10). Thus, it was demonstrated that this receptor exhibits the characteristics applicable to induce expression of a receptor targetable by a low molecular weight radiolabeled peptide.

EXAMPLE 23

Gene Therapy for Breast Cancer

The present invention shows the induction of high levels of carcinoembryonic antigen on glioma and breast cancer cells. This approach can be developed as a radiation/gene therapy strategy to target therapeutic levels of ionizing radiation to disseminated breast cancer. The ability to specifically transduce cells with a receptor or antigen that can be targeted with a radiolabeled ligand allow for the derivation of clinical radiation/gene therapy strategies for breast cancer.

Experiments were carried out to demonstrate the induction of carcinoembryonic antigen on glioma and breast cancer cells. Binding of a $^{125}$I- and $^{131}$I-radiolabeled monoclonal antibody (MAb) to the genetically induced CEA antigen was shown. Based on these findings, genetic induced receptors/antigens can be used to target therapeutic levels of ionizing radiation to tumor cells and this strategy can be developed as an experimental radiation/gene therapy strategy for breast cancer.

Despite a multidisciplinary approach in patients at high-risk for distant dissemination, breast cancer results in more than 45,000 deaths per year overall. The biology of breast cancer implicates a systemic rather than a local disease at the time of diagnosis. Since RAIT can potentially target systemic disease, RAIT also holds promise in treating metastatic breast cancer. MAbs to several breast cancer antigens have been exploited for RAIT of metastatic breast cancer. These include: CEA, human milk fat globule (HMFG) and epithelial membrane antigens (EMA), integral membrane glycoprotein triggers of cell growth (L6) or transformation and growth factor receptors. However, the clinical results for treating metastatic breast cancer with RAIT have been disappointing. The major limitation in the development of effective RAIT for breast cancer is reflected in the fundamental problem of achieving adequate tumor localization of radiolabeled antibodies. This is due, in large part, to the low expression of the target antigen or to biodistribution problems associated with using high molecular weight antibodies as the targeting agent. Additionally, RAIT for breast cancer is limited by bone marrow suppression and HAMA responses. The present invention addresses these limitations by genetically inducing the expression of cell surface receptors with high affinity for radiolabeled low molecular weight peptides. Thus, this strategy is an overall treatment of breast cancer by systemic administration when the tumor burden is at a microscopic level in an effort to eradicate distant metastases.

EXAMPLE 24

Genetic Radio-Isotope Targeting Strategy (GRITS) as an Improvement for Conventional RAIT To overcome these problems of RAIT we have devised a strategy to genetically induce high levels of new membrane-associated receptors with high affinity for a peptide ligand. A membrane-associated receptor that is not normally expressed on a tumor can be transduced by direct intratumor injection of a recombinant adenovirus that encodes the receptor gene under the control of a constitutive promoter. The receptor would then be expressed at a high level on the membrane of the tumor cells. This would overcome the problem of the absence of targetable antigens or the low expression of these antigens in conventional RAIT. Membrane-associated receptors have the additional advantages of recognition by small peptide ligands that have high affinity binding to the receptors, short serum half-lives reducing the radiation dose to normal tissues, and greater intratumor penetration to produce a more homogeneous radiation dose. These characteristics of the peptide ligands overcome the slow penetration of large antibodies, the bone marrow suppression due to long serum half-lives and lower antigen affinity of the antibodies and the development of HAMA responses.

EXAMPLE 25

Peptide Receptor Scintigraphy (PRS) as a Model for GRITS

PRS follows the concept that after injection, radioactive ligands can be bound to or transported into cells which possess cell surface receptors for these ligands. If the density of these high-affinity receptors on tumor cells or the number of cells with these sites in a tumor is high enough to give a radioactive signal after binding that is higher than the surrounding tissue, this signal can be displayed using a γ-emission detecting instrument. There are at least four necessary elements for PRS to be effective. First, binding to the receptor occurs with high affinity in the presence of a high density of receptors. Second, the equilibrium between receptor binding and plasma clearance is essential. If serum clearance is too rapid the ligand-tissue levels will be below the optimal level. Third, the binding of the radioligand should be instantaneous with high specific activity at the receptor site to achieve more binding of radiolabeled ligand than the unlabeled peptide. Fourth, the choice of radioligand is important with reference to the distribution and metabolism of the radioligand.

In order to develop GRITS for treatment of local disease the induction of a cell surface antigen/receptor was first demonstrated. Radiolabeled anti-CEA antibodies have been used extensively in experimental and clinical RAID and RAIT of various tumors including colorectal, lung and breast carcinomas. The therapeutic efficacy using radiolabeled intact antibodies compared to scFv after CEA transduction could be determined in human breast cancer cell xenografts in a murine model.

EXAMPLE 26

Tumor Specific Expression of Receptors or Antigens to Treat Disseminated Disease Although this strategy would be useful for the treatment of advanced localized breast cancer, recurrence of the tumor in sites distal to the primary disease are the leading cause of breast cancer therapy failure. Transduction or transcription targeting can be used to achieve gene expression in metastatic nodules. Transduction targeting directs the delivery of the DNA to the malignant tissue. Transcription targeting uses regulatory sequences to regulate expression of the receptor/antigen gene in a tissue specific manner. The strategy is based on the regulation of gene expression using tumor and/or tissue specific promoters driving the expression of a cell surface receptor or antigen. This strategy requires the identification of regulatory sequences that are highly expressed in a majority of a particular carcinoma and a minority of normal tissue. Several genes have been shown to be overexpressed in breast cancer cells. These genes include CEA (10–30%), erbB-2 (20–30%) and DF3/mucin1 (70–90%). The overexpression of these genes has been shown to occur at the transcriptional level. Therefore, these tissue specific promoters linked to a receptor or antigen gene would express the receptor or antigen only on the tumor cells. This strategy could be developed for the treatment of metastatic disease.

EXAMPLE 27

Genetic Induction of CEA to Augment RAIT for Breast Cancer Therapy

Figure 11:
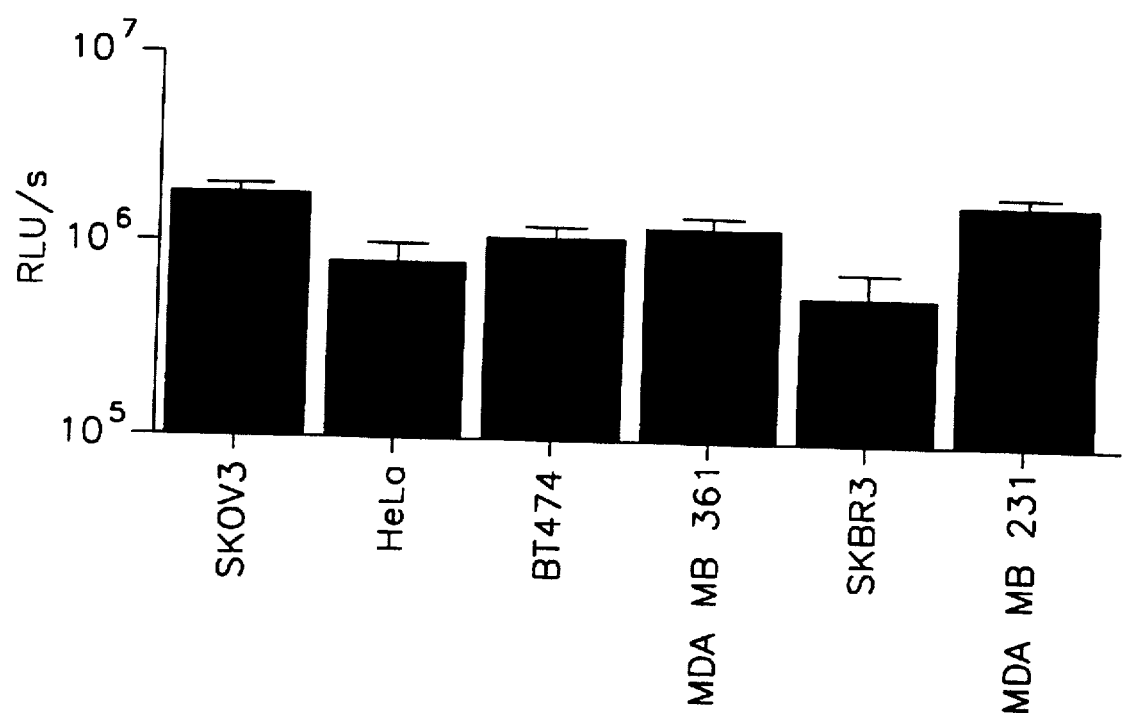
FIG. 11 shows the luciferase gene expression after AdpL transfection of breast cancer cell lines BT 474, MDA-MB-361, MDA-MB-231, and SKBR3. SKOV3 and HeLa cells were used as positive controls. The results are expressed as relative light units/second (RLU/s).

The breast carcinoma cell lines (MDA-MB-361, MDA-MB-231, MDA-MB-468, ZR-75-1, SK-BR-3, MCF-7, and BT-474) were used to evaluate GRITS. Many of these breast cancer cell lines are transducible using the AdpL transfection method with a firefly luciferase reporter gene. Several of these breast cancer cell lines were found to be highly transducible, expressing high levels of luciferase compared to untransfected controls (FIG. 11).

Figure 12:
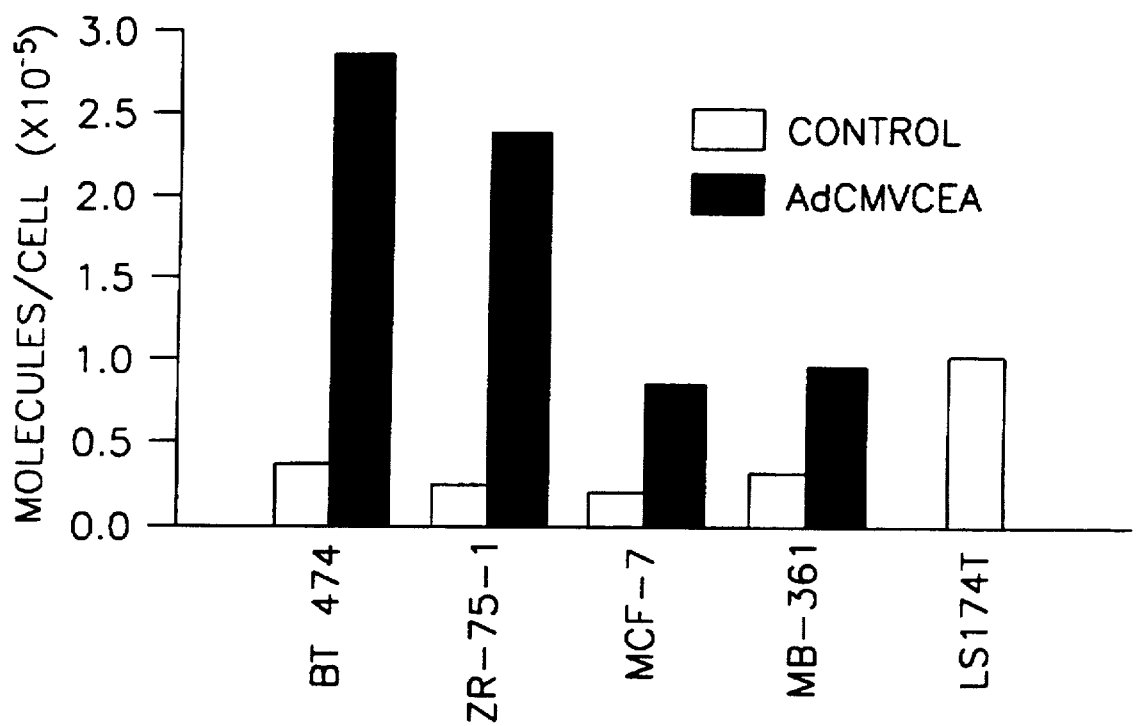
FIG. 12 shows the analysis of binding activity of $^{125}$I-labeled COL-1 MAb to BT474, MDA-MB-361, ZR-75-1, and MCF-7 cells transfected with AdCMVCEA at 10 PFU/cell. Non-transduced breast cancer cells as well as LS174T cells constituitively expressing CEA were analyzed in comparison. The histograms depict molecules of COL-1 bound/cell sample.
Figure 13:
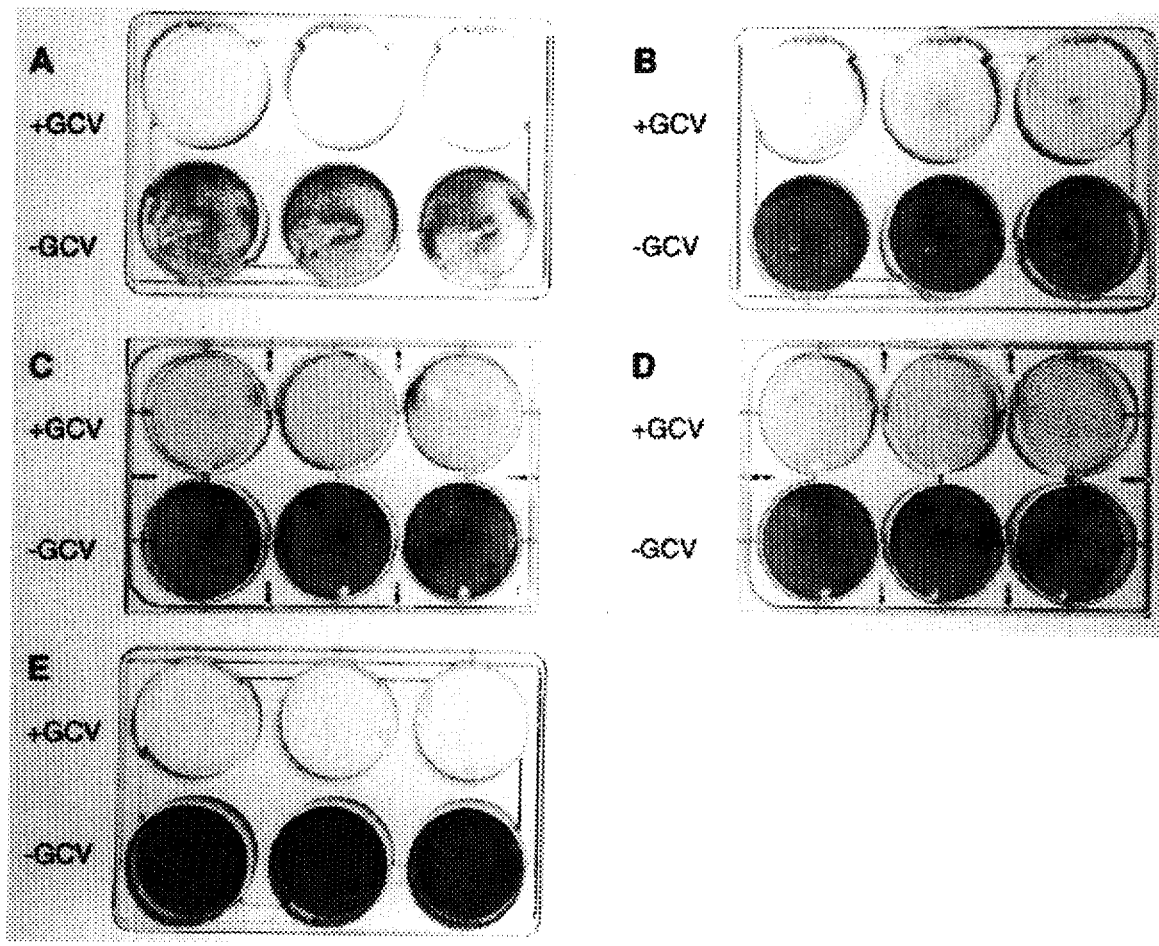
FIG. 13 shows an analysis of erbB-2 specific expression of the TK gene. Panel A: SKOV3 cells transfected with psv/HSV-TK; Panel B: SKOV3 cells transfected with erbB-2-HSV-Tk; Panel C: HeLa cells transfected with psv/HSV-Tk; Panel D: HeLa cells transfected with erbB-2-HSV-TK; Panel E: HeLa cells untransfected. In all panels top 3 wells contained 20 mM GCV. Bottom 3 wells media only.

Breast cancer cell lines can be transduced using AdpL transfection. The genetic constructs developed are validated using AdpL transfection and the appropriate assay for gene expression. The next step to develop GRITS in breast cancer cells was to demonstrate CEA induction after infection with AdCMVCEA. This was accomplished by an analysis of the in vitro binding of $^{125}$I-labeled COL-1 MAb to transfected and nontransfected breast cancer cells (FIG. 12). Several breast cancer cell lines can be transduced with the AdCMVCEA adenovirus to express CEA demonstrated by radiolabeled COL-1 MAb binding. The levels induced were somewhat lower than observed for the glioma cell line. The optimal MOI for these breast cancer cells can be determined.

To transfect metastatic breast cancer it is desirable to control the expression of the genetically induced receptors or antigens by using tumor specific promoters to drive the expression of the desired gene. This would target the expression of high levels of cell surface antigens or receptors specifically on metastatic nodules. Recombinant adenovirus could deliver the tumor specific constructs to metastatic nodules and only cells expressing the tumor specific promoter would express the antigen or receptor. To prepare recombinant adenovirus, shuttle vectors were constructed. These shuttle vectors are the first step in producing recombinant adenovirus.

EXAMPLE 28

Determination of the Therapeutic Efficacy of the Tumor Specific Genetic Radio-Isotope Targeting Strategy The recombinant adenovirus can be delivered to metastatic breast cancer. One can then directly determine the benefit of this treatment. To this end, xenografts of human breast cancer are established in nude mice and the tumor-bearing mice are treated with the recombinant adenovirus and the expressed receptor/antigen are targeted with radiolabeled ligand/antibody to achieve a therapeutic effect. Animals are evaluated for parameters of efficacy including reduction in tumor burden and prolongation of survival.

EXAMPLE 29

Plasmid Construction

Figure 14:
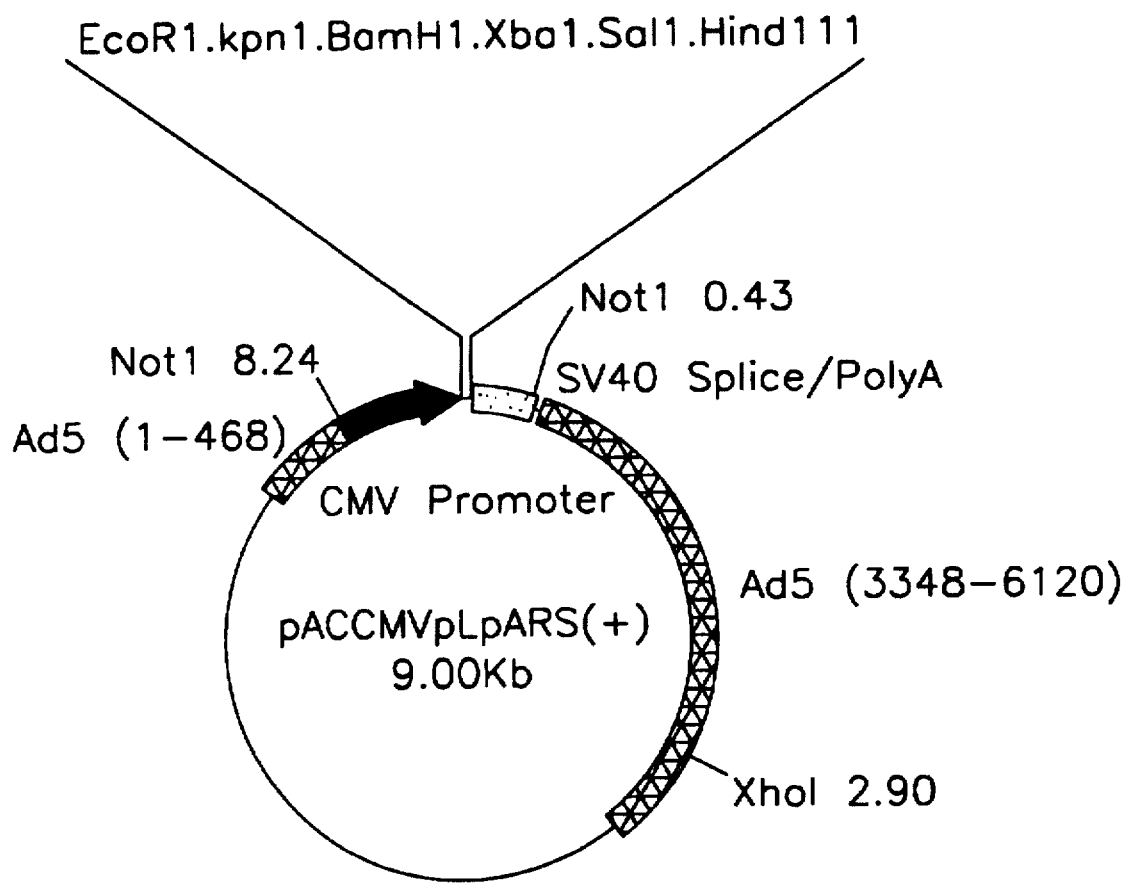
FIG. 14 shows the construction of the shuttle vector pACCMVpLpARS(+) under the control of the CMV promoter.

The cytomegalovirus promoter (CMV) was replaced in the pACCMVpLpARS(+) (FIG. 14) adenovirus shuttle vector (obtained from R. Gerard) with the promoter region from the DF3/MUC1 gene using the following strategy: 1) the DF3 promoter region was amplified (positions −725 to +31, Genbank accession no. L06162) by polymerase chain reaction (PCR) from human genomic DNA in a Stratagene Robocycler with a temperature gradient. This promoter region was shown to have tissue specific expression using a CAT assay in MCF-7 breast cancer cells (Abe and Kufe, 1993, PNAS 90:282). The upstream primer 5' GGCGGCCGCTCCTGGCCAGTGGTGGAG3' contained a Not I restriction enzyme site and the downstream primer 5'AGAATTCAGGCAGGCGCTGGCTGCTTGAGAG3' contained an Eco RI restriction site (underline represents the restriction sites).

Figure 15:
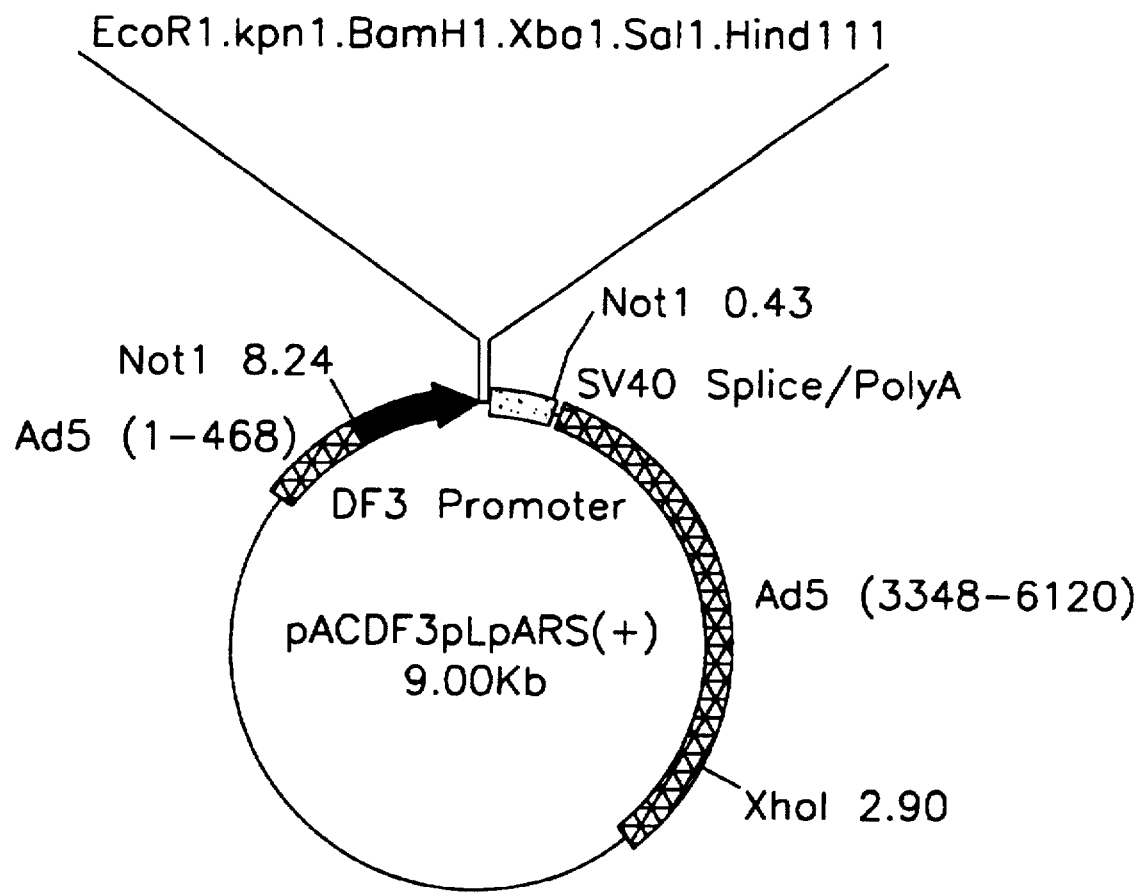
FIG. 15 shows the construction of the shuttle vector, pACDF3pLpARS(+) under the control of the DF3 promoter.

The PCR conditions were Promega PCR buffer, 1.5 mM MgCl$_2$, 200 mM dNTP, 50 mM each primer, and 1.5 Units Taq (Promega), 94° C., 1 minute, 70–74° C. annealing 1 minute, 72° C. extension 1 minute, for 35 cycles. The PCR product size was confirmed by gel electrophoresis. Secondly, the PCR product was cloned into the TA cloning vector (Novagen). This plasmid was digested with Eco RI and Not I to release the DF3 promoter with the appropriate sites for cloning into the adenovirus shuttle vector pACCMVpLpARS(+). Next, the shuttle vector was restriction digested with Eco RI and Xho I. The 3 Kb fragment generated was excised from the gel, purified and dephosphorylated. The shuttle vector was next digested with Not I and Xho I and isolated the 5 Kb fragment. The 3 fragments generated were then ligated together to form the plasmid pDF3pLPARS(+) (FIG. 15).

Figure 16:
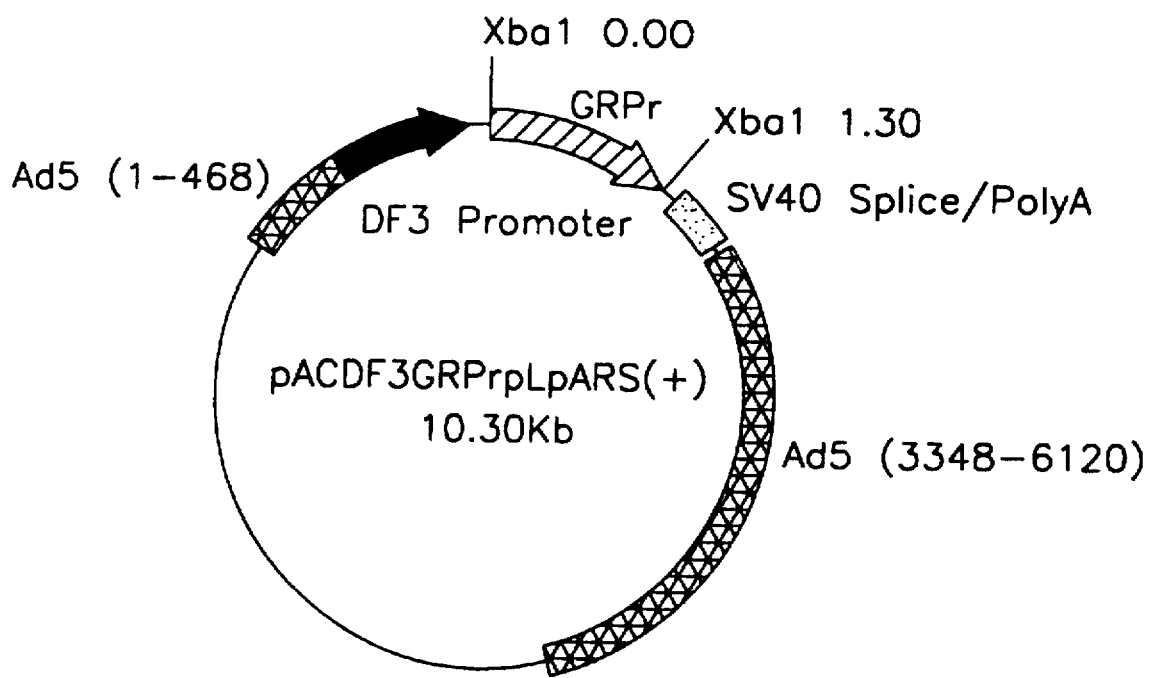
FIG. 16 shows the construction of the shuttle vector pACDF3pGRPrpLpARS(+) expressing the gastrin releasing peptide receptor under the control of the DF3 promoter.
Figure 17:
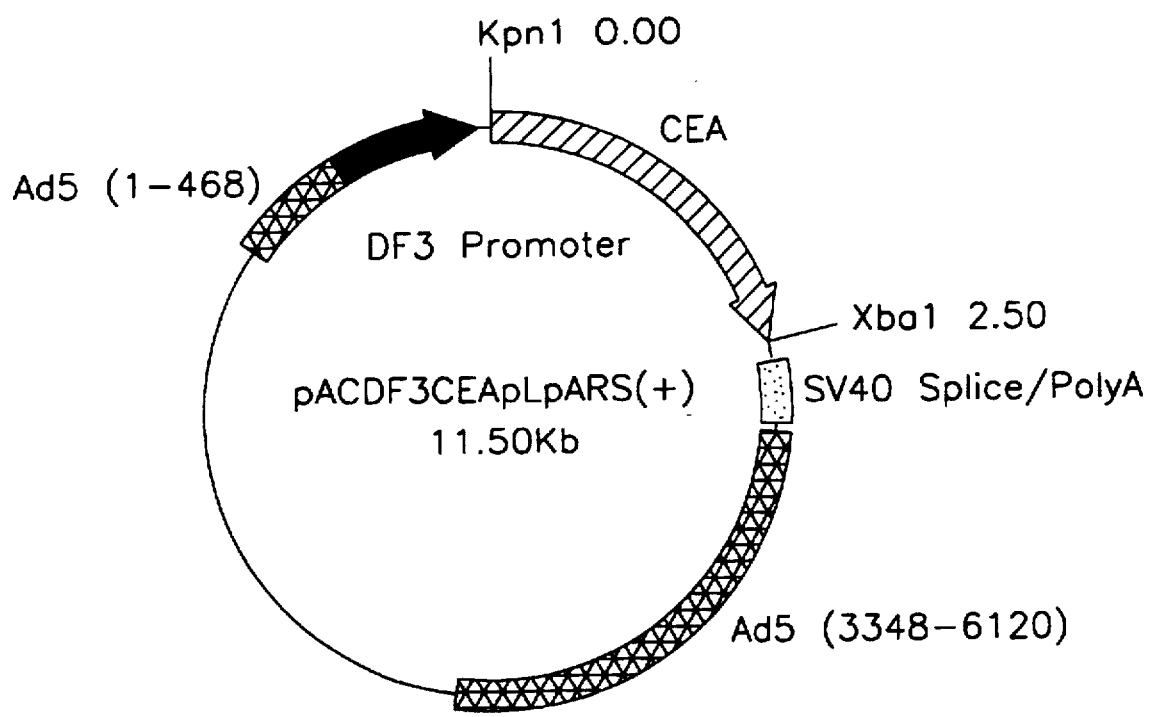
FIG. 17 shows the construction of the shuttle vector pACDF3pCEApLpARS(+) expressing the carcinoembryonic antigen under the control of the DF3 promoter.
Figure 18:
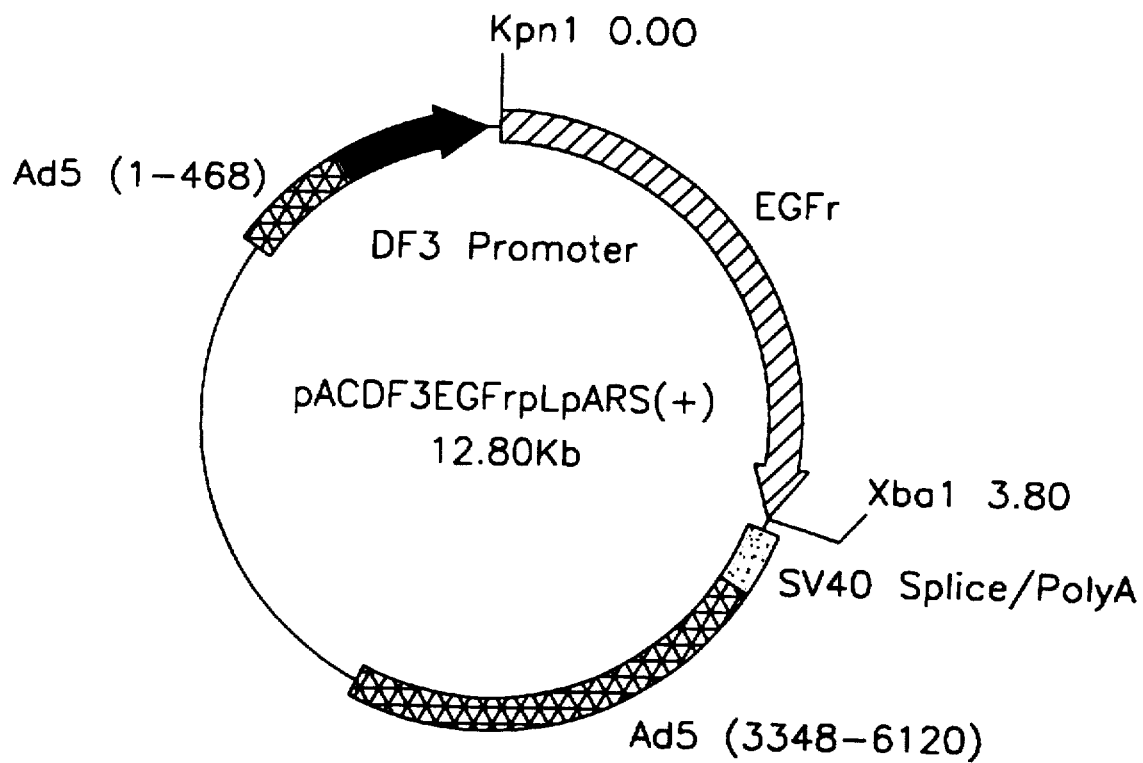
FIG. 18 shows the construction of the shuttle vector pACDF3pEGFrpLpARS(+) expressing the epidermal growth factor receptor under the control of the DF3 promoter.

The shuttle vector pACCMVpLpARS(+) contains the polycloning site from the pUC18 plasmid which was preserved in the pDF3pLpARS(+) plasmid. All the genes cloned into pDF3pLpARS(+) were cloned into this polylinker region. These include gastrin releasing peptide receptor (Xba I), carcinoembryonic antigen (Kpn I/Xba I), and epidermal growth factor (Kpn I/Xba I) (FIGS. 16–18).

EXAMPLE 30

Gene Expression

The cell lines used were HeLa (DF3 non-expressing) and MCF-7 (DF3 expressing breast cancer cell line). Cells were maintained in DMEM (HeLa) or DMEM/F12 (MCF-7) 10% FBS 1% Glutamine. $5\times10^5$ or $7.5\times10^5$ HeLa or MCF-7 cells, respectively, were plated into each well of 6-well tissue culture dishes. Twenty-four hours later, the cells were tranfected with the plasmid encoding the firefly luciferase gene under the control of the CMV or DF3 promoter using the adenovirus-polylysine method (AdpL, Curiel, 1994, *Nat. Immun.* 131:141–164). Cells were mock transfected as a negative control 3 wells were transfected for each condition and cell line. Six mg of endotoxin removed plasmid in 200 ml of Hepes buffered saline (HBS) was mixed with 100 ml of the polylysine conjugated adenovirus and incubated at room temperature for 30 minutes. The DNA-adenovirus complex was added to 4 mg of free polylysine in 300 ml HBS and incubated an additional 30 minutes. During this incubation, the media was removed from the cells previously plated and replaced with 0.5 ml media with 2% FBS per well. 100 ml of the appropriate AdpL mixture was added to each well. The plates were incubated at 37° C. for 1.5 hours and then 3 ml of growth media was added to each well. After 24 hours incubation the media was removed and replaced with fresh growth media. Twenty four hours later the cells were assayed for expression of the firefly luciferase enzyme. A firefly lucifase reporter assay kit (Promega) was used. Cells were lysed in 300 ml lysis buffer. 20 ml of sample was added to 100 ml of luciferase assay buffer. Luciferase expression was determined as relative light units (RLU) measured in a luminometer (10 s counts triplicate samples). Soluble protein content of the lysate was determined using a protein quantification kit (BioRad). The RLU was corrected for mg soluble protein and plotted.

EXAMPLE 31

Results

Figure 19:
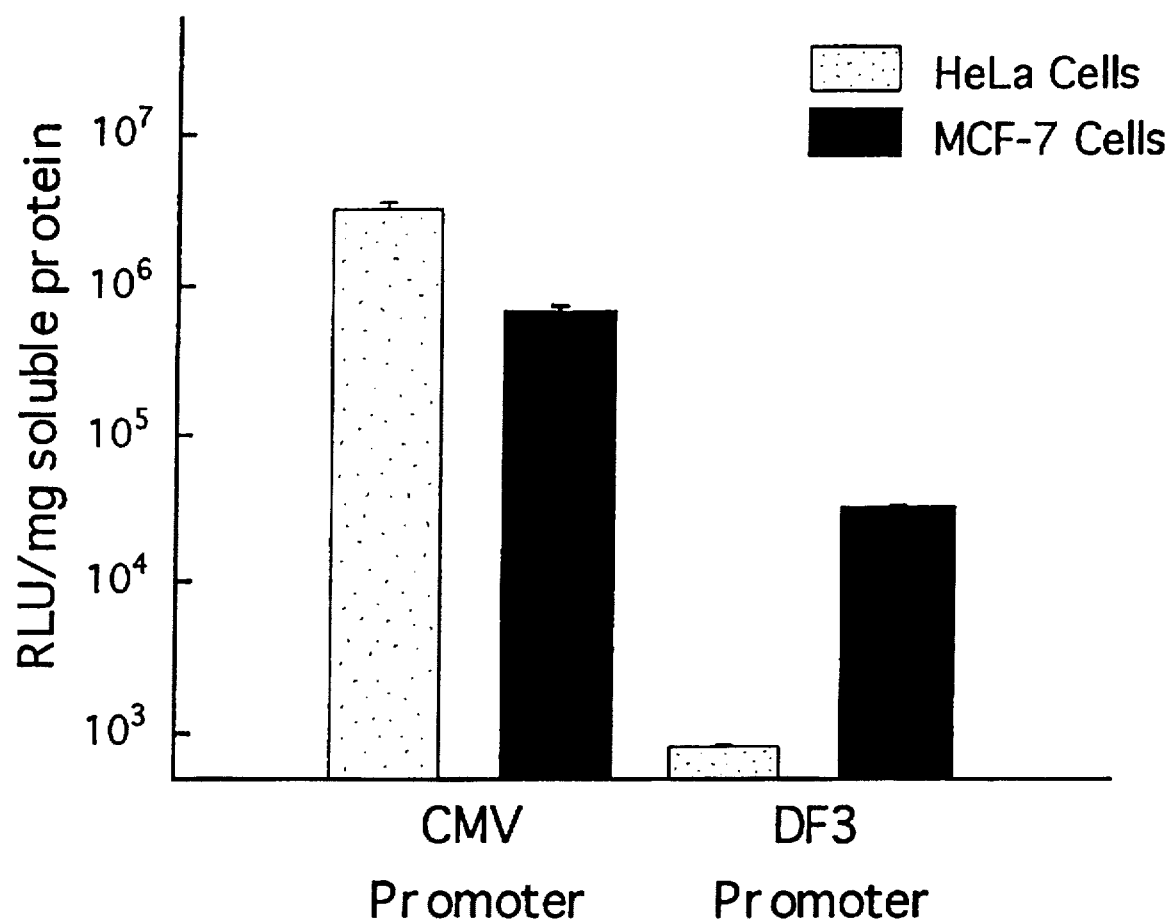
FIG. 19 shows the firefly luciferase gene expression in HeLa (DF3 non-expressing) and MCF-7 (DF3 expressing) cells using specific and non-specific promoters to drive gene expression. Cells were transfected with plasmids encoding the luciferase gene under the control of the CMV or DF3 promoters using the AdpL transfection method. Mock transfected cells served as negative controls. Cells were plated 24 hours before transfection. Fourty-eight hours after transfection the cells were lysed and gene expression was determined using a Promega gene expression kit. Light emission was measured by a luminometer. Results were expressed as relative light units (RLU) and corrected for soluble protein content. Little gene expression was observed in HeLa cells under the control of the DF3 promoter compared to MCF-7 cells. This figure shows tissue specific gene expression using the DF3 promoter in a permissive background. Error bars are the mean of three replicate determinations from a single experiment.

The CMV promoter drives gene expression in mammalian cells in a non-specific manner. The DF3/MUC1 gene is overexpressed in a majority of breast carcinomas. The promoter region from the DF3 gene can only drive gene expression in cells that express the DF3 gene. The expression of firefly luciferase was determined in HeLa (DF3 non-expressing) and MCF-7 (DF3 expressing) cell lines after transfection with plasmids under the control of the CMV promoter or DF3 promoter. Luciferase gene expression controlled by the CMV promoter was observed in both HeLa and MCF-7 cells although the level of expression was 5 fold greater in HeLa cells compared to MCF-7 cells (FIG. 19). The expression of luciferase in MCF-7 cells under the control of the DF3 promoter was 37 fold greater than in HeLa cells. The DF3 promoter was not as efficient as the CMV promoter in MCF-7 cells (21 fold lower). No luciferase expression was observed in mock transfected cells.

EXAMPLE 32

Transfection of Ovarian Cancer Cells with AdCMVCEA

An additional example was accomplished in the context of ovarian carcinoma. In this regard, the target cell was SKOV3.ip1, a human ovarian carcinoma cell line. Cells were seeded into 75 cm² flasks ($1-2\times10^6$ cells/flask) and then infected with either ADCMVCEA or AdCMVLacZ at a MOI of 10 PFU per cell. Noninfected SKOV3.ip1 cells were also tested. After 24–72 hours, cells were harvested and analyzed by indirect immunofluorescence and immunohistochemistry for unlabeled COL-1 anti-CEA antibody binding or for $^{125}$I-labeled COL-1 binding. The human colon cancer cell line LS174T was used as a positive control for COL-1 binding. The results for COL-1 immunohistochemistry are shown in Table 4.

TABLE 4

Immunohistochemistry on AdCEA transfected SKOV3.ip1 cells

| Cells | Antibody | Result |
|---|---|---|
| SKOV3 | COL-1 | Negative |
| LS174T | COL-1 | Positive |
| SKOV3/AdCEA | COL-1 | Positive |
| LS174T | None | Negative |
| SKOV3/AdCEA | None | Negative |

Figure 20:
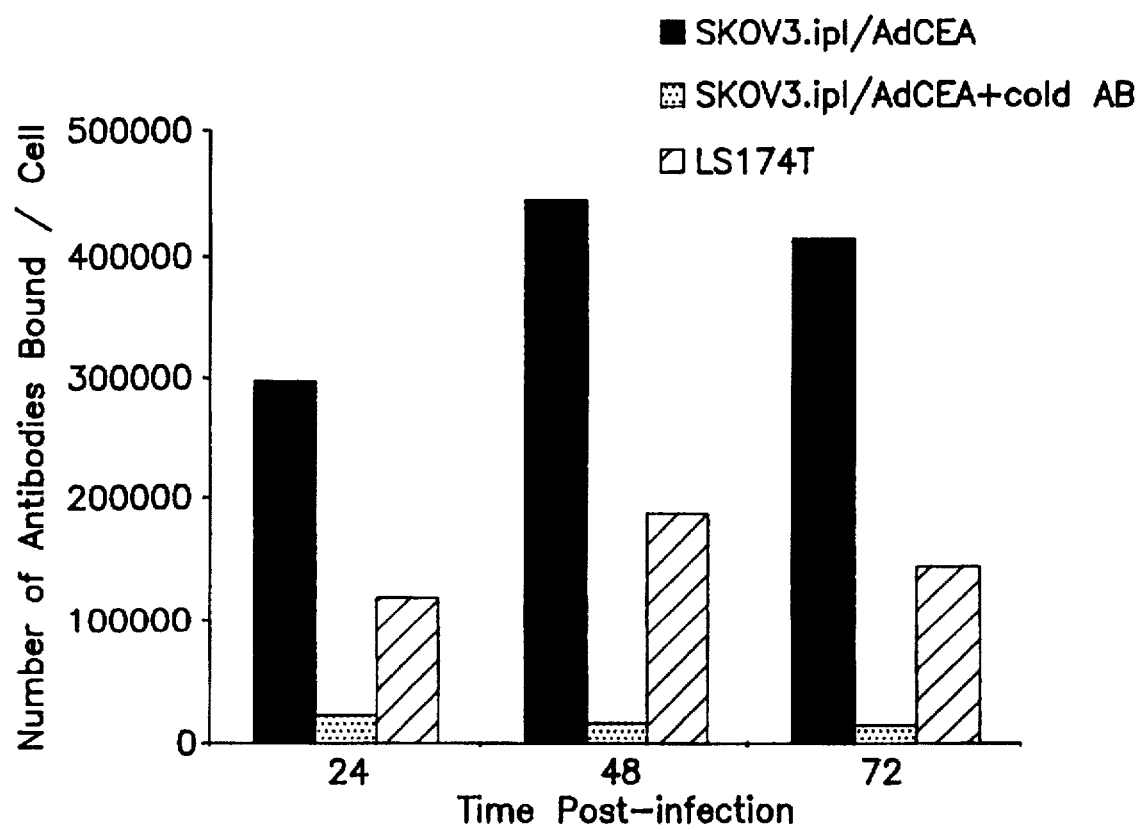
FIG. 20 shows the level of CEA expression induced in SKOV3.ip1 cells transfected in vitro with AdCEA. SKOV3 cells were infected with 100 pfu/cell of AdCEA. Cells were harvested at 24, 48 and 72 hours for binding with $^{125}$I-labeled COL-I.

Immunofluorescence results indicated that greater than 95% of the AdCMVCEA transfected SKOV3.ip1 cells expressed CEA. The results for radiolabeled COL-I binding are shown in FIG. 20. These results show that the CEA expressing adenovirus, AdCMVCEA, can induce CEA expression and hence $^{125}$I-labeled COL-1 antibody binding in human ovarian carcinoma cells which persists for at least 72 hours following transfection and at a level more than 2-fold higher than LS174T cells that constitutively express CEA.

The present invention developed gene therapy strategies that could be used to improve upon existing RAIT approaches. To this end, a recombinant adenoviral vector was constructed encoding CEA cDNA driven by a CMV promoter to accomplish genetic induction of CEA expression as a target for radiolabeled antibodies. The efficacy of this AdCMVCEA vector construct in accomplishing transduction of target cells was evident by indirect immunofluorescence with anti-CEA COL-1 MAb. Moreover, immunohistochemical analysis indicated substantial binding of unlabeled COL-1 to AdCMVCEA transduced D54 MG cells maintained in culture. Furthermore, radiolabeled binding assays confirmed the ability of AdCMVCEA to transduce D54 MG cells to express CEA as the data revealed impressive $^{125}$I-labeled COL-1 binding to AdCMVCEA transduced D54 MG cells. Through in vitro transduction of D54 MG cells, followed by single or multiple injections of AdCMV-CEA into established D54 MG xenografts in vivo, CEA positive tumor cells were demonstrated by immunohistochemistry analysis. Intraperitoneally administered $^{131}$I-labeled COL-1 MAb localized to tumors as shown by external scintigraphic imaging. Biodistribution studies confirmed favorable uptake of radiolabeled COL-1 antibody in tumor in relation to normal tissues. Thus, the present invention has shown that adenoviral mediated gene transfer produces high levels of CEA expression on the surface of D54 MG cells in vitro. Furthermore, the present invention successfully translated this approach in vivo by demonstrating enhanced radiolabeled antibody localization in tumor xenografts.

CEA was presently employed as one of several possible induced tumor targets in the gene therapy strategy described by the present invention. This choice was based on the fact that radiolabeled anti-CEA antibodies have been used extensively in experimental and clinical radioimmunodetection (RAID) and RAIT of various tumors including colorectal, lung, and breast carcinomas (155–169). In this regard, CEA is a well characterized $M_r$ 180,000 glycoprotein oncofetal antigen without known transforming capacity. Recently, a cDNA clone and a genomic clone coding for full-length CEA were subcloned into an expression vector and transfected into Chinese hamster ovary and mouse L-cell fibroblasts by Hefta et al. Subsequently, Robbins et al. demonstrated successful transduction of the MC-38 mouse adenocarcinoma cell line with a retroviral construct encoding human CEA cDNA measured by indirect immunofluorescence. Clones of cells were obtained that expressed levels of cell surface CEA comparable to those found in human colon cancer cell lines that express high levels of CEA. The CEA-transduced MC-38 cells were shown to grow and express CEA in athymic nude mice, and $^{125}$I-labeled anti-CEA COL-1 antibody was shown to target these in vitro transfected tumors in vivo. Thus, CEA has served as an appropriate tumor marker in the context of RAID and RAIT strategies.

The present invention discloses a genetic strategy to accomplish RAIT and overcome some of the limitations noted with this approach. Limitations to successful RAIT have principally been attributable to inadequate expression of a targetable antigen at the tumor site. In this regard, several investigators have demonstrated a direct relationship between tumor antigen content in human tumor xenografts and localization of radiolabeled antibody (3–6). Based upon this concept, strategies have been developed to upregulate the target antigen on tumor cells. In contrast to this approach, the present invention teaches increased expression of targetable cell surface antigen or receptors in tumor cells using a gene therapy strategy. The advantages of the genetic transduction approach disclosed include: (a) constitutive expression of a tumor-associated antigen is not required; (b) tumor cells are altered to express a new target antigen or receptor at levels which may significantly improve tumor to normal tissue targeting of radiolabeled antibodies or peptides; (c) adenoviral-mediated gene transduction is efficient, requiring only 1 virus/tumor cell; and (d) gene transfer can be effected by intratumor injection of the replication-defective adenoviral construct, through regional administration, and by systemic administration.

As previously mentioned, the biodistribution data demonstrated a higher blood level of COL-1 in the AdCMVCEA transduced D54 MG tumors and lower T/NT uptake ratios in the blood, lung and liver than in the LS174T tumor group. In this regard, several technical limitations which may have contributed to suboptimal results in vivo include lower titers of AdCMVCEA introduced intratumorally in these initial experiments. In addition, the viral inoculum was administered in a single injection. To address these limitations, in vitro transduction was combined prior to implantation, as well as increasing the number of viral particles injected intratumorally. Moreover, injections were administered on two consecutive days in an effort to enhance transduction.

Finally, two injections of a high number of viral particles in situ only ws evaluated. To this end, successful tumor localization by intraperitoneally administered $^{131}$I-labeled COL-1 MAb was accomplished and found to be comparable to localization seen in the LS174T positive control xenografts.

In summary, the present invention demonstrates the practical application of a novel strategy to improve RAIT through genetic induction of tumors in situ to express a new membrane associated molecule which can be easily targeted by radiolabeled ligands. In one embodiment, this strategy involves direct intratumoral injections of an adenoviral vector to achieve efficient and rapid transduction. It should be possible to achieve adequate transduction by regional administration (e.g. intraperitoneal injection for peritoneal metastases). Systemic delivery of a tumor-specific targeting agent is another objective of this gene therapy strategy. Construction of adenoviral vectors expressing tumor-specific promoters to allow selective gene expression in tumor cells transduced after systemic administration have been accomplished.

EXAMPLE 33

Adenoviral Mediated Delivery of Gastrin Releasing Peptide Receptor Results in Specific Tumor Localization of a Bombesin Analogue In Vivo The abbreviations used are: AdCMVGRPr, recombinant adenoviral vector expressing murine gastrin releasing peptide receptor; AdCMVLacZ, recombinant adenoviral vector expressing the E. coli β-galactosidase gene; AUC, area under the curve; CEA, carcinoembryonic antigen; CMV, cytomegalovirus; i.p., intraperitoneally; [$^{125}$I]-mIP-bombesin, [$^{125}$I]-mIP-Des-Met$^{14}$-bombesin(7–13)NH$_2$; moi, multiplicity of infection; mGRPr, murine gastrin releasing peptide receptor; MRT, mean residence time; PBE, 1% bovine serum albumin and 0.2M ethylenediaminetetraacetic acid in 0.1M phosphate buffered saline, pH 7.2; % ID/g, percent injected dose per gram; pfu, plaque forming units; $t_{1/2}$, half-life.

Radioimmunotherapy is hindered by a variety of factors linked to the utilization of monoclonal antibodies. These limitations include restricted tumor penetration as well as low levels of intratumoral antigen expression. To address the latter problem a gene therapy approach was utilized to induce tumor cells to express enhanced levels of receptor with high binding affinity for a radiolabeled peptide. In this regard, a radiolabeled bombesin analogue was utilized in conjunction with a recombinant adenoviral vector encoding the murine gastrin releasing peptide receptor (AdCMVGRPr). A panel of human carcinoma cell lines were infected in vitro with the AdCMVGRPr vector to examine the induced binding of an $^{125}$I-labeled bombesin peptide. All cell lines examined displayed high levels of induced peptide binding, with approximately 60–80% of the radioactivity bound to the cells, in a live-cell binding assay. The human ovarian carcinoma cell line SKOV3.ip1 was chosen for in vivo analysis of radiolabeled bombesin analogue tumor localization in biodistribution and pharmacokinetic studies in athymic nude mice. Genetic induction of mGRPr in vivo resulted in selective tumor uptake of the radiolabeled peptide and high tumor to blood ratios. The biodistribution results compared favorably to those obtained with $^{131}$I-labeled e21 anti-erbB-2 monoclonal antibody in animals bearing intraperitoneal SKOV3.ip1 tumors which endogenously express erbB-2. Thus, the present invention further demonstrates a novel method to combine gene transfer and radioimmunotherapy to produce augmented tumor cell targeting of radiopharmaceuticals.

Conventional radioimmunotherapy is limited by a number of factors including poor distribution of monoclonal antibodies through solid tumors, generation of host antibodies against the administered antibody, and bone marrow toxicity related to high blood concentrations of radioactivity. In addition, many tumors have heterogeneous and/or low levels of expression of tumor-associated antigens that are the targets for the radiolabeled monoclonal antibody. Therefore, novel approaches aimed at overcoming these limitations are of great importance. To this end, the present invention demonstrates the utility of combining an efficient in situ gene therapy delivery method with a radioimmunotherapy strategy that utilizes a cell surface receptor with a high affinity for a radiolabeled peptide.

Radiolabeled peptides have been utilized in cancer diagnostics for imaging and are being developed to target growth factor receptors such as somatostatin receptors, vasoactive intestinal peptide receptor and epidermal growth factor receptor. Peptides have many advantages over commonly utilized monoclonal antibodies including their small size, high binding affinities, rapid tumor localization, better tumor penetration, rapid blood clearance and higher tumor to normal tissue ratios. To this end, the present invention demonstrated that recombinant adenoviral-mediated delivery of the thyrotropin releasing hormone receptor induced expression in various carcinoma cell types in vitro. This subsequently allowed cells to bind a $^3$H-labeled thyrotropin releasing hormone peptide. However, successful $^{131}$I labeling of the three amino acid peptide for this receptor has not been possible. Therefore, tumor cells were transduced to express a receptor that would have a high binding affinity for a peptide that could be labeled with a therapeutic radionuclide. In this regard, the mGRPr was chosen due to its high binding affinity for the 14 amino acid peptide bombesin. Additionally, endogenous expression of this receptor is limited to a small subset of neuroendocrine cells in the pulmonary and gastrointestinal tracts. Therefore, ultimate clinical utility would not be hindered by localization of the radioisotope to non-tumor targets.

A modified seven amino acid analogue of bombesin was capable of high affinity binding to mGRPr. Importantly, utilization of this modified analogue in vitro resulted in a longer retention time within cells stably transfected to express mGRPr due to less dehalogenation compared to [$^{125}$I]-Tyr-bombesin. Thus, an adenoviral vector-mediated transfer of mGRPr in a panel of human carcinoma cell lines in vitro was employed to demonstrate this approach in a wide variety of tumor types. Additionally, a well characterized murine model of human ovarian carcinoma was genetically induced to express mGRPr in vivo to target the tumor with the radiolabeled bombesin analogue. The biodistribution and pharmacokinetics of the radiolabeled bombesin analogue were analyzed in tumor nodules and a panel of normal organs at various times following injection. This strategy represents a novel manner with which a gene therapy delivery approach may be utilized to sensitize tumor cells to the effects of radioimmunotherapy.

EXAMPLE 34

Cell Lines

The OVCAR-3, U251MG, LS174T, D54MG, A427 and WiDr human carcinoma cell lines were obtained from the American Type Culture Collection (Rockville, Md.). The human ovarian carcinoma cell line OV-4 was obtained from Timothy Eberline, Brigham and Women's Hospital (Boston, Mass.). The human ovarian carcinoma cell line SKOV3.ip1 was obtained from Janet Price, Baylor University (Houston, Tex.). The murine fibroblast cell line, BNR-11, that stably expresses mGRPr was obtained from J. Battey, National Cancer Institute (Bethesda, Md.). All cell lines were maintained in the appropriate culture media supplemented with 10% fetal bovine serum (PAA Laboratories, New Port Beach, Calif.), 200 µg/ml L-glutamine, 100 µg/ml penicillin and 25 µg/ml streptomycin. All cell lines were cultured at 37° C. in a humidified atmosphere with 5% $CO_2$.

EXAMPLE 35

Construction of a Recombinant Adenoviral Vector Encoding the Murine Gastrin Releasing Peptide Receptor The adenovirus expressing mGRPr was prepared employing the standard two plasmid homologous recombination technique of Graham. Briefly, a DNA fragment containing the mGRPr gene (provided by J. Battey, NCI, Bethesda, Md.) was subcloned into the polylinker of the adenoviral shuttle vector pACCMVpLpARS (+) (provided by R. Gerard, Katholieke Universiteit Leuven, Leuven, Belgium). This plasmid provides promoter/initiation signals derived from the CMV early promoter/enhancer and polyadenylation signals from SV40. The resulting recombinant adenovirus shuttle plasmid pAC-mGRPr was employed to derive an E1-deleted, replication-incompetent, recombinant adenovirus employing standard methodologies. Briefly, the shuttle plasmid and the adenoviral packaging plasmid pJM17 (provided by F. Graham, McMaster University, Hamilton, Ontario, Canada) were co-transfected into the E1A trans complementing cell line 293 employing the commercial cationic liposome vector DOTAP (Gibco Life Technologies, Gaithersburg, Md.). Transfected cells were maintained until the onset of cellular cytopathic effects. The newly generated recombinant adenovirus was plaque purified three times. Validation of single plaques was accomplished by direct polymerase chain reaction employing primers specific for mGRPr. The recombinant adenovirus encoding the mGRPr gene, AdCMVGRPr, was expanded within 293 cells and purified by CsCl gradient centrifugation. Genomic DNA derived from the recombinant adenovirus was subjected to digestion with various restriction endonucleases and analyzed by agarose gel electrophoresis. Wild-type adenovirus WT300 (provided by T. Shenk, Princeton University, Princeton, N.J.) was employed as a control for analysis of genomic DNA derived from AdCMVGRPr. Adenoviral vectors were titered within the cell line 293, employing plaque assay techniques for direct determination of viral pfu.

EXAMPLE 36

In Vitro Radiolabeled Binding Assay

Infections with recombinant adenoviruses were performed as previously described. Cells were harvested for radiolabeled binding assay 48 hours following adenoviral mediated infection by removal at 37° C. with 4 mM EDTA, 0.05% KCl. Detached cells were washed once with 0.1% BSA/PBS pH 7.2, enumerated and resuspended at 1×10$^7$ per ml. Each set of cells was aliquoted into 100 µl samples in duplicate polystyrene test tubes following the addition of 100,000 cpm (100 µl) of [$^{125}$I]-Tyr-bombesin (DuPont NEN Research Products, Boston, Mass.). Non-specific binding was determined by the addition of 1000 fold molar excess of unlabeled bombesin. The solutions were mixed at room temperature for 1 hour, rinsed with PBE and centrifuged at 1700×g for 10 min. The supernatant was removed and the cells were counted in a gamma counter to determine the amount of bound radioactivity. Radioactivity bound was then plotted as the percent cpm bound to the cells versus the total amount of cpm added. The human ovarian carcinoma cell line SKOV3.ip1 expresses the cell surface receptor for erbB-2. Therefore, a non-internalizing monoclonal antibody (e21) against a cell surface epitope of erbB-2 was employed (provided by C. Richter King, Oncologix, Inc., Gaithersburg, Md.). The e21 antibody was $^{125}$I-labeled using the Iodogen method and utilized in an in vitro live-cell binding assay with the SKOV3.ip1 cells. Cells were harvested as described above and incubated for 1 hour with 100 µl of a 2 µg/ml solution of $^{125}$I-labeled e21 antibody. Cells were washed and bound radioactivity determined as described above.

EXAMPLE 37

In Vivo Biodistribution of Radiolabeled Peptide

All biodistribution studies were performed in female Balb/c athymic nude mice obtained at 4–5 weeks of age from Frederick Research Laboratory (Frederick, Md.). The peptide mIP-Des-Met-bombesin(7–13)NH$_2$ was synthesized using solid phase peptide synthesis at the UAB Comprehensive Cancer Center Peptide Synthesis and Analysis Shared Facility and has been described elsewhere. Mice were injected i.p. with 2×10$^7$ SKOV3.ip1 human ovarian carcinoma cells. Five days following cell inoculation, mice were injected i.p. with 1×10$^9$ pfu of a recombinant adenoviral vector expressing mGRPr. Animals were then injected i.p. 48 hours later with 2 µCi of [$^{125}$I]-mIP bombesin. Mice were sacrificed at 0.5, 2, 5, 15, 30 min and 1, 4, 8, 12 and 24 hours following peptide injection (n=4–10/group) and the following organs were dissected: blood, heart, lungs, liver, stomach, small intestine, spleen, kidney, skin, bone, muscle, uterus, peritoneal lining and thyroid. In addition, tumor nodules were removed from each mouse. All organs, and tumors were weighed and the activity counted in a gamma counter. The % ID/g for each tissue was calculated except for the thyroid in which only the % ID was determined.

EXAMPLE 38

In Vivo Biodistribution of Radiolabeled Antibody

The e21 antibody was utilized for in vivo biodistribution analysis. Mice were injected i.p. with 2×10$^7$ SKOV3.ip1 human ovarian carcinoma cells and 5 days later injected i.p. with 5 µCi $^{131}$I-labeled e21. Mice were sacrificed at 5 minutes, 1 and 12 hours, and 1, 2, 4 and 6 days following antibody injection (n=6/group). Tumor and normal organs were dissected and analyzed as described above.

EXAMPLE 39

Statistical Analysis

Descriptive statistics were calculated to examine the distribution and variation of time concentration of radiolabeled antibody and peptide, and tissue to blood ratio data (means and standard deviations). Means at each specific time point were calculated from multiple mice data for both tissue concentration and tissue to blood ratios. Mean concentration data (% ID/g) over time was used for pharmacokinetical modeling. The pharmacokinetical parameters were estimated by using the NLIN procedure of Statistical Analysis System programs. Selection of models was based on comparison of Akaike's Information Criterion, the minimization of the model's mean squared error and standard error of the estimated model parameters, and the graphical diagnostics of the model fit.

Two different pharmacokinetic models, a two-compartment elimination model with an absorption phase, were utilized to fit the time concentration curves for the antibody. A two-compartment elimination model was determined to be the best model for bone, kidney, abdominal lining, liver, muscle, small intestine, spleen, stomach, tumor and uterus data. For each of these, the elimination $t_{1/2}$ values for each compartment were calculated along with Cmax and AUC. A one compartment model with an absorption phase was determined the most appropriate for blood, heart, lung and skin data. For each of these, elimination $t_{1/2}$ values were calculated along with $C_{max}$, $T_{max}$ and AUC.

Four different pharmacokinetic models, including one and two compartment elimination models along with one and two-compartment models with an absorption phase were required to fit the time concentration curves for the peptide. A one-compartment elimination model was found to be the best model for bone, heart, liver, spleen, tumor, and uterus data. For each of these, the elimination $t_{1/2}$ was calculated along with $C_{max}$ and AUC. A one-compartment model with an absorption phase was determined to be the best model for abdominal lining and muscle data. For each of these, the elimination $t_{1/2}$ values for each compartment were calculated along with $C_{max}$ and AUC. A two-compartment model with an absorption phase was the best model for blood, kidney, and small intestine data. For each of these, elimination $t_{1/2}$ values for each compartment and the absorption $t_{1/2}$ value was calculated along with $C_{max}$, $T_{max}$ and AUC.

EXAMPLE 40

Infection of Human Carcinoma Cell Lines with a Recombinant Adenoviral Vector Expressing the Murine Gastrin Releasing Peptide Receptor To demonstrate the efficacy of genetically inducing a cell surface receptor on carcinoma cells, a recombinant adenoviral vector encoding the mGRPr under the control of the CMV promoter, AdCMVGRPr, was constructed. The obtained virus was structurally verified through polymerase chain reaction and restriction endonuclease digestion analysis (data not shown). Functional validation of the virus was performed through in vitro gene delivery methods. Human lung, colon and ovarian carcinoma cell lines, along with human glioma cell lines, were infected with 10 or 100 pfu/cell of AdCMVGRPr, or 100 pfu/cell of a control virus, AdCMVLacZ.

Figure 21A:
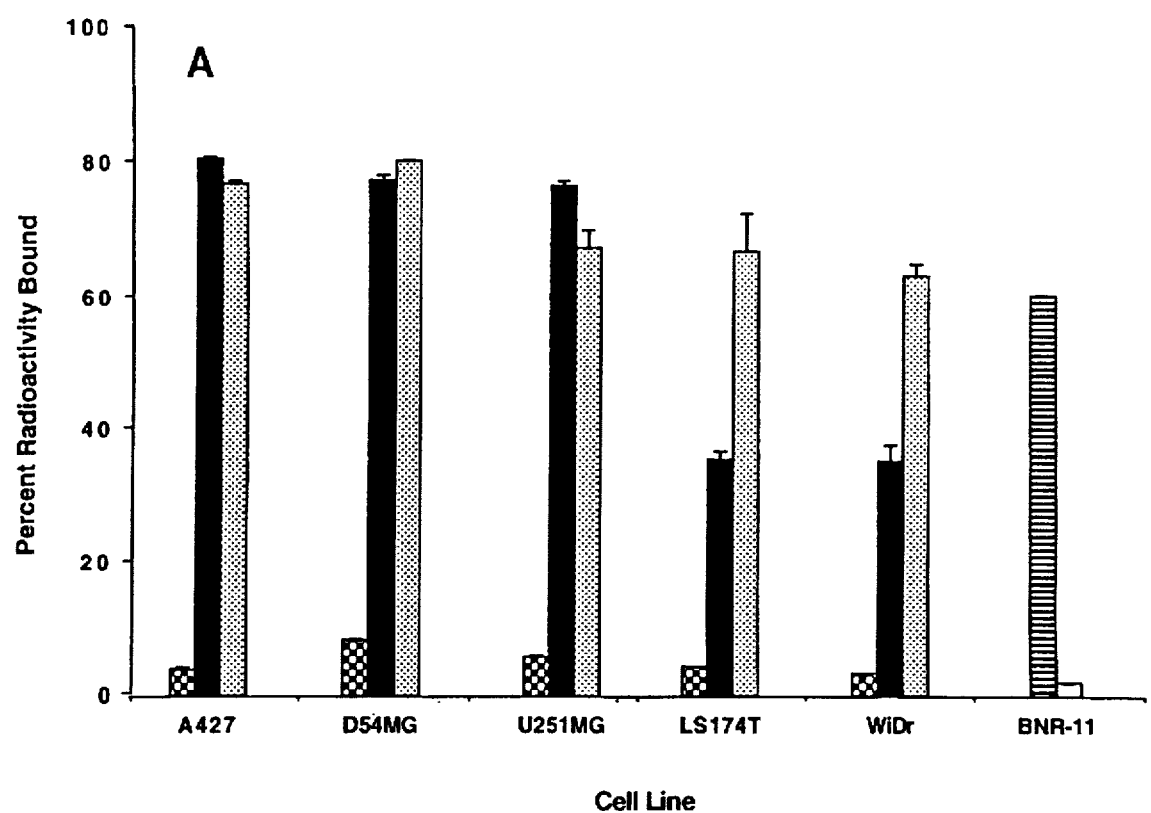
In FIGS. 21A and 21B, cell lines were infected with 10 (■) or 100 (⊟) pfu/cell AdCMVGRPr or 100 pfu/cell ACMVLacZ (◙). Fourty-eight hours following infection, cells were harvested for a live-cell binding assay with [125I]-Tyr4-bombesin and compared to the mouse fibroblast BNR-11 cells that stably express mGRPr.
Figure 21B:
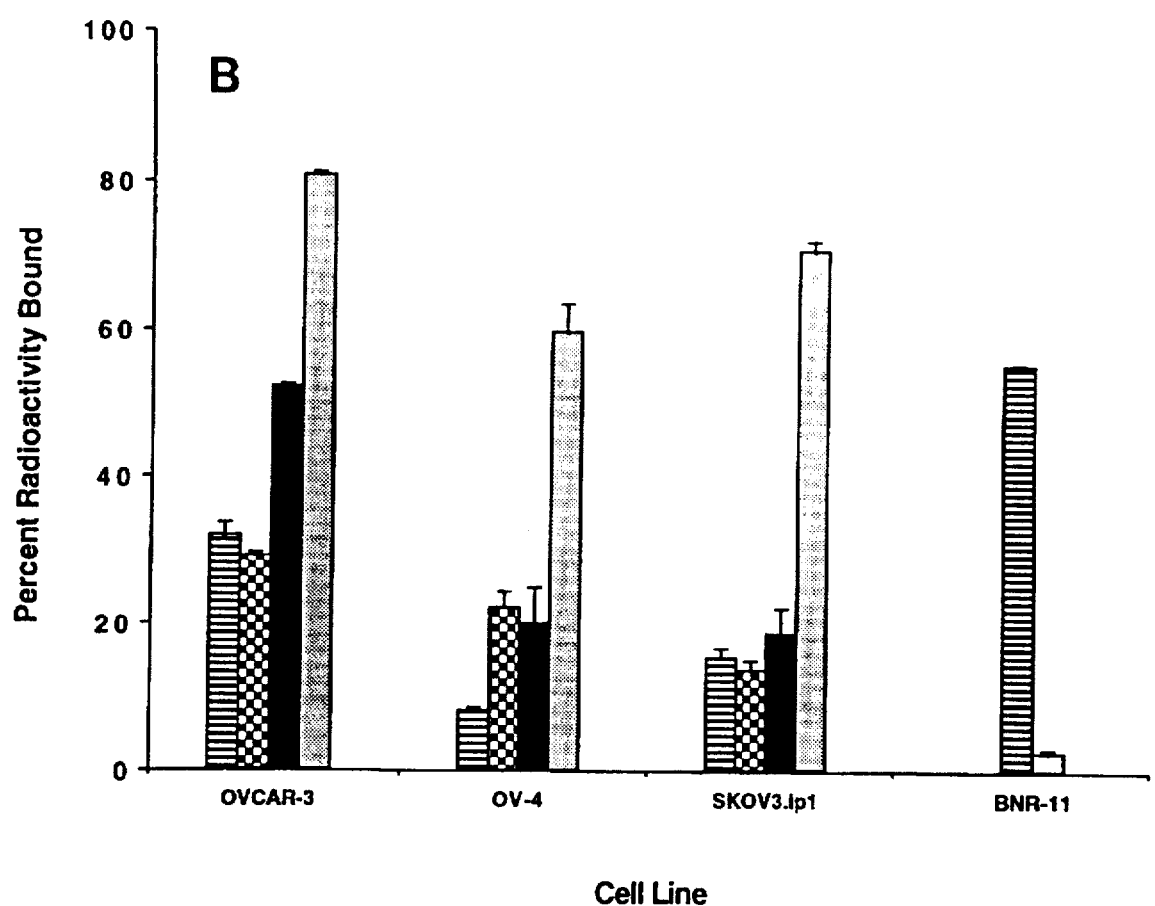
Figure 22A:
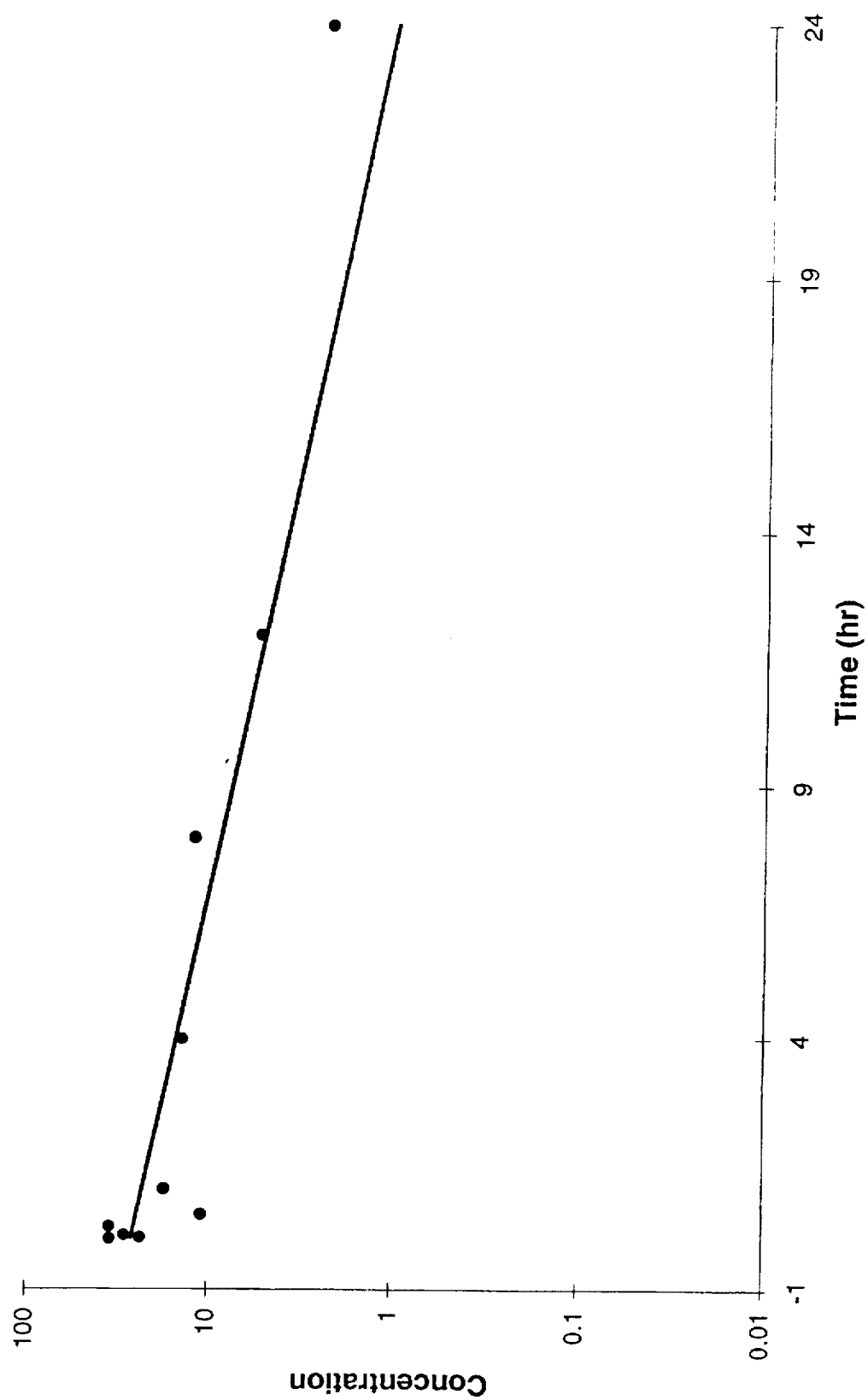
FIG. 22 shows the concentration of [$^{125}$I]-Tyr$_4$-bombesin in tumor (FIG. 22A), blood (FIG. 22B), liver (FIG. 22C) and spleen (FIG. 22D) at various times after injection ($r^2$=0.66 to 0.96). Mice were injected i.p. with $2 \times 10^7$ SKOV3.ip1 human ovarian carcinoma cells. Five days following cell inoculation, mice were injected i.p. with $1 \times 10^9$ pfu of a recombinant adenoviral vector expressing mGRPr. Animals were then injected i.p. 48 hours later with 2 µCi of [$^{125}$I]-mIP-bombesin.
Figure 22B:
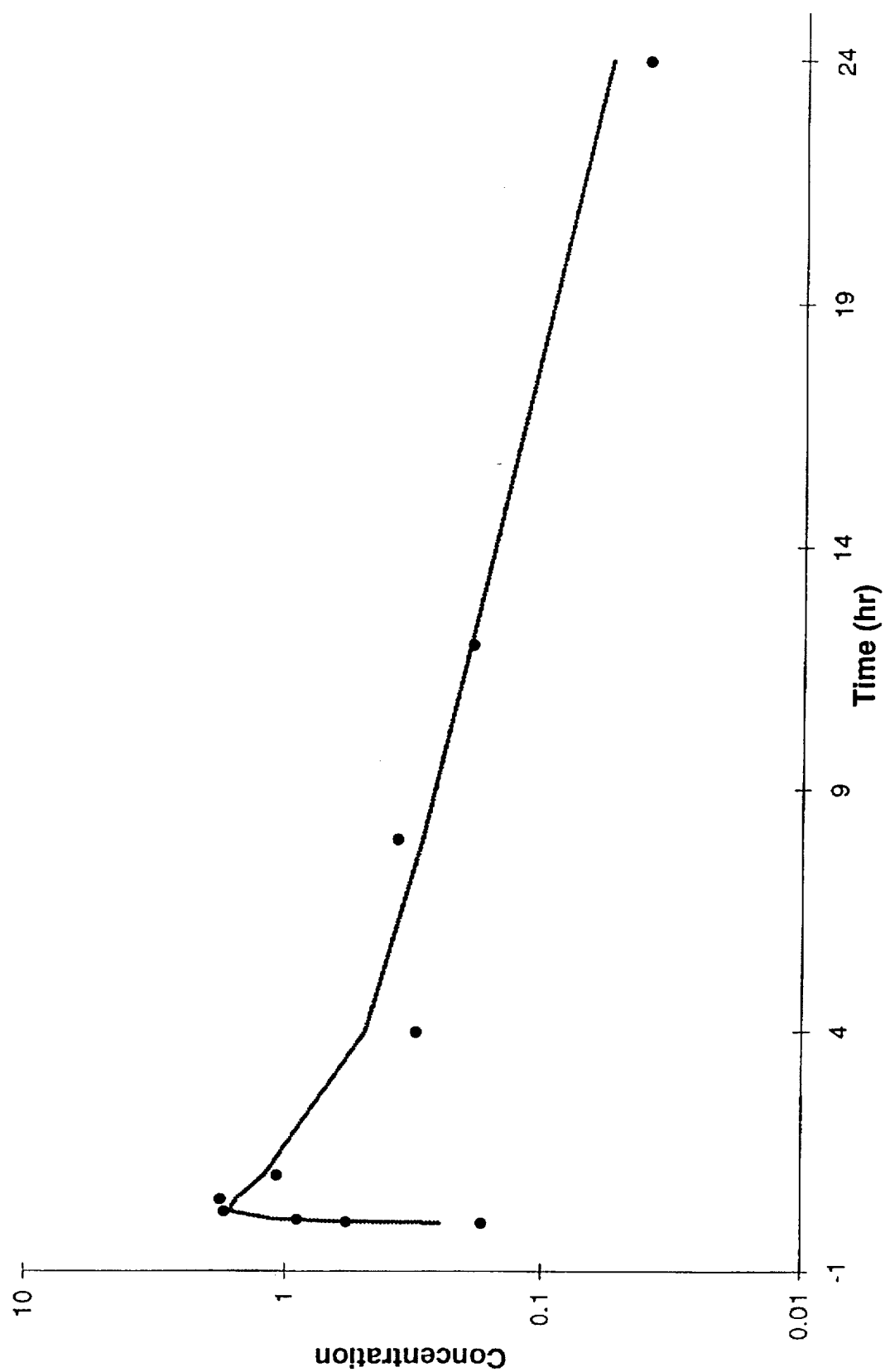
Figure 22C:
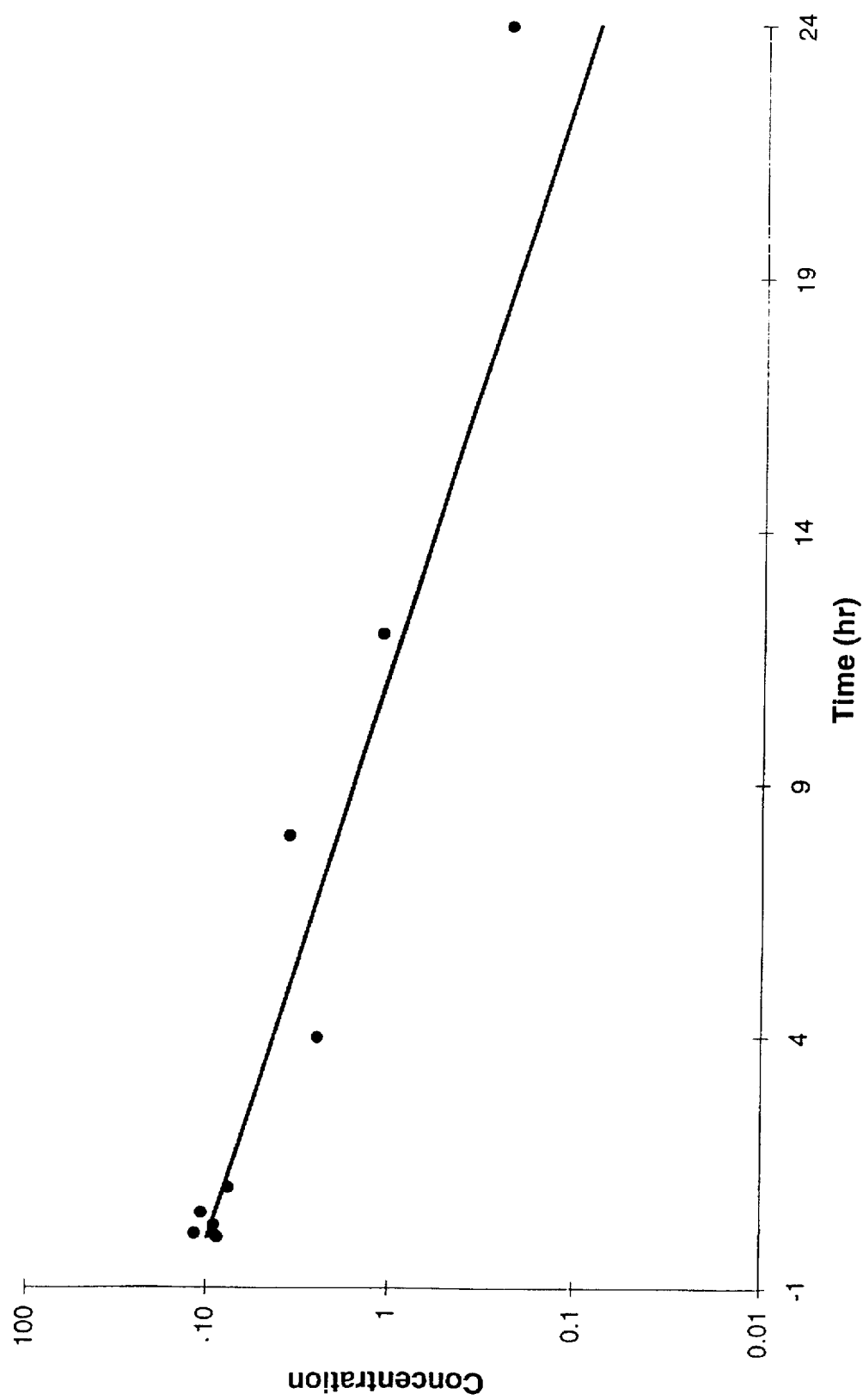
Figure 22D:
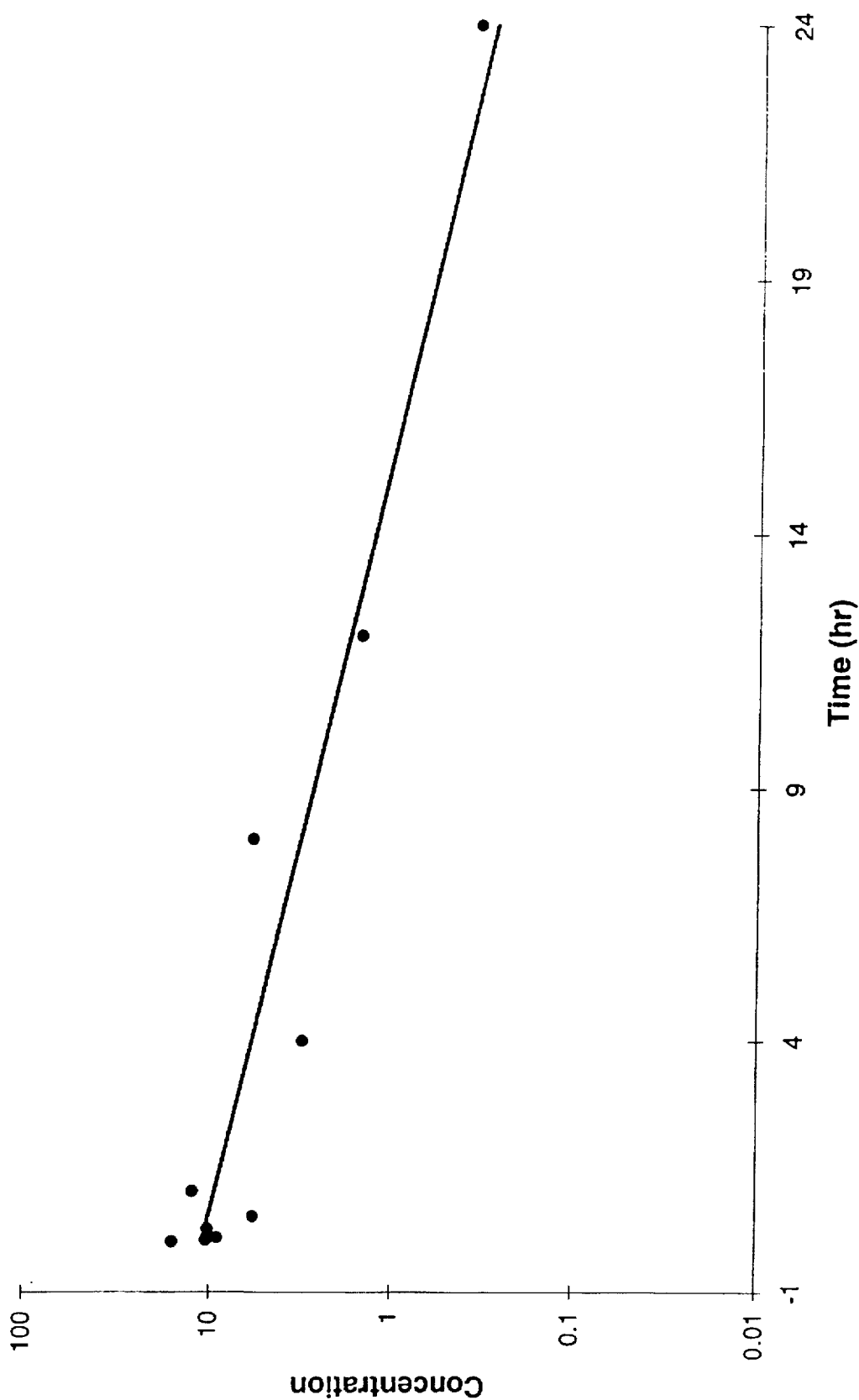

Live-cell binding assays illustrated the ability of each transfected cell line to bind an [$^{125}$I]-Tyr-bombesin peptide (FIGS. 21A and 21B). The non-small cell lung cancer line A427 and the two glioma cell lines D54MG and U251MG demonstrated very high levels of bound radioactivity when infected with either 10 or 100 pfu/cell of the AdCMVGRPr vector with 64.6–77.2% of added radioactivity bound to the cells. Similarly, the two human colon carcinoma cell lines, LS174T and WiDr demonstrated 60% binding of the radiolabeled bombesin peptide following infection with 100 pfu/cell AdCMVGRPr. However, transfection of these colon carcinoma cells with 10 pfu/cell AdCMVGRPr resulted in only approximately 30% of the added radioactivity bound (FIG. 21A). These results indicate that some cell lines may have a dose dependent response to increasing moi with recombinant adenoviral vectors. The values obtained for these cell lines were comparable to the BNR-11 positive control cell line generated to stably express mGRPr. In marked contrast, all human glioma cell lines infected with the AdCMVLacZ virus demonstrated only 3–8% binding of the radiolabeled peptide, indicating that infection of the cells with AdCMVGRPr selectively induced receptor expression and subsequent binding by the radiolabeled bombesin peptide.

To further demonstrate the applicability of this approach, a panel of human ovarian carcinoma cell lines were tested for the ability to bind [$^{125}$I]-Tyr-bombesin following AdCMVGRPr infection. The cell lines OVCAR-3, OV-4 and SKOV3.ip1 were infected with 10 or 100 pfu/cell of AdCMVGRPr, 100 pfu/cell of AdCMVLacZ or left uninfected (FIG. 21B). Uninfected OVCAR-3 cells demonstrated binding of 32% of the added radioactivity, however, infection with 10 or 100 pfu/cell of AdCMVGRPr resulted in an increase of binding to 52.1% and 80.9%, respectively. The OV-4 and SKOV3.ip1 cells showed similar binding at 10 pfu/cell of 20% and 18.4% respectively. Increasing the moi to 100 resulted in an increased binding of radioactivity in both instances with OV-4 cells binding 59.7% and SKOV3.ip1 cells binding 70.6%. Therefore, ovarian carcinoma cell lines were also induced to express mGRPr following AdCMVGRPr infection and bound radiolabeled bombesin. In contrast, infection of the ovarian carcinoma cells with the control virus AdCMVLacZ did not increase binding over that obtained with uninfected cells, except for an unknown reason in the instance of the OV-4 cells. Therefore, it is likely that a wide variety of tumor types will be amenable to genetic radioisotope targeting strategies.

The efficacy of the genetic isotope targeting strategy of the present invention was compared to a more standard radioimmunotherapy approach utilizing a monoclonal antibody directed against the cell surface receptor erbB-2. The human ovarian carcinoma cell line SKOV3.ip1 is known to overexpress erbB-2 and was therefore utilized in a live-cell binding assay. Incubation of the SKOV3.ip1 cells with $^{125}$I-labeled e21 resulted in 96.3% of the total radioactivity bound to the cells (data not shown). This indicated that these carcinoma cells were highly reactive to the e21 antibody and that both this cell line and the e21 antibody were suitable for in vivo analysis.

EXAMPLE 41

Biodistribution of [$^{125}$I]-mIP-bombesin and $^{131}$I-labeled e21 Antibody

The modified bombesin analogue, [$^{125}$I]-mIP-bombesin, was utilized for this in vivo study since the tumor localization of [$^{125}$I]-mIP-bombesin at 4 hours post injection was much greater than the localization of [$^{125}$I]-Tyr-bombesin. The biodistribution and pharmacokinetic profile of this bombesin analogue was characterized. In addition, a comparison to a radiolabeled monoclonal antibody was undertaken.

The pharmacokinetic parameters and representative curves for the biodistribution of [$^{125}$I]-mIP bombesin in tumor bearing athymic nude mice are shown in Table 5 and FIG. 22. In these studies, mice were injected i.p. with SKOV3.ip1 i.p. tumor cells and subsequently injected i.p. with AdCMVGRPr 5 days later. [$^{125}$I]-mIP-bombesin was administered 48 h after AdCMVGRPr and the results are presented for a one-compartment model. The highest concentration of [$^{125}$I] mIP-bombesin in tumor was 33.6±18.2% ID/g at 30 sec after injection which declined to 2.5±2.8% ID/g at 24 hours after injection (FIG. 22A). The clearance half-life for tumor of the radiolabeled bombesin analogue was 5.2 hours, while the $t_{1/2\beta}$ for blood was 6.7 hours (FIG. 22B). The clearance half-life for other tissues ranged from 3.7 to 11.7 hours (FIGS. 22C and 22D).

TABLE 5

Pharmacokinetic parameters for biodistribution of $^{125}$I-mIP bombesin in athymic nude mice bearing SKOV3.ip1 tumors infected to express AdCMVGRPr

|  | $C_{max}$ | Tmax | $t_{1/2Ab}$ | $t_{1/2\alpha}$ | $t_{1/2\beta}$ | AUC |
|---|---|---|---|---|---|---|
| Abdominal lining | 47.7 | — | — | 0.1 | 6.5 | 160.9 |
| Blood | 1.5 | 0.6 | 0.07 | 0.8 | 6.7 | 8.0 |
| Bone | 1.1 | — | — | — | 7.9 | 12.8 |
| Heart | 0.9 | — | — | — | 6.6 | 8.3 |
| Kidney | 15.3 | 0.5 | 0.1 | 0.4 | 4.7 | 44.8 |
| Liver | 9.8 | — | — | — | 3.5 | 49.2 |
| Lung | 1.3 | 0.05 | 0.01 | — | 4.1 | 7.6 |
| Muscle | 3.6 | — | — | 0.6 | 7.7 | 12.4 |
| Skin | 1.0 | 0.4 | 0.07 | — | 3.7 | 5.9 |
| Small Intestine | 41.7 | 0.3 | 0.06 | 0.6 | 8.3 | 112 |
| Spleen | 10.9 | — | — | — | 4.6 | 71.7 |
| Stomach | 10.2 | 0.05 | 0.004 | — | 11.7 | 172.3 |
| Tumor | 25.6 | — | — | — | 5.2 | 193.1 |
| Uterus | 29.2 | — | — | — | 4.3 | 182.8 |

$C_{max}$ is given in percent ID/g; $T_{max}$ in hours; $t_{1/2Ab}$ in hours; $t_{1/2\alpha}$ in hours; $t_{1/2\beta}$ in hours; AUC is in percent ID × h/g.

Figure 23A:
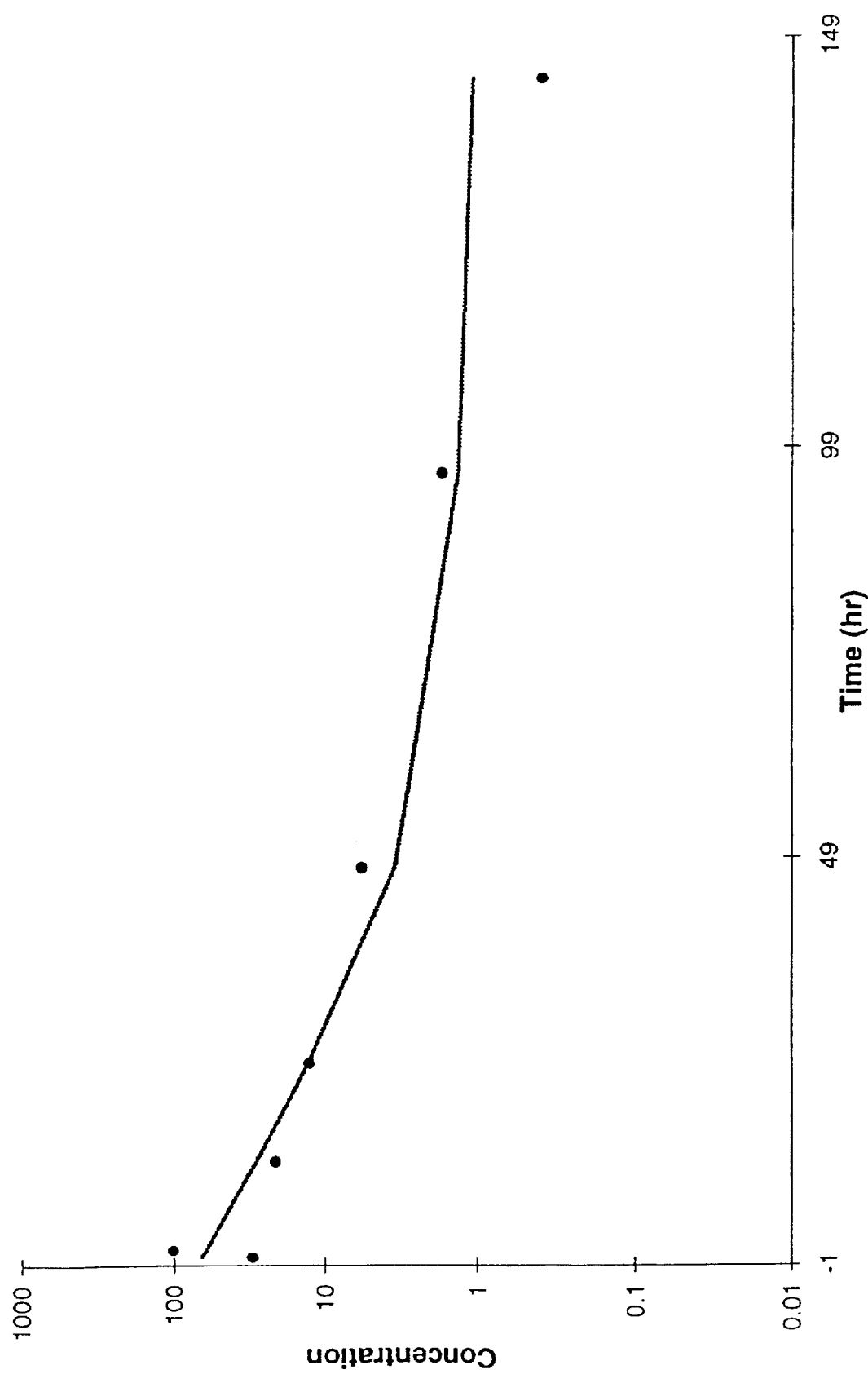
FIG. 23 shows the concentration of $^{131}$I-labeled e21 anti-erbB-2 monoclonal antibody in tumor (FIG. 23A), blood (FIG. 23B), liver (FIG. 23C) and spleen (FIG. 23D) at various times after injection ($r^2$=0.61 to 0.95). Mice were injected i.p. with $2 \times 10^7$ SKOV3.ip1 human ovarian carcinoma cells and 5 days later injected i.p. with 5 µCi of [$^{131}$I]-e21.
Figure 23B:
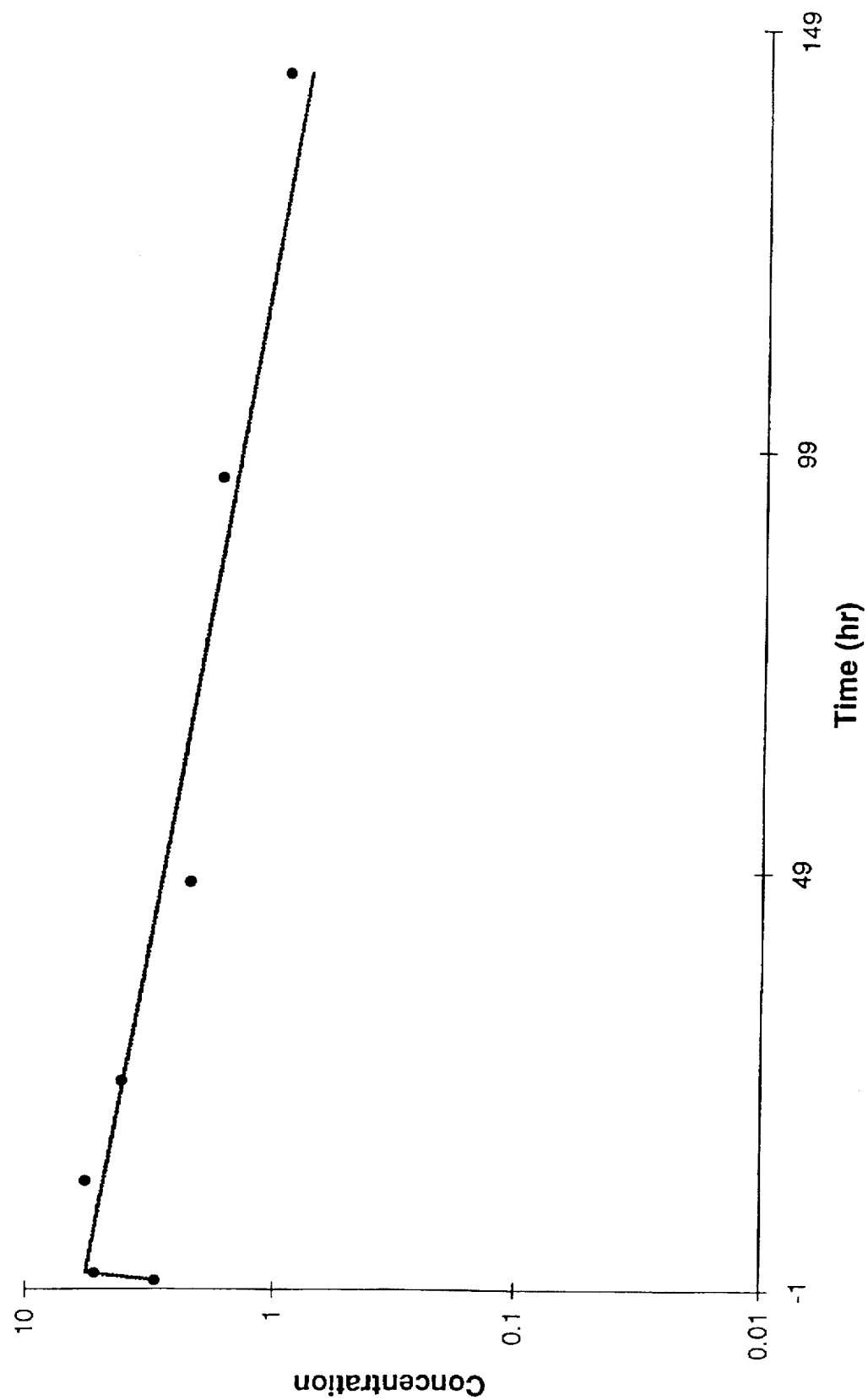
Figure 43C:
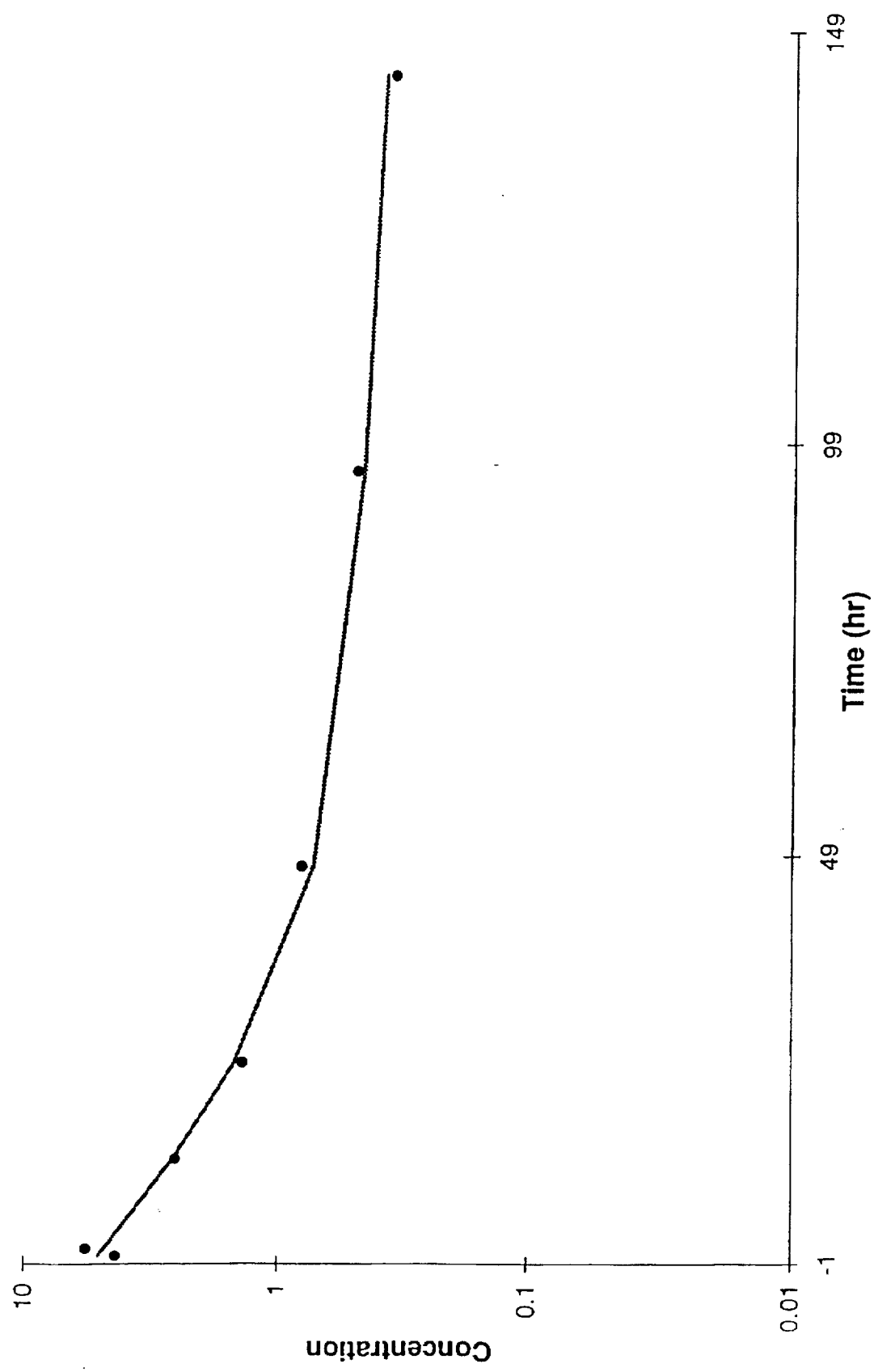
Figure 23D:
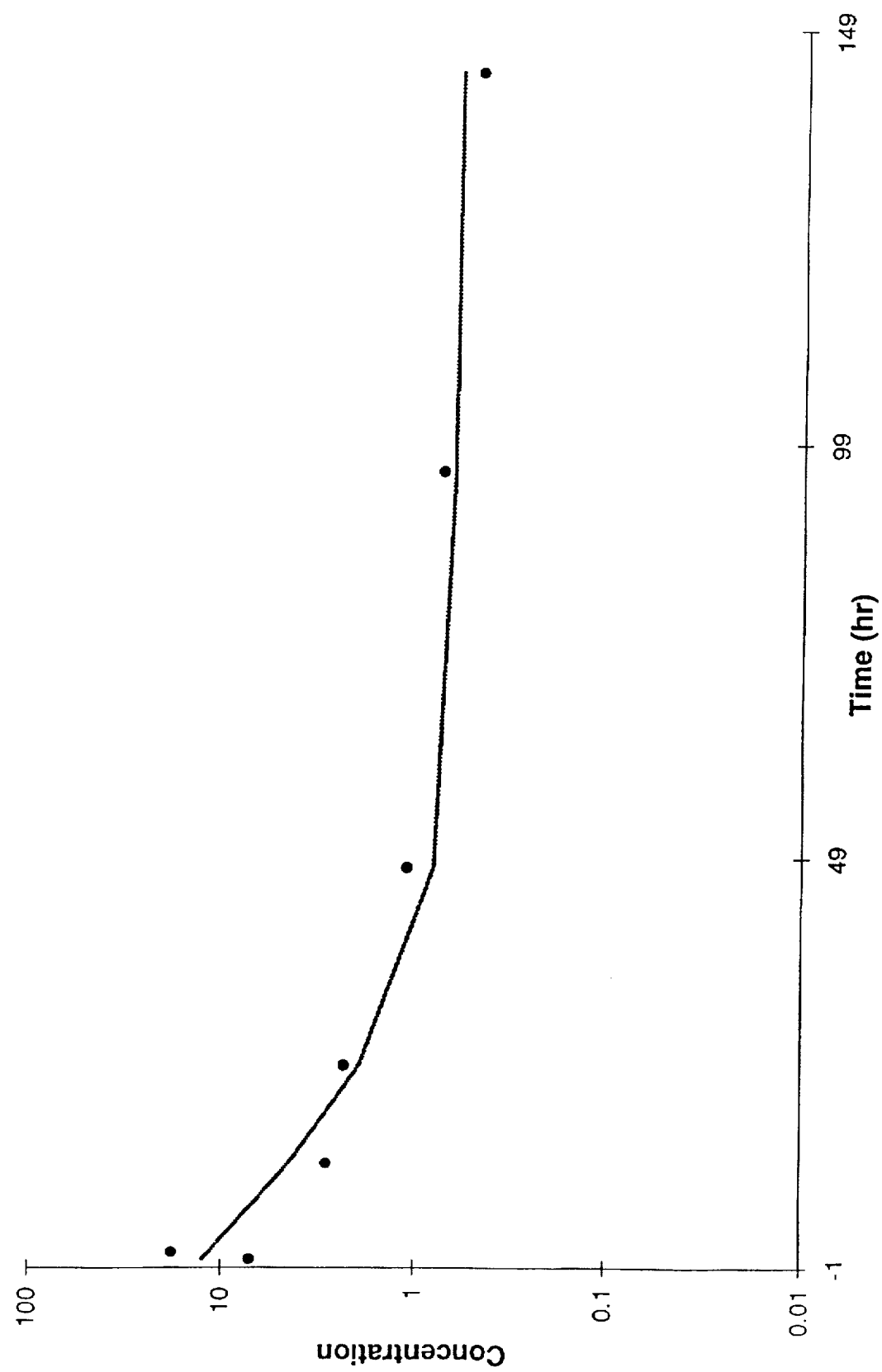
Figure 24:
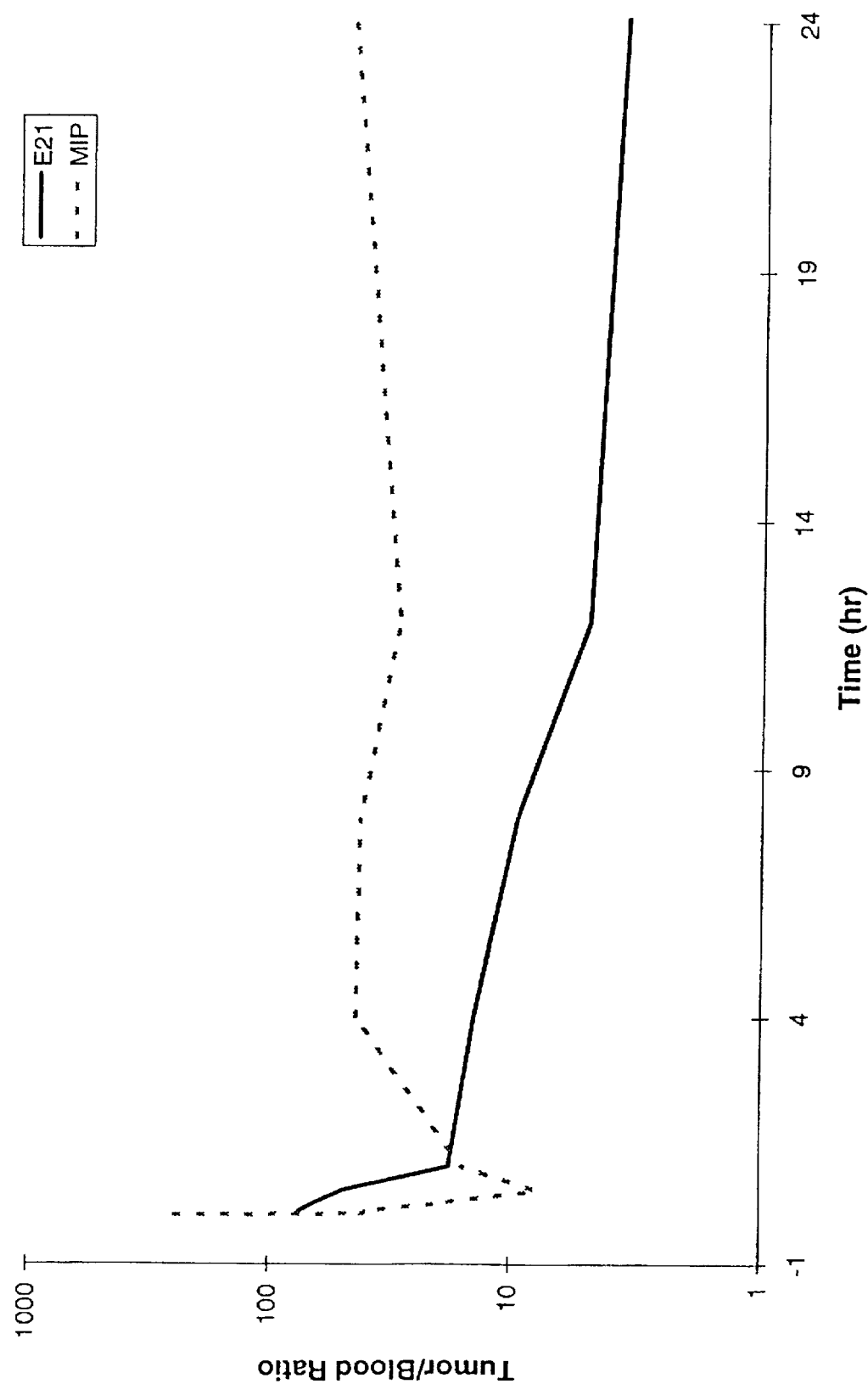
FIG. 24 shows the tumor to blood ratios of [$^{125}$I]-mIP-bombesin and [$^{131}$I]-e21 monoclonal antibody in athymic nude mice.

The pharmacokinetic parameters and representative curves for the $^{131}$I-labeled e21 anti-erbB-2 monoclonal antibody administered i.p. to animals bearing 7-day old SKOV3.ip1 tumors without AdCMVGRPr infection are shown in Table 6 and FIG. 23. The clearance $t_{1/2\beta}$ for tumor (199.5 hours) and $t_{1/2}$ blood (49.6 hours) were considerably longer than the values obtained with [$^{125}$I] mIP-bombesin (FIGS. 23A and 23B). The clearance half-life of the antibody for other tissues were considerably longer than values obtained with the radiolabeled bombesin analogue (Table 6). The highest concentration of e21 antibody in tumor was 100.7±82.1% ID/g at 1 hour after injection. This value declined to 12.8±5.7% ID/g by 24 hours. The tumor to blood ratios at various times post-injection for the radiolabeled bombesin analogue and the e21 antibody are shown in FIG. 24. The peak tumor to blood ratio for the bombesin analogue was 12.6-fold higher than for the antibody. For [$^{125}$I]-mIP-bombesin, the tumor to blood ratio dropped after the initial peak and then rose to a level of about 50 (FIG. 24A). For the e21 antibody, the peak tumor to blood ratio occurred at 1 hour after i.p. injection, and then decreased to a ratio of less than 4 (FIG. 24B). The tumor to blood ratio for the bombesin analogue was 24.8- and 15.4-fold higher than the antibody at 30 sec and 24 hours respectively, principally due to the lower blood concentration and more rapid clearance of the radiolabeled bombesin analogue from blood compared to the antibody. Thus, these results support the concept that utilization of a radiolabeled peptide would limit the bone marrow toxicity problem encountered with radiolabeled monoclonal antibodies that circulate in the blood for long periods of time.

TABLE 6

Pharmacokinetic parameters for biodistribution of $^{131}$I-e21 monoclonal antibody in athymic nude mice bearing SKOV3.ip1 tumors

|  | $C_{max}$ | Tmax | $t_{1/2Ab}$ | $t_{1/2\alpha}$ | $t_{1/2\beta}$ | AUC |
|---|---|---|---|---|---|---|
| Abdominal lining | 16.4 | — | — | 6.1 | 5109.3 | 3790.1 |
| Blood | 5.7 | 0.7 | 0.08 | — | 49.6 | 413.4 |
| Bone | 1.6 | — | — | 8.4 | 271.2 | 207.9 |
| Heart | 2.0 | 1.0 | 0.1 | — | 170.3 | 210.3 |
| Kidney | 3.5 | — | — | 10.0 | 190.2 | 244.9 |
| Liver | 5.2 | — | — | 10.4 | 190.2 | 244.9 |

TABLE 6-continued

Pharmacokinetic parameters for biodistribution of $^{131}$I-e21 monoclonal antibody in athymic nude mice bearing SKOV3.ip1 tumors

|  | $C_{max}$ | Tmax | $t_{½Ab}$ | $t_{½α}$ | $t_{½β}$ | AUC |
|---|---|---|---|---|---|---|
| Lung | 3.5 | 0.7 | 0.08 | — | 36.9 | 188.4 |
| Muscle | 1.7 | — | — | 13.5 | 13.5 | 693.0 |
| Skin | 3.7 | 1.8 | 0.3 | — | 28.1 | 155.3 |
| Small Intestine | 5.3 | — | — | 6.6 | 73.1 | 117.9 |
| Spleen | 12.5 | — | — | 7.4 | 633.3 | 784.1 |
| Stomach | 21.0 | — | — | 11.1 | ND[a] | 388.4[b] |
| Tumor | 64.6 | — | — | 9.7 | 199.5 | 1413.0 |
| Uterus | 13.1 | — | — | 14.4 | ND | 329.0 |

[a]ND, not defined
[b]AUC calculated by integrating the plasma time concentration curve from 0 to 144 hours since elimination in the second compartment was 0.

Human ovarian carcinoma results in the most deaths from gynecologic malignancies in the United States. Women frequently present with end-stage disease confined within the peritoneal cavity. In a murine model of peritoneal tumor, Rowlinson et al. demonstrated that i.p. delivery of a radiolabeled monoclonal antibody resulted in about a 50-fold advantage in tumor uptake when compared to intravenous administration, and higher tumor/blood ratios were seen at early time points with regional administration. Additionally, i.p. delivery has been demonstrated to be more efficient in women with ovarian carcinoma. Therefore, regional treatment of ovarian carcinoma with i.p. delivery of radiolabeled ligands is the preferred route of administration. Additionally, a variety of gene therapy strategies have recently been undertaken for the treatment of ovarian carcinoma; recombinant adenoviral vectors are highly efficient at in situ transduction of peritoneal ovarian tumor with greater than 80% of the tumor cells expressing the transgene. Moreover, a well characterized murine model of human ovarian carcinoma has been developed and utilized for a variety of gene therapy approaches. To this end, peritoneal tumor cell death has been accomplished with i.p. delivery of recombinant adenoviral vectors expressing either an intracellular single-chain antibody directed against the cell surface receptor erbB-2 or the herpes simplex virus thymidine kinase gene. In both instances a therapeutic effect was elicited, with reduced tumor burden and prolonged survival indicting that sufficient tumor cell transduction had been accomplished. However, no evidence of complete remission was demonstrated in either instance, therefore, methods to enhance current gene therapy strategies are warranted.

Strategies to amplify the biologic effects of genetic transduction events would potentially allow enhanced therapeutic efficacy of gene therapy methods. By linking tumor transduction to induced binding of radiolabeled peptides, this effect may be achieved since cells in proximity to bound ligand may be killed as a result of exposure to the local radiation field. When used with radiation therapy, uniform systemic incorporation of the genetic construct into tumor cells may not be necessary. Therefore, the use of genetic induction of a receptor and targeting of a radiolabeled peptide was combined. The present invention is the first comprehensive examination of the pharmacokinetics of in vivo localization using this approach.

Conventional radioimmunotherapy has typically utilized monoclonal antibodies directed against tumor-associated antigens. The major limitations of this approach include low tumor uptake and high blood concentrations of radiolabeled antibody contributing to bone marrow toxicity, and lack of homogeneous tumor distribution. Additionally, patients develop an immune response against the administered antibody. In an effort to overcome the low level antigen expression problem, the utility of systemically administered cytokines for upregulating the expression of tumor-associated antigens, which has resulted in increased localization of radiolabeled antibodies in both animal models and patients, has been investigated. In the present invention, a gene transfer method was utilized to genetically induce the expression of a cell surface protein specifically on tumor cells to produce increased localization of radiolabeled ligand. In this regard, tumor cells can be genetically induced to express a non-endogenous surface receptor. The present invention demonstrated that it was possible to express CEA via intratumoral inoculation of D54MG subcutaneous glioma xenografts with an adenoviral vector expressing CEA. These infected tumor nodules were successfully able to localize $^{131}$I-labeled anti-CEA antibody at a level equivalent to human colon cancer xenografts naturally expressing CEA, in comparison to animals injected with the control AdCMVLacZ virus which did not demonstrate antibody uptake. Thus, the present invention showed that in vivo transduction of tumor was possible, and that this transduction would result in the expression of a non-endogenous cell surface receptor targeted by a radiolabeled monoclonal antibody.

The clinical utilization of monoclonal antibodies, however, is still going to elicit problems related to poor tumor penetration and bone marrow toxicity as described above. Additionally, the present invention showed that utilization of the $^{131}$I-labeled e21 monoclonal antibody resulted in a longer clearance half-life from blood and normal tissues when compared to the radiolabeled bombesin analogue. Peptides offer many advantages over antibodies including high affinity binding, high vascular permeability, rapid tumor localization and better tumor penetration. Furthermore, peptides have rapid blood clearance, and lower immunogenicity. Additionally, it was shown that [$^{125}$I]-mIP-bombesin resulted in higher internalization and longer intracellular retention in mGRPr expressing cells when compared to [$^{125}$I]-Tyr-bombesin. Thus, the higher tumor uptake of the bombesin analogue in vivo may have been a result of its higher degree of internalization and longer intracellular residence time. Through efficient in situ gene transfer, the results illustrate preferential transduction of tumor cells intraperitoneally and selective uptake and retention of [$^{125}$I]-mIP-bombesin. In addition, comparison with an $^{131}$I-labeled monoclonal antibody, reactive- with the erbB-2 antigen on the human ovarian carcinoma cell line SKOV3.ip1, demonstrated that higher tumor to blood ratios were obtained with the radiolabeled peptide. Thus, the present invention demonstrated the utility of in vivo transduction of tumor with new receptors to serve as a target for radiolabeled peptide therapy.

The following references were cited herein:
1. Kaminski, M. S., et al., *N. Engl. J. Med.*, 329:459–465, 1993.
2. Press, O. W., et al., *N. Engl. J. Med.*, 329:1219–1224, 1993.
3. Goldenberg, D. M., et al., *Sem. Cancer Biol.*, 1:217–225, 1990.
4. Blumenthal, R. D., et al., *Int. J. Cancer*, 52:1–7, 1992.
5. Buchsbaum, D. J., et al., *Med. Phys.*, 20:551–567, 1993.
6. Buchsbaum, D. J., In: D. M. Goldenberg (ed.), Cancer Therapy with Radiolabeled Antibodies, 115–140, Boca Raton: CRC Press, 1995.
7. Wahl, R. L., *Cancer*, 73:989–992, 1994.
8. Buchsbaum, D., *Antibody, Immunocon. Radioph.*, 4:693–701,1991. 9.

9. Scheinberg, D., et al., *Cancer Res.* (Suppl) 50:962s–963s, 1990.
10. Meredith, R. F., et al., *J. Nucl. Med.*, 35:1017–1022, 1994.
11. Welt, S., et al., *J. Clin. Oncol.*, 12:1561–1571, 1994.
12. Goldenberg, D. M., *Am. J. Med.*, 94:297–312, 1993.
13. Meredith, R. F., et al., *J. Nucl. Med.* 33:23–29, 1992.
14. Buchsbaum, D. J., et al., *Antibody, Immunoconj. Radiopharm.* 4:245–272, 1991.
15. Kvols, L. K., et al., *N. Engl. J. Med.*, 315:663, 1986.
16. Fischman, A. J., et al., *J. Nucl Med.*, 34:2253–2263, 1993.
17. Buchegger, F., et al., *J. Nucl. Med.*, 31, 1035, 1990.
18. Sharkey, R. M., et al., *J. Natl. Cancer Inst.*, 83, 627, 1991.
19. Yokota, T., et al., *Cancer Res.*, 52, 3402, 1992.
20. Bender, H., et al., *Cancer Res.*, 52, 121, 1992.
21. Colapinto, E. V., et al., *Cancer Res.*, 50, 1822, 1990.
22. Milenic, D. E., et al., *Cancer Res.*, 51, 6363, 1991.
23. Rowlinson, G., et al., *Cancer Res.*, 47, 6528, 1987.
24. Stewart, J. S. W., et al., *Int. J. Radiat. Oncol. Biol.*, 16, 405, 1989.
25. Zalutsky, M. R., et al., *Cancer Res.*, 50, 4105, 1990.
26. Kozak, R. W., et al., *Cancer Res.*, 49, 2639, 1989.
27. Quadri, S. M., et al., *J. Nucl. Med.*, 34:938–945, 1993.
28. Greiner, J. W., et al., *Cancer Res.*, 53, 600, 1993.
29. Kuhn, J. A., et al., *Cancer Res.*, 51, 2335, 1991.
30. Shrivastav, S., et al., *J. Int. Radiat. Oncol. Biol.*, 16, 721, 1989.
31. Msirikale, J. S., et al., *J. Int. Radiat. Oncol. Biol.*, 13, 1839, 1987.
32. Kalofonos, H., et al., *Cancer Res.*, 50, 159, 1990.
33. Blumenthal, R. D., et al., *Cancer Res.*, 48, 5403, 1988.
34. Blumenthal, R. D., et al., *J. Natl. Cancer Inst.*, 84, 399, 1992.
35. Morton, B. A., et al., *Cancer Res.* (Suppl.), 50, 1008s, 1990.
36. Mausner, L. F., et al., *Med. Phys.*, 20:503–509, 1993.
37. Bradley, E. W., et al., *Radiat. Res.* 64:555–563, 1975.
38. Chan, P. C., et al., *Radiat. Res.* 67:332–343, 1976.
39. Kassis, A. I., et al., *Radiat. Res.* 90:362–373, 1982.
40. Adelstein, S. J., et al., *Nucl. Med. Biol.* 14:165–169, 1987.
41. Wessels, B. W., et al., *Med. Phys.* 11:638–645, 1984.
42. Jain, R. K., et al., *Cancer Res.*, 48, 7022, 1988.
43. Fujimori, K., et al., *Cancer Res.*, 49, 5656, 1989.
44. Jain, R. K., *Cancer Metastasis Rev.*, 9, 253, 1990.
45. Jain, R. K., *J. Int. Radiat. Biol.*, 60, 85, 1991.
46. Andrew, S. M., et al., *Cancer Res.*, 50, 5225, 1990.
47. Sands, H., et al., *Cancer Res.*, 48, 88, 1988.
48. Sung, C., et al., *Cancer Res.*, 52:377–384, 1992.
49. Jones, P. L., et al., *Cancer Immunol. Immunother.*, 22:139–143, 1986.
50. Pervez, A., et al., *Int. J. Cancer* 3 (Suppl.):23–29, 1988.
51. Ong, G. K., et al., *Cancer Res.*, 49:4264–4273, 1989.
52. Del Vecchio, S., et al., *Cancer Res.*, 49:2783–2789, 1989.
53. Blumenthal, R. D., et al., *Cancer Imm. Immunother.*, 33:351–358,1991.
54. Shockley, T. R., et al., *Cancer Res.*, 52:367–376, 1992.
55. Buchsbaum, D. J., et al., In: Targeted Diagnosis and Therapy, J. Rodwell (ed), Vol. III. Targeted Therapeutic Systems, P. Tyle and B. P. Ram (eds), Marcel Dekker, Inc., NY, pp. 215–255, 1990.
56. Bigler, R. E., et al., *NATO ASI Series*, Vol. 152, Plenum Press, NY 1987), pp 409–428.
57. Wilbur, D. S., *Antibody Immunconj. Radiopharm.*, 4:85–97, 1990.
58. Buchsbaum, D. J., et al., *Int. J. Radiat. Oncol. Biol.*, 25:629–638,1993.
59. Roselli, M., et al., *J. Nucl. Med.*, 30:672–682, 1989.
60. Washburn, L. C., et al., *Nucl. Med. Biol.*, 18:313–321, 1991.
61. Sharkey, R. M., et al., *Cancer Res.*, 50:2330–2336, 1990.
62. Deshpande, S. V., et al., *J. Nucl. Med.*, 31:473–479, 1990.
63. Meares, C. F., et al., *Bioconjugate Chem.*, 2:187–194, 1991.
64. Vriesendorp, H. M., et al., *Int. J. Radiat. Oncol. Biol.*, 17:815–821, 1989.
65. Eary, J. F., et al., *Clin. Nucl. Med.*, 15:911–916, 1990.
66. Breitz, H. B., et al., *J. Nucl. Med.*, 33:1099–1112, 1992.
67. Breitz, H., et al., *J. Nucl. Med.*, 31:724–725, 1990.
68. Kassis, A. I., et al., *Radiat. Res.*, 105:27–36, 1986.
69. Kurtzman, S. H., et al., *J. Natl. Cancer Inst.*, 80:449–452, 1988.
70. Mitchell, J. B., et al., *Radiat. Res.*, 79:552–567, 1979.
71. Hall, E., *Radiobiology for the Radiologist*, 3rd Ed. pp. 126–128. Lippincott, Philadelphia, 1988.
72. Hall, E., *Radiobiology for the Radiologist*, 3rd Ed. pp. 162–177. Lippincott, Philadelphia, 1988.
73. Atcher, R. W., et al., *Soc. of Nucl Med.*, meeting, 1987.
74. Williams, J. R., et al., *Int. J. Radiat. Oncol. Biol. Phys.*, 24:699–704, 1992.
75. Atcher, R. W., et al., *Int. J. Rad. Appl. Instrum. A.*, 39:283–286, 1988.
76. Bloomer, W. D., et al., *Int. J. Radiat. Oncol. Biol. Phys.*, 10:341–348, 1984.
77. Link, E. M., et al., *Cancer Res.*, 50:2693–2697, 1990.
78. Zalutsky, M. R., et al., *Cancer Res.*, 54:4719–4725, 1994.
79. Macklis, R., et al., *Science*, 240:1024–1026, 1988.
80. Kozak, R. W., et al., *Proc. Nat. Acad. Sci.*, 83:474–478, 1986.
81. Brown, I., *Appl. Radiat. Isot.*, 37:789–798, 1986.
82. Roeske, J., et al., *Int. J. Radiat. Oncol. Biol. Phys.*, 9:1539–1548, 1990.
83. Gansow, O. A., et al., In Knapp, F. F. (Ed.) *New Radionuclide Generator Systems for Use in Nuclear Medicine*, ACS, Washington, D.C., 1984.
84. Kumar, K. et al., *J. Chem. Soc. Chem. Commun.*, 145, 1989.
85. Clem, R., et al., *J. Labelled Compd. Radiopharm.*, 1991.
86. Mirzadeh, S., et al., *Radiochim. Acta*, 60:1–10, 1993.
87. Ruegg, C. L., et al., *Cancer Res.*, 50:4221–4226, 1990.
88. Schally, A. V., et al., *Ann. Rev. Biochem.*, 47:89–128, 1978.
89. Falck-Pedersen, E., et al., *Molecular Pharm.*, 45:684–689, 1994.
90. Battey, J. F., et al., *Proc. Natl. Acad. Sci., USA*, 88:395–399, 1991.
91. Corjay, M. H., et al., *J. Biol. Chem.*, 266:18771–18779, 1991.
92. Frankel, A., et al., *Cancer Res.*, 54:1613–1616, 1994.
93. Krenning, E. P., et al., *Eur. J. Nucl. Med.*, 20:283–292, 1993.
94. Lamberts, S. W. J., et al., *Endoc. Rev.*, 12:450–482, 1991.
95. O'Dorisio, T. M., *Regul. Pept. Lett.*, 5:52–55, 1994.
96. Schirmer, W. J., et al., *Surgery*, 114:745–752, 1993.
97. Brazeau, P., et al., *Science*, 179:77–79, 1973.
98. Guillemin, R., *Science*, 202:390–402, 1978.
99. Bauer, W. Briner, et al., *Life Sci.*, 31:1133–1141, 1982.
100. Cai, R., et al., *Proc. Natl. Acad. Sci., USA*, 83:1896–1900, 1986.

101. Vale, W., et al., *Metabolism*, 27:1391–1401, 1978 (suppl.)
102. Yamada, Y., et al., *Proc. Natl. Acad. Sci, USA*, 89:251–255, 1992.
103. Yamada, Y., et al., *Mol. Endocrinol*, 6:2136–2142, 1992.
104. Rohrer, I., et al., *Proc. Natl. Acad. Sci. USA*, 90:4196–4200, 1993.
105. Mosley, B., et al., *Cell*, 59:335–348, 1989.
106. Paul, W., *Blood*, 77:1859–1870, 1991.
107. Buchsbaum D, et al., *Neurology* 40(Suppl. 1):397, 1990.
108. Buchsbaum, D., et al., *Int. J. Radiat. Onc. Biol.*, 18:1033–1041, 1990.
109. Buchsbaum, D., et al., *Eur. J. Nucl. Med.* 10:398–402, 1985.
110. Buchsbaum, D. J., et al., *Int. J. Nucl. Med. Biol.* 12:79–82, 1985.
111. Buchsbaum D., et al., *Cancer Res.*, 48:4324–4333, 1988.
112. Buchsbaum D. J., et al., *Cancer Res.*, (Suppl) 50:993s–999s, 1990.
113. Ram S., et al., *Cancer*, 73:769–773, 1994.
114. Ram S., et al., *Cancer*, 73:808–815, 1994.
115. Buchsbaum D. J., et al., Cancer 73:999–1005, 1994.
116. Muthuswamy M., et al., *Int. J. Radiat. Oncol. Biol. Phys.* In Press, 1994.
117. Buchsbaum D., et al., *Cancer Res.*, Submitted 1994.
118. Buchsbaum D. J. *Cancer Therapy with Radiolabeled Antibodies*, D. 119. Goldenberg (ed.), CRC Press, Boca Raton, Fla., pp.115–140, 1994.
120. Buchsbaum D., et al., The Fifth Conf. on Radioimmunodetection and Radioimmunotherapy of Cancer, Princeton, N.J., Oct. 6–8, 1994.
121. Srivastava P. C., et al., *Nucleosides & Nucleotides* 10:235–238, 1991.
122. Wahl R. L., et al., *Cancer*, 67:1544–1550, 1991.
123. Hasan A., et al., *J. Heterocyclic Chem.*, 30:1351–1355, 1993.
124. Buchsbaum D. J., et al., *Recent Results in Cancer Research*, M. Wannenmacher, (ed.), Springer-Verlag, New York, In Press, 1995. Roberson P. L., et al., The Fifth Conf. on Radioimmunodetection and Radioimmunotherapy of Cancer, Princeton, N.J., Oct. 6–8, 1994.
125. Safavy A., et al., *Bioconjugate Chem.*, 4:194–198, 1993.
126. Zhou Y. G., et al., *Antibody, Immunoconjugates and Radiopharm.*, Submitted 1994.
127. Safavy A., et al., *J. Nucl. Med.* 34:29P, 1993.
128. Safavy A., et al., *Antibody Immunoconjugates, Radiopharm.* 7:85, 1994.
129. Zhou Y. G., et al., *J. Labelled Compd. Radiopharm.*, 35:387–388, 1994.
130. Zhou Y., et al., *J. Labelled Comp. Radiopharm.*, 35:318–319, 1994.
131. Safavy A., et al., *J. Nucl. Med.*, 35:258P–259P, 1994.
132. Roberson, P., et al., *Int. J. Radiat. Oncol. Biol.* 24:329–334, 1992.
133. Roberson, P. L., et al., *Antibody, Immunoconjug., and Radiopharm.* 5:397–402, 1992.
134. Roberson, P. L., et al., *Cancer* 73:912–918, 1994.
135. Culver, K. W., et al., *Science* 256:1550–1552, 1992.
136. Ram, Z., et al., *Cancer Res.* 53:83–88, 1993.
137. Nabel, G. J., et al., *Human Gene Therapy* 5:57–77, 1994.
138. Herz, J. et al., *Proc. Natl. Acad. Sci. USA*, 90:2812–2816, 1993.
139. Becker, T. C., et al., *Meth. Cell Biol.*, 43:161–189, 1994.
140. Feng, M., et al., *Cancer Res.*, 55:2024–2028, 1995.
141. Muraro, R., et al., *Cancer Res.*, 45: 5769–5780, 1985.
142. Muraro, R., et al., *Cancer Res.*, 48:4588–4596, 1988.
143. Fraker, P., et al., *Biochem. Biophys. Res. Commun.*, 80:849–857, 1987.
144. Buchsbaum, D. J., et al., *Int. J. Radiat. Oncol. Biol.*, 25:629–638, 1993.
145. Lindmo, T., et al., *J. Immunol. Methods*, 72:77–89, 1984.
146. Buchsbaum, D., et al., *Cancer Res.*, In Press, 1995.
147. Meredith, R., et al., *Hum. Antibod. Hybrid.* 4:190–197, 1993.
148. Myers, R. B., et al., *J. Urol.*, 152:243–246, 1994.
149. Myers, R. B., et al., *J. Urol.*, 153:1572–1574, 1995.
150. Buchsbaum, D., et al., *Cancer Res.*, 48:4324–4333, 1988.
151. Guadagni, F., et al., *Cancer Res.*, 50:6248–6255, 1990.
152. Hand, P. H., et al., *Cancer Immunol. Immunother.*, 36:65–75, 1993.
153. Snedecor, G. W. et al., Statistical Methods. 7th ed., Ames, Iowa: The Iowa State University Press, 1980.
154. Goldenberg, D. M., et al., *N. Engl. J. Med.*, 298:1384–1388, 1978.
155. Sharkey, R. M., et al., *Cancer Res.*, 48:3270–3275, 1988.
156. Bischof-Delaloye, A., et al., *J. Nucl. Med.*, 30:1646–1656, 1989.
157. Buchegger, F., et al., *J. Nucl. Med.*, 31:1035–1044, 1990.
158. Sharkey, R. M., et al., *Cancer Res.*, 50:2330–2336, 1990.
159. Esteban, J. M., et al., *Cancer Res.*, 51:3802–3806, 1991.
160. Goldenberg, D. M., *Am. J. Gastroenterol.*, 86:1392–1403, 1991.
161. Corbisiero, R. M., et al., *Cancer Res.*, 51:5704–5711, 1991.
162. Goldenberg, D. M. et al., *J. Nucl. Med.*, 33:803–814, 1992.
163. Blumenthal, R. D., et al., *Cancer Res.*, 52:6036–6044, 1992.
164. Goldenberg, D. M., et al., *J. Nucl. Med.*, 34:61–70, 1993.
165. Sharkey, R. M., et al., *Cancer*, 71:2082–2096, 1993.
166. Blumenthal, R. D., et al., *Cancer Res.*, 54:142–151, 1994.
167. Murray, J. L., et al., *Cancer*, 73:850–857, 1994.
168. Behr, T. M., et al., *J. Nucl. Med.*, 36:430–441, 1995.
169. Gold, P. et al., *J. Exp. Med.*, 121:439–462, 1965.
170. Thompson, J. A., et al., *J. Clin. Lab. Anal.*, 5:344–366, 1991.
171. Hefta, L. J. F., et al., *Cancer Res.*, 50:2397–2403, 1990.
172. Robbins, P. F., et al., *Cancer Res.*, 51:3657–3662, 1991.
173. Guadagni, F., et al., *Cancer Immunol. Immunother.*, 26:222–230, 1988.
174. Rosenblum, M. G., et al., *J. Natl. Cancer Inst.*, 80:160–165, 1988.
175. Kuhn, J. A., et al., *Cancer Res.*, 51:2335–2339, 1991.
176. Greiner, J. W., et al., *J. Clin. Oncol.*, 10:735–746, 1992.
177. Greiner, J. W., et al., *Cancer Res.*, 53:600–608, 1993.
178. Aaronson, S. A., *Science*, 254:1146–1153, 1991.
179. De Santes, K., et al., *Cancer Res.*, 52:1916–1923, 1992.
180. Larson, S., *J. Nucl. Med.*, 32:1189–1191, 1991.
181. Krenning, E. P., et al., *N. Engl. J. Med.*, 331:1116–1121, 1994.

182. Weichselbaum, R. R., et al., *Cancer Res.*, 54:4266–4269, 1994.
183. Kim, J. H., et al., *Cancer Res.*, 54:6053–6056, 1994.
184. Garver, Jr., et al., *Gene Therapy*, 1:46–50, 1994.
185. DiMaio, J. M., et al., *Surgery*, 116:205–213, 1994.
186. Osaki, T., et al., *Cancer Res.*, 54:5258–5261, 1994.
187. Manome, Y., et al., *Cancer Res.*, 54:5408–5413, 1994.
188. Vile, R. G., et al., *Cancer Res.*, 54:6228–6234, 1994.
189. Richards, C. A., et al., *Human Gene Therapy*, 6:881–893, 1995.
190. Gazit, G., et al., *Cancer Res.*, 55:1660–1663, 1995.
191. Humm, J. L. et al., *Radiat. Res.*, 134:143–150, 1993.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An immunodiagnostic method of enhancing radiolabeled ligand localization to a solid tumor in vivo in an individual in need of such diagnosis, comprising the steps of:

transducing said tumor in vivo with a gene encoding a membrane expressed protein unique to said tumor; and administering to said individual a radiolabeled ligand which specifically binds to said protein.

2. The method of claim 1, wherein said tumor is selected from the group consisting of colon tumors, lung tumors and glioma tumors.

3. The method of claim 2, wherein said tumor is transduced by direct intratumor gene transfer in vivo.

4. The method of claim 1, wherein said tumor is selected from the group consisting of intraperitoneal ovarian tumors and colon tumors.

5. The method of claim 4, wherein said tumor is transduced by intraperitoneal gene transfer in vivo.

6. The method of claim 1, wherein said tumor is an intracerebral glioma tumor.

7. The method of claim 6, wherein said tumor is transduced by stereotactic direct gene transfer.

8. The method of claim 1, wherein said tumor is selected from the group consisting of systemic colon tumors and lung tumors.

9. The method of claim 8, wherein said tumor is transduced by systemic gene transfer.

10. The method of claim 1, wherein said protein is selected from the group consisting of an antigen and a receptor.

11. The method of claim 10, wherein said antigen is epidermal growth factor receptor and the radiolabeled ligand which specifically binds to said antigen is selected from the group consisting of monclonal antibody 528 and monocolonal antibody EGFR1.

12. The method of claim 10, wherein said antigen is the estrogen receptor and the radiolabeled ligand which specifically binds to said antigen is anti-estriol-3-sulfate.

13. The method of claim 10, wherein said receptor is the epidermal growth factor receptor and said radiolabeled ligand is selected from the group consisting of epidermal growth factor and transforming growth factor-alpha.

14. The method of claim 10, wherein said receptor is the estrogen receptor and the radiolabeled ligand which specifically binds to said receptor is selected from the group consisting of tamoxifen, estradiol, estradiol derivatives, estrogen and fluoroalanine.

15. The method of claim 10, wherein said receptor is the gastrin releasing peptide receptor and the radiolabeled ligand which specifically binds to said receptor is selected from the group consisting of bombesin, bombesin analogues and gastrin releasing peptide.

16. The method of claim 10, wherein said receptor is the interleukin-4 receptor and the radiolabeled ligand which specifically binds to said receptor is interleukin-4.

17. The method of claim 10, wherein said receptor is the somatostatin receptor and the radiolabeled ligand which specifically binds to said receptor is octreotide.

18. The method of claim 10, wherein said receptor is the vasoactive intestinal peptide receptor and the radiolabeled ligand which specifically binds to said receptor is vasoactive intestinal peptide.

19. The method of claim 1, wherein said radiolabeled ligand is an antibody.

20. The method of claim 1, wherein said radiolabeled ligand is a peptide.

21. The method of claim 1, wherein said transducion is by adenoviral mediated gene transfer.

22. The method of claim 1, wherein said radiolabel is selected from the group consisting of $^{123}I$, $^{125}I$, $^{131}I$, $^{32}P$, $^{64}Cu$, $^{67}Cu$, $^{211}At$, $^{177}Lu$, $^{90}Y$, $^{186}Re$, $^{212}Pb$, $^{212}Bi$, $^{47}Sc$, $^{105}Rh$, $^{109}Pd$, $^{153}Sm$, $^{188}Re$, $^{199}Au$, $^{211}At$, and $^{213}Bi$.

* * * * *

UNITED STATES PATENT AND TRADEMARK OFFICE
CERTIFICATE OF CORRECTION

PATENT NO. : 5,902,583
DATED : May 11, 1999
INVENTOR(S) : Donald J. Buchsbaum, et al.

It is certified that error appears in the above-indentified patent and that said Letters Patent is hereby corrected as shown below:

On the title page under item [75] Inventors, "Khazaell" should read --Khazaeli--.

Signed and Sealed this

Second Day of November, 1999

Attest:

Attesting Officer

Q. TODD DICKINSON

Acting Commissioner of Patents and Trademarks